US006936249B1

(12) United States Patent
Estell et al.

(10) Patent No.: US 6,936,249 B1
(45) Date of Patent: Aug. 30, 2005

(54) PROTEINS PRODUCING AN ALTERED IMMUNOGENIC RESPONSE AND METHODS OF MAKING AND USING THE SAME

(75) Inventors: David A. Estell, San Mateo, CA (US); Fiona A. Harding, Santa Clara, CA (US)

(73) Assignee: Genencor International, Inc., Palo Alto, CA (US)

( * ) Notice: Subject to any disclaimer, the term of this patent is extended or adjusted under 35 U.S.C. 154(b) by 346 days.

(21) Appl. No.: 09/677,822

(22) Filed: Oct. 2, 2000

Related U.S. Application Data

(63) Continuation-in-part of application No. 09/500,135, filed on Feb. 8, 2000, now Pat. No. 6,838,269, which is a continuation-in-part of application No. 09/060,872, filed on Apr. 15, 1998, now Pat. No. 6,835,550.

(51) Int. Cl.[7] ................................ A61K 39/00

(52) U.S. Cl. ................................ 424/184.1; 424/192.1

(58) Field of Search ................................ 424/184.1–277.1

(56) References Cited

U.S. PATENT DOCUMENTS

| | | | | |
|---|---|---|---|---|
| 4,261,868 A | | 4/1981 | Hora et al. | 252/529 |
| 4,404,128 A | | 9/1983 | Anderson | 252/546 |
| 4,533,359 A | | 8/1985 | Kondo et al. | 8/128 |
| 5,147,642 A | | 9/1992 | Lotz et al. | 424/94.61 |
| 5,182,204 A | | 1/1993 | Estell et al. | 435/222 |
| 5,185,258 A | | 2/1993 | Caldwell et al. | 435/220 |
| 5,204,015 A | | 4/1993 | Caldwell et al. | 252/174.12 |
| 5,264,366 A | | 11/1993 | Ferrari et al. | 435/252.31 |
| RE34,606 E | | 5/1994 | Estell et al. | 435/222 |
| 5,314,692 A | | 5/1994 | Haarasilta et al. | 424/94.2 |
| 5,500,366 A | * | 3/1996 | Russell-Jones et al. | 435/252.3 |
| 5,612,055 A | | 3/1997 | Bedford et al. | 424/442 |
| 6,060,281 A | * | 5/2000 | Grieve et al. | 435/69.3 |

FOREIGN PATENT DOCUMENTS

| | | | |
|---|---|---|---|
| EP | 0 134 267 | | 8/1989 |
| EP | 0 251 446 B1 | | 12/1994 |
| EP | 0 699 755 | | 3/1996 |
| WO | WO 89/06279 | | 7/1989 |
| WO | WO 92/10755 | | 6/1992 |
| WO | WO 94/10191 | | 5/1994 |
| WO | 9505849 | * | 3/1995 |
| WO | WO 96/16177 | | 5/1996 |
| WO | WO 96/17929 | | 6/1996 |
| WO | WO 96/40791 | | 12/1996 |
| WO | WO 97/30148 | | 8/1997 |
| WO | WO 98/52976 | | 11/1998 |
| WO | 9906061 | * | 2/1999 |
| WO | WO 99/53038 | | 10/1999 |
| WO | WO 99/61637 | | 12/1999 |
| WO | WO 00/34317 | | 6/2000 |

OTHER PUBLICATIONS

Lipford et al, Immunology, 84, 298–303, 1995.*

Graziano et al., "Enhancing the Immunogenicity of a Permissive Binding T Cell Epitope derived from the Simian Immunodeficiency Virus–Encoded Negative Regulatory Factor," *J. of Immun.,* V. 149, No. 2, 1991, pp. 556–561.

Lipford et al., "Peptide engineering allows cytotoxic T–cell vaccination against human papilloma virus tumour antigen, E6", Abstract, Database accession No. PREV199598171988.

Altschul et al., "Basic Local Alignment Search Tool," J. Mol. Biol., vol. 215, pp. 403–410, 1990.

Giver et al., "Directed evolution of a thermostable esterase," Proc. Natl. Acad. Sci. USA, vol. 95, pp. 12809–12813, 1998.

Harayama, Shigeaki, "Artificial evolution by DNA shuffling," TIBTECH., vol. 16, 6, pp., 1998.

Heinkoff et al., "Amino acid substitution matrices from protein blocks," Proc. Natl. Acad. Sci. USA, vol. 89, pp. 10915–10919, 1992.

Karlin et al., "Applications and statistics for multiple high–scoring segments in molecular sequences," Proc. Natl. Acad. Sci. USA, vol. 90, No. 12, pp. 5873–5788, 1993.

Kuchner et al, "Directed evolution of enzyme catalysts," TIBTECH, vol. 15, 9, pages, 1997.

Lin et al., "Functional Expression of Horseradish Peroxidase in *E. coli* by Directed Evolution," Biotechnol. Prog., vol. 15, pp. 467–471, 1999.

Mathew C. G., "The Isolation of High Molecular Weight Eurkaryotic DNA," Methods in Mol. Biol., vol. 2, pp. 31–33, 1984.

* Moeller, G., "Antigenic Requirements for Activation of MHC–Restricted Responses," Immun. Review, vol. 98, 1987.

Moore et al. "Strategies for the in vitro Evolution of Protein Function: Enzyme Evolution by Random Recombination of Improved Sequences," J. Mol. Biol., vol. 272, pp. 336–347, 1997.

Needleman et al., "A General Method Applicable to a Search for Similiarities in the Amino Acid Sequence of Two Proteins," J. Mol. Biol., vol. 48, pp. 443–453, 1970.

(Continued)

*Primary Examiner*—David Saunders
(74) *Attorney, Agent, or Firm*—Genencor International, Inc.

(57) ABSTRACT

The present invention relates to a novel methods and compositions for producing hyper and hypo allergenic compositions. Specifically, the present invention comprises neutralizing or reducing the ability of T-cells to recognize epitopes and thus prevent sensitization of an individual to the protein. Alternatively, T-cell epitopes are mutated to produce increased immunogenic reactions. Moreover, naturally occurring proteins are provided.

6 Claims, 34 Drawing Sheets

OTHER PUBLICATIONS

Pattern et al., "Applications of DNA shuffling to pharmaceutical and vaccines," Curr. Opinion Biotech., vol. 8, pp. 724–733, 1997.

Pearson et al., "Improved tools for biological sequence comparison." Proc. Natl. Acad. Sci. USA, vol. 85, pp. 2444–2448, 1997.

Smith et al., "Comparison of Biosequences," Adv. Appl. Math., vol. 2, pp. 482–489, 1981.

Stemmer, William P.C., "DNA shuffling by random fragmentation and reassembly: In vitro recombination for molecular evolution," Proc. Natl. Acad. Sci. USA, vol. 91, pp. 10747–10751, 1994.

Sun, F., "Modeling DNA Shuffling," J. Comp. Biol., vol. 6, pp. 77–90, 1999.

Zhao, H. et al, "Molecular evolution by staggered extension process (StEP) in vitro recombination," Nature Biotechnology, vol. 16, pp. 258–261, 1998.

Copy of PCT partial search of PCT/US 01/30062.

* cited by examiner

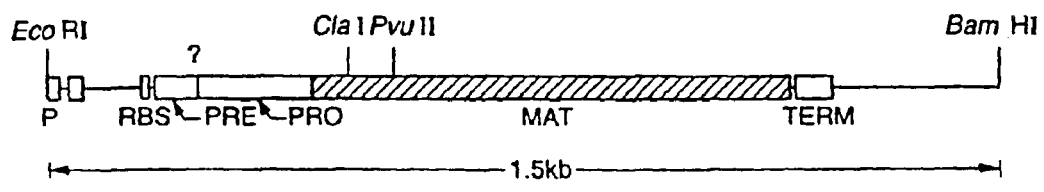
FIG._1A

```
                                                              RBS                           -107
                                                                                            Met
GGTCTACTAAAATATTATTCCATACTATACAATTAATACACAGAATAATCTGTCTATTGGTTATTCTGCAAATGAAAAAAGGAGGATAAAGA GTG
      P                                        (4)
     (3)
                        -100        PRE                                -90
     Arg Gly Lys Lys Val Trp Ser Leu Leu Phe Ala Leu Ala Leu Ile Phe Thr Met Ala Phe Gly Ser Thr Ser
  99 AGA GGC AAA AAA GTA TGG AGT ATC AGT TTG CTG TTT GCT TTA GCG TTA ATC TTT ACG ATG GCG TTC GGC AGC ACA TCC
             -80                           PRO        -70                               -60
     Ser Ala Gln Ala Ala Gly Lys Ser Asn Gly Glu Lys Lys Tyr Ile Val Gly Phe Lys Gln Thr Met Ser Thr Met
 174 TCT GCC CAG GCG GCA GGA AAA TCA AAC GGG GAA AAG AAA TAT ATT GTC GGG TTT AAA CAG ACA ATG AGC ACG ATG
             -50                       -40                               -30
     Ser Ala Ala Lys Lys Lys Asp Val Ile Ser Glu Lys Gly Gly Lys Val Gln Lys Gln Phe Lys Tyr Val Asp Ala
 249 AGC GCT GCT AAG AAG AAA GAT GTC ATT TCT GAA AAA GGG GGG AAA GTG CAA AAG CAA TTC AAA TAT GTA GAC GCA
             -30                 -20                                         -10
     Ala Ser Ala Thr Leu Asn Glu Lys Ala Val Lys Glu Leu Lys Lys Asp Pro Ser Val Ala Tyr Val Glu Glu Asp
 324 GCT TCA GCT ACA TTA AAC GAA GCT GTA AAA GAA TTG AAA AAG GAC CCG AGC GTC GCT TAT GTT GAA GAA GAT
                              -1  1                        10                              20
     His Val Ala His Ala Tyr Ala Gln Ser Val Pro Tyr Gly Val Ser Gln Ile Lys Ala Pro Ala Leu His Ser Gln
 399 CAC GTA GCA CAT GCG TAC GCG CAG TCC GTG CCT TAC GGC GTA TCA CAA ATT AAA GCC CCT GCT CTG CAC TCT CAA
                  MAT
                  ──→
              20                              30                              40
     Gly Tyr Thr Gly Ser Asn Val Lys Val Ala Val Ile Asp Ser Gly Ile Asp Ser Ser His Pro Asp Leu Lys Val
 474 GGC TAC ACT GGA TCA AAT GTT AAA GTA GCG GTT ATC GAT AGC GGT ATC GAT TCT TCT CAT CCT GAT TTA AAG GTA
```

```
                          Gln                                                    Asn
     Gln Val Arg Ser Ser  Leu Glu Asn Thr Thr Lys Leu Gly Asp Ser Phe Tyr Tyr Gly Lys Gly Leu Ile Asn
1149 CAA GTC CGC AGC AGT  TTA GAA AAC ACC ACT ACA AAA CTT GGT GAT TCT TTC TAC TAT GGA AAA GGG CTG ATC AAC
                     275                        TERM
     Val Gln Ala Ala Ala  Gln OC
1224 GTA CAG GCG GCA GCT CAG TAA AACATAAAAACCGGGCCTTGGCCCCGCCGGTTTTTATTTTCTTCCTCCGCATGTTCAATCCGGTCC

1315 ATAATCGACGGATGGCTCCCTCTGAAAATTTTAACGAGAACGGCGGTTGACCGGCTCAGTCCCGTAACGGCCAAGTCCTGAAACGTCTCAATCGCCG

1416 CTTCCCGGTTCCGGTCAGCTCAATGCCGTAACGGTCGGCCGGGTTTCCTGATACCGGGAGACGGCATTCGTAATCGGATC
```

FIG._1B-3

| FIG._1B-1 |
| FIG._1B-2 |
| FIG._1B-3 |

FIG._1B

CONSERVED RESIDUES IN SUBTILISINS FROM
*BACILLUS AMYLOLIQUEFACIENS*

COMPARISON OF SUBTILISIN SEQUENCES FROM:
B.amyloliquefaciens
B.subtilis
B.licheniformis
B.lentus

```
             10                  20                  30
01  AQSVPYGVSQIKAPALHSQGYTGSNVKVAVIDSGIDSSHP
    AQSVPYGISQIKAPALHSQGYTGSNVKVAVIDSGIDSSHP
    AQTVPYGIPLIKADKVQAQGFKGANVKVAVLDTGIQASHP
    AQSVPWGISRVQAPAAHNRGLTGSGVKVAVLDTGIST*H 50                  60                  70
41  DLKVAGGASMVPSETNPFQDNNSHGTHVAGTVAALNNSIG
    DLNVRGGASFVPSETNPYQDGSSHGTHVAGTIAALNNSIG
    DLNIRGGASFVPGEPSTQDGNGHGTHVAGTIAALDNTTGV*
    DLNIRGGASFVPGEPSTQDGNGHGTHVAGTIAALNNSIG 90                 100                 110
81  VLGVAPSASLYAVKVLGADGSGQYSWIINGIEWAIANNMD
    VLGVAPSASLYAVKVLDSTGSGQYSWIINGIEWAISNNMD
    VLGVAPSVSLYAVKVLGASGSGSVSSIAQGLEWAGNNGMH
    VANLSLGSPSGSALVAVKVLGASGSGSISSIAQGLEWAGNNGMH 130                 140                 150
121 VINMSLGGPSGSAALKAAVDKAVASGVVVVAAAGNEGTSG
    VINMSLGGPTGSTAMKQAVDNAYARGVVVVAAAGNEGSSG
    VINMSLGGASGSTAMKQAVDNAYARGVVVVAAAGNSGAGS
    VANLSLGSPSGSAATLEQAVNSATSRGVLVVAASGNSGAGS
```

```
161                170        180        190
SSTTVGYPGKYPSVIAVGAVDSSNQRASPSSVGPELDDVMA
STT..YGYPAKYPTIAVGAVNSSNRASFSSAGSELDVMA
STN..HGYPAKYDSVIAVGAVDSSNRASFSSVGAELEVMA
S.....GYPARYANAMAVGATDQNNRASFSQYGAGLDIVA 201                210        220        230
PGVSSHIQSTLPGNKYGAYNGTSMASPHVAGAAALILSKHPN
PGVSSHIQSTLPGGTYATTLNGTSMATPHVAGAAALILSKHPT
PGAGVYVQSTYPTNTYPTLNGTSMASPHVAGAAALILSKHPN
PGVNYVQSTYPGSTYASLNGTSMATPHVAGAAALVKQKNPS 241                250        260        270
WTNTQVRSSLENTTTKLGDSFYYGKGLINVQAAAQ
WTNAQVRDRLESTATTYLGNSFYYGKGLIHVAAAAQ
LSASQVRNRHLKNTATTSLGSTNLYGSGLVNAEAATR
WSNVQIRNHLKNTATTSLGSTNLYGSGLVNAEAATR
```

| # | ID | Sequence | # | ID | Sequence |
|---|---|---|---|---|---|
| 1 | A12 | IKDFHVYFRESRDAG | 49 | E12 | SATSRGVLVVAASGN |
| 2 | A11 | LEQAVNSATSRGVLV | 50 | E11 | SRGVLVVAASGNSGA |
| 3 | A10 | AQSVPWGISRVQAPA | 51 | E10 | VLVVAASGNSGAGSI |
| 4 | A9 | VPWGISRVQAPAAHN | 52 | E9 | VAASGNSGAGSISYP |
| 5 | A8 | GISRVQAPAAHNRGL | 53 | E8 | SGNSGAGSISYPARY |
| 6 | A7 | RVQAPAAHNRGLTGS | 54 | E7 | SGAGSISYPARYANA |
| 7 | A6 | APAAHNRGLTGSGVK | 55 | E6 | GSISYPARYANAMAV |
| 8 | A5 | AHNRGLTGSGVKVAV | 56 | E5 | SYPARYANAMAVGAT |
| 9 | A4 | RGLTGSGVKVAVLDT | 57 | E4 | ARYANAMAVGATDQN |
| 10 | A3 | TGSGVKVAVLDTGIS | 58 | E3 | ANAMAVGATDQNNNR |
| 11 | A2 | GVKVAVLDTGISTHP | 59 | E2 | MAVGATDQNNNRASF |
| 12 | A1 | VAVLDTGISTHPDLN | 60 | E1 | GATDQNNNRASFSQY |
| 13 | B12 | LDTGISTHPDLNIRG | 61 | F12 | DQNNNRASFSQYGAG |
| 14 | B11 | GISTHPDLNIRGGAS | 62 | F11 | NNRASFSQYGAGLDI |
| 15 | B10 | THPDLNIRGGASFVP | 63 | F10 | ASFSQYGAGLDIVAP |
| 16 | B9 | DLNIRGGASFVPGEP | 64 | F9 | SQYGAGLDIVAPGVN |
| 17 | B8 | IRGGASFVPGEPSTQ | 65 | F8 | GAGLDIVAPGVNVQS |
| 18 | B7 | GASFVPGEPSTQDGN | 66 | F7 | LDIVAPGVNVQSTYP |
| 19 | B6 | FVPGEPSTQDGNGHG | 67 | F6 | VAPGVNVQSTYPGST |
| 20 | B5 | GEPSTQDGNGHGTHV | 68 | F5 | GVNVQSTYPGSTYAS |
| 21 | B4 | STQDGNGHGTHVAGT | 69 | F4 | VQSTYPGSTYASLNG |
| 22 | B3 | DGNGHGTHVAGTIAA | 70 | F3 | TYPGSTYASLNGTSM |
| 23 | B2 | GHGTHVAGTIAALNN | 71 | F2 | GSTYASLNGTSMATP |
| 24 | B1 | THVAGTIAALNNSIG | 72 | F1 | YASLNGTSMATPHVA |
| 25 | C12 | AGTIAALNNSIGVLG | 73 | G12 | LNGTSMATPHVAGAA |
| 26 | C11 | IAALNNSIGVLGVAP | 74 | G11 | TSMATPHVAGAAALV |
| 27 | C10 | LNNSIGVLGVAPSAE | 75 | G10 | ATPHVAGAAALVKQK |
| 28 | C9 | SIGVLGVAPSAELYA | 76 | G9 | HVAGAAALVKQKNPS |
| 29 | C8 | VLGVAPSAELYAVKV | 77 | G8 | GAAALVKQKNPSWSN |
| 30 | C7 | VAPSAELYAVKVLGA | 78 | G7 | ALVKQKNPSWSNVQI |
| 31 | C6 | SAELYAVKVLGASGS | 79 | G6 | KQKNPSWSNVQIRNH |
| 32 | C5 | LYAVKVLGASGSGSV | 80 | G5 | NPSWSNVQIRNHLKN |
| 33 | C4 | VKVLGASGSGSVSSI | 81 | G4 | WSNVQIRNHLKNTAT |
| 34 | C3 | LGASGSGSVSSIAQG | 82 | G3 | VQIRNHLKNTATSLG |
| 35 | C2 | SGSGSVSSIAQGLEW | 83 | G2 | RNHLKNTATSLGSTN |
| 36 | C1 | GSVSSIAQGLEWAGN | 84 | G1 | LKNTATSLGSTNLYG |
| 37 | D12 | SSIAQGLEWAGNNGM | 85 | H12 | TATSLGSTNLYGSGL |
| 38 | D11 | AQGLEWAGNNGMHVA | 86 | H11 | SLGSTNLYGSGLVNA |
| 39 | D10 | LEWAGNNGMHVANLS | 87 | H10 | STNLYGSGLVNAEAA |
| 40 | D9 | AGNNGMHVANLSLGS | 88 | H9 | NLYGSGLVNAEAATR |
| 41 | D8 | NGMHVANLSLGSPSP | | | |
| 42 | D7 | HVANLSLGSPSPSAT | | | |
| 43 | D6 | NLSLGSPSPSATLEQ | | | |
| 44 | D5 | LGSPSPSATLEQAVN | | | |
| 45 | D4 | PSPSATLEQAVNSAT | | | |
| 46 | D3 | SATLEQAVNSATSRG | | | |
| 47 | D2 | LEQAVNSATSRGVLV | | | |
| 48 | D1 | AVNSATSRGVLVVAA | | | |

FIG. 6A

| # | ID | Sequence | # | ID | Sequence |
|---|---|---|---|---|---|
| 1 | A12 | IKDFHVYFRESRDAG | 49 | E12 | KKIDVLNLSIGGPDF |
| 2 | A11 | DAELHIFRVFTNNQV | 50 | E11 | DVLNLSIGGPDFMDH |
| 3 | A10 | PLRRASLSLGSGFWH | 51 | E10 | NLSIGGPDFMDHPFV |
| 4 | A9 | RASLSLGSGFWHATG | 52 | E9 | IGGPDFMDHPFVDKV |
| 5 | A8 | LSLGSGFWHATGRHS | 53 | E8 | PDFMDHPFVDKVWEL |
| 6 | A7 | GSGFWHATGRHSSRR | 54 | E7 | MDHPFVDKVWELTAN |
| 7 | A6 | FWHATGRHSSRRLLR | 55 | E6 | PFVDKVWELTANNVI |
| 8 | A5 | ATGRHSSRRLLRAIP | 56 | E5 | DKVWELTANNVIMVS |
| 9 | A4 | RHSSRRLLRAIPRQV | 57 | E4 | WELTANNVIMVSAIG |
| 10 | A3 | SRRLLRAIPRQVAQT | 58 | E3 | TANNVIMVSAIGNDG |
| 11 | A2 | LLRAIPRQVAQTLQA | 59 | E2 | NVIMVSAIGNDGPLY |
| 12 | A1 | AIPRQVAQTLQADVL | 60 | E1 | MVSAIGNDGPLYGTJ |
| 13 | B12 | RQVAQTLQADVLWQM | 61 | F12 | AIGNDGPLYGTLNNP |
| 14 | B11 | AQTLQADVLWQMGYT | 62 | F11 | NDGPLYGTLNNPADQ |
| 15 | B10 | LQADVLWQMGYTGAN | 63 | F10 | PLYGTLNNPADQMDV |
| 16 | B9 | DVLWQMGYTGANVRV | 64 | F9 | GTLNNPADQMDVIGV |
| 17 | B8 | WQMGYTGANVRVAVF | 65 | F8 | NNPADQMDVIGVGGI |
| 18 | B7 | GYTGANVRVAVFDTG | 66 | F7 | ADQMDVIGVGGIDFE |
| 19 | B6 | GANVRVAVFDTGLSE | 67 | F6 | MDVIGVGGIDFEDNI |
| 20 | B5 | VRVAVFDTGLSEKHP | 68 | F5 | IGVGGIDFEDNIARF |
| 21 | B4 | AVFDTGLSEKHPHFK | 69 | F4 | GGIDFEDNIARFSSR |
| 22 | B3 | DTGLSEKHPHFKNVK | 70 | F3 | DFEDNIARFSSRGMT |
| 23 | B2 | LSEKHPHFKNVKERT | 71 | F2 | DNIARFSSRGMTTWE |
| 24 | B1 | KHPHFKNVKERTNWT | 72 | F1 | ARFSSRGMTTWELPG |
| 25 | C12 | HFKNVKERTNWTNER | 73 | G12 | SSRGMTTWELPGGYG |
| 26 | C11 | NVKERTNWTNERTLD | 74 | G11 | GMTTWELPGGYGRMK |
| 27 | C10 | ERTNWTNERTLDDGL | 75 | G10 | TWELPGGYGRMKPDI |
| 28 | C9 | NWTNERTLDDGLGHG | 76 | G9 | LPGGYGRMKPDIVTY |
| 29 | C8 | NERTLDDGLGHGTFV | 77 | G8 | GYGRMKPDIVTYGAG |
| 30 | C7 | TLDDGLGHGTFVAGV | 78 | G7 | RMKPDIVTYGAGVRG |
| 31 | C6 | DGLGHGTFVAGVIAS | 79 | G6 | PDIVTYGAGVRGSGV |
| 32 | C5 | GHGTFVAGVIASMRE | 80 | G5 | VTYGAGVRGSGVKGG |
| 33 | C4 | TFVAGVIASMRECQG | 81 | G4 | GAGVRGSGVKGGCRA |
| 34 | C3 | AGVIASMRECQGFAP | 82 | G3 | VRGSGVKGGCRALSG |
| 35 | C2 | IASMRECQGFAPDAE | 83 | G2 | SGVKGGCRALSGTSV |
| 36 | C1 | MRECQGFAPDAELHI | 84 | G1 | KGGCRALSGTSVASP |
| 37 | D12 | CQGFAPDAELHIFRV | 85 | H12 | CRALSGTSVASPVVA |
| 38 | D11 | FAPDAELHIFRVFTN | 86 | H11 | LSGTSVASPVVAGAV |
| 39 | D10 | DAELHIFRVFTNNQV | 87 | H10 | TSVASPVVAGAVTLL |
| 40 | D9 | LHIFRVFTNNQVSYT | 88 | H9 | ASPVVAGAVTLLVST |
| 41 | D8 | FRVFTNNQVSYTSWF | 89 | H8 | VVAGAVTLLVSTVQK |
| 42 | D7 | FTNNQVSYTSWFLDA | 90 | H7 | GAVTLLVSTVQKREL |
| 43 | D6 | NQVSYTSWFLDAFNY | 91 | H6 | TLLVSTVQKRELVNP |
| 44 | D5 | SYTSWFLDAFNYAIL | 92 | H5 | VSTVQKRELVNPASM |
| 45 | D4 | SWFLDAFNYAILKKI | 93 | H4 | VQKRELVNPASMKQA |
| 46 | D3 | LDAFNYAILKKIDVL | 94 | H3 | RELVNPASMKQALIA |
| 47 | D2 | FNYAILKKIDVLNLS | 95 | H2 | VNPASMKQALIASAR |
| 48 | D1 | AILKKIDVLNLSIGG | 96 | H1 | ASMKQALIASARRLP |

FIG. 6B

| | | |
|---|---|---|
| 97 | I12 | IKDFHVYFRESRDAG |
| 98 | I11 | DAELHIFRVFTNNQV |
| 99 | I10 | KQALIASARRLPGVN |
| 100 | I9 | LIASARRLPGVNMFE |
| 101 | I8 | SARRLPGVNMFEQGH |
| 102 | I7 | RLPGVNMFEQGHGKL |
| 103 | I6 | GVNMFEQGHGKLDLL |
| 104 | I5 | MFEQGHGKLDLLRAY |
| 105 | I4 | QGHGKLDLLRAYQIL |
| 106 | I3 | GKLDLLRAYQILNSY |
| 107 | I2 | DLLRAYQILNSYKPQ |
| 108 | I1 | RAYQILNSYKPQASL |
| 109 | J12 | QILNSYKPQASLSPS |
| 110 | J11 | NSYKPQASLSPSYID |
| 111 | J10 | KPQASLSPSYIDLTE |
| 112 | J9 | ASLSPSYIDLTECPY |
| 113 | J8 | SPSYIDLTECPYMWP |
| 114 | J7 | YIDLTECPYMWPYCS |
| 115 | J6 | LTECPYMWPYCSQPI |
| 116 | J5 | CPYMWPYCSQPIYYG |

FIG. 6C

```
MKLVNIWLLLLVVLLCGKKHLGDRLEKKSFEKAPCPGCSHLTLKVEFSSTVVEYEYIVAFNGYFT
AKARNSFISSALKSSEVDNWRIIPRNNPSSDYPSDFEVIQIKEKQKAGLLTLEDHPNIKRVTPQR
KVFRSLKYAESDPTVPCNETRWSQKWQSSRPLRRASLSLGSGFWHATGRHSSRRLLRAIPRQVAQ
TLQADVLWQMGYTGANVRVAVFDTGLSEKHPHFKNVKERTNWTNERTLDDGLGHGTFVAGVIASM
RECQGFAPDAELHIFRVFTNNQVSYTSWFLDAFNYAILKKIDVLNLSIGGPDFMDHPFVDKVWEL
TANNVIMVSAIGNDGPLYGTLNNPADQMDVIGVGGIDFEDNIARFSSRGMTTWELPGGYGRMKPD
IVTYGAGVRGSGVKGGCRALSGTSVASPVVAGAVTLLVSTVQKRELVNPASMKQALIASARRLPG
VNMFEQGHGKLDLLRAYQILNSYKPQASLSPSYIDLTECPYMWPYCSQPIYYGGMPTVVNVTILN
GMGVTGRIVDKPDWQPYLPQNGDNIEVAFSYSSVLWPWSGYLAISISVTKKAASWEGIAQGHVMI
TVASPAETESKNGAEQTSTVKLPIKVKIIPTPPRSKRVLWDQYHNLRYPPGYFPRDNLRMKNDPL
DWNGDHIHTNFRDMYQHLRSMGYFVEVLGAPFTCFDASQYGTLLMVDSEEEYFPEEIAKLRRDVD
NGLSLVIFSDWYNTSVMRKVKFYDENTRQWWMPDTGGANIPALNELLSVWNMGFSDGLYEGEFTL
ANHDMYYASGCSIAKFPEDGVVITQTFKDQGLEVLKQETAVVENVPILGLYQIPAEGGGRIVLYG
DSNCLDDSHRQKDCFWLLDALLQYTSYGVTPPSLSHSGNRQRPPSGAGSVTPERMEGNHLHRYSK
VLEAHLGDPKPRPLPACPRLSWAKPQPLNETAPSNLWKHQKLLSIDLDKVVLPNFRSNRPQVRPL
SPGESGAWDIPGGIMPGRYNQEVGQTIPVFAFLGAMVVLAFFVVQINKAKSRPKRRKPRVKRPQL
MQQVHPPKTPSV
```

FIG. 7

```
              10        20        30        40        50
BPN'     AQSVPYGVSQ-IKAPALHSQGYTGSNVKVAVIDSGIDSSHPDLK-VAGGA  48
SAVINASE AQSVPWGISR-VQAPAAHNRGLTGSGVKVAVLDTGI-STHPDLN-IRGGA  47
S2HSBT   -RAIPRQVAQTLQADVLWQMGYTGANVRVAVFDTGLSEKHPHFKNVKERT  49

60        70        80        90       100
BPN'     SMVPSETNPFQDNNSHGTHVAGTVAALNNSIGVLGVAPSASLYAVKVLGA  98
SAVINASE SFVPGEPST-QDGNGHGTHVAGTIAALNNSIGVLGVAPSAELYAVKVLGA  96
S2HSBT   NW--TNERTLDDGLGHGTFVAGVIASMRECQGF---APDAELHIFRVFTN  94

110       120       130       140       150
BPN'     DGSGQYSWIINGIEWAIANNMDVINMSLGGPS-GSAALKAAVDKAVASGV  147
SAVINASE SGSGSVSSIAQGLEWAGNNGMHVANLSLGSPS-PSATLEQAVNSATSRGV  145
S2HSBT   NQVSYTSWFLDAFNYAILKKIDVLNLSIGGPDFMDHPFVDKVWELTANNV  144

160       170       180       190       200
BPN'     VVVAAAGNEGTSGSSSTVGYPGKYPSVIAVGAVDSSNQRASFSSVGPEL-  197
SAVINASE LVVAASGNSGA----GSISYPARYANAMAVGATDQNNNRASFSQYGAGL-  191
S2HSBT   IMVSAIGNDGP--LYGTLNNPADQMDVIGVGGIDFEDNIARFSSRGMTTW  192

210       220       230       240       250
BPN'     ----------DVMAPGVSIQSTLPGNKYGAYNGTSMASPHVAGAAALIL  235
SAVINASE ----------DIVAPGVNVQSTYPGSTYASLNGTSMATPHVAGAAALVK  229
S2HSBT   ELPGGYGRMKPDIVTYGAGVRGSGVKGGCRALSGTSVASPVVAGAVTLLV  242

260       270       280       290
BPN'     SKHPNWTNTQ---VRSSLENTTTKLGDSFYYGKGLINVQAAAQ       275
SAVINASE QKNPSWSNVQ---IRNHLKNTATSLGSTNLYGSGLVNAEAATR       269
S2HSBT   STVQKRELVNPASMKQALIASARRLPGVNMFEQG-----HGKL       280
```

FIG. 8

| Peptide number | Sequence |
| --- | --- |
| 1 (unmodified sequence) | GSISYPARYANAMAV |
| 2 | ASISYPARYANAMAV |
| 3 | GAISYPARYANAMAV |
| 4 | GSASYPARYANAMAV |
| 5 | GSIAYPARYANAMAV |
| 6 | GSISAPARYANAMAV |
| 7 | GSISYAARYANAMAV |
| 8 | GSISYPAAYANAMAV |
| 9 | GSISYPARAANAMAV |
| 10 | GSISYPARYAAAMAV |
| 11 | GSISYPARYANAAAV |
| 12 | GSISYPARYANAMAA |

```
            1          2          3          4          5
   1234567890 1234567890 1234567890 1234567890 1234567890
   MRSSPLLPSA VVAALPVLAL AADGRSTRYW DCCKPSCGWA KKAPVNQPVF
   SCNANFQRIT DFDAKSGCEP GGVAYSCADQ TPWAVNDDFA LGFAATSIAG
   SNEAGWCCAC YELTFTSGPV AGKKMVVQST STGGDLGSNH FDLNIPGGGV
   GIFDGCTPQF GGLPGQRYGG ISSRNECDRF PDALKPGCYW RFDWFKNADN
   PSFSFRQVQC PAELVARTGC RRNDDGNFPA VQIPSSSTSS PVNQPTSTST
   TSTSTTSSPP VQPTTPSGCT AERWAQ
```

FIG. 13B

```
  1 mrsslvlffv sawtalaspi rrevsqdlfn qfnlfaqysa aaycgknnda
 51 pagtnitctg nacpevekad atflysfeds gvgdvtqfla ldntnklivl
101 sfrgsrsien wignlnfdlk eindicsgcr ghdgftsswr svadtlrqkv
151 edavrehpdy rvvftghslg galatvagad lrgngydidv fsygaprvgn
201 rafaefltvq tggtlyrith tndivprlpp refgyshssp eywiksgtlv
251 pvtrndivki egidatggnn qpnipdipah lwyfgligtc l
```

FIG. 14B

```
  1 mftpvrrrvr taalalsaaa alvlgstaas gasatpspap apapapvkqg
 51 ptsvayvevn nnsmlnvgky tladggggnaf dvavifaani nydtgtktay
101 lhfnenvqrv ldnavtqirp lqqqgikvll svlqnhqgaq fanfpsqqaa
151 safakqlsda vakygldgvd fddeyaeygn ngtaqpndss fvhlvtalra
201 nmpdkiisly nigpaasrls yggvdvsdkf dyawnpyygt wqvpgialpk
251 aqlspaavei grtsrstvad larrtvdegy gvyltynldg gdrtadvsaf
301 trelygseav rtp
```

FIG. 15B

Hybrid enzyme sequence (GG36-BPN)

GG36
AQSVPWGISRVQAPAAHNRGLTGSGVKVAVLDTGISTHPDLNIRGGASFVPGEPSTQDGNGH

BPN

GTHVAGTIAALNNSIGVLGVAPSAELYAVKVLGASGSGSVSSIAQGLEWAGNNGMHVINMSLGGS
                                                                △

GSAALKAAVDKAVASGVVVVAAAGNEGTSGSSSTVGYPGKYPSVIAVGAVDSSNQRASFSSVGP

ELDVMAPGVSIQSTLPGNKYGAYNGTSMASPHVAGAAALILSKHPNWTNTQVRSSLENTTTKLGD

SFYY GKGLINVQAAAQ

FIG. 18

```
                         SEQUENCE LISTING

<160> NUMBER OF SEQ ID NOS: 240

<210> SEQ ID NO 1
<211> LENGTH: 1495
<212> TYPE: DNA
<213> ORGANISM: Bacillus amyloliquefaciens
<220> FEATURE:
<221> NAME/KEY: mat_peptide
<222> LOCATION: (417)..(1495)
<221> NAME/KEY: CDS
<222> LOCATION: (96)..(1244)
<221> NAME/KEY: misc_feature
<222> LOCATION: (582)..(584)
<223> OTHER INFORMATION: The nnn at positions 582 through 584 which in a
      preferred embodiment (aat) is to code for
      asparagine, but which may also code for proline.
<221> NAME/KEY: misc_feature
<222> LOCATION: (585)..(587)
<223> OTHER INFORMATION: The nnn at positions 585 through 587 which in a
      preferred embodiment (cct) is to code for proline,
      but which may also code for asparagine.
<221> NAME/KEY: misc_feature
<222> LOCATION: (597)..(599)
<223> OTHER INFORMATION: The nnn at positions 597 to 599 which in a
      preferred embodiment (aac) is to code for
      asparagine, but which may also code for aspartic acid.
<221> NAME/KEY: misc_feature
<222> LOCATION: (678)..(680)
<223> OTHER INFORMATION: The nnn at positions 678 through 680 which in a
      preferred embodiment (gca) is to code for
      alanine, but which may also code for serine.
<221> NAME/KEY: misc_feature
<222> LOCATION: (681)..(683)
<223> OTHER INFORMATION: The nnn at positions 681 through 683 which in a
      preferred embodiment (tca) is to code for serine,
      but which may also code for alanine.
<221> NAME/KEY: misc_feature
<222> LOCATION: (708)..(710)
<223> OTHER INFORMATION: The nnn at positions 708 through 710 which in a
      preferred embodiment (gct) is to code for
      alanine, but which may also code for aspartic acid.
<221> NAME/KEY: misc_feature
<222> LOCATION: (711)..(713)
<223> OTHER INFORMATION: The nnn at positions 711 through 713 which in a
      preferred embodiment (gac) is to code for
      aspartic acid, but which may also code for alanine.
<221> NAME/KEY: misc_feature
<222> LOCATION: (888)..(890)
<223> OTHER INFORMATION: The nnn at positions 888 through 890 which in a
      preferred embodiment (act) is to code for
      threonine, but which may also code for serine.
<221> NAME/KEY: misc_feature
<222> LOCATION: (891)..(893)
<223> OTHER INFORMATION: The nnn at positions 891 through 893 which in a
      preferred embodiment (tcc) is to code for
      serine, but which may also code for threonine.
<221> NAME/KEY: misc_feature
<222> LOCATION: (1167)..(1169)
```

-continued

<223> OTHER INFORMATION: The nnn at positions 1167 through 1169 which in
a preferred embodiment (gaa) is to code for
glutamic acid, but which may also code for glutamine.

<400> SEQUENCE: 1

```
ggtctactaa aatattattc catactatac aattaataca cagaataatc tgtctattgg         60
ttattctgca aatgaaaaaa aggagaggat aaaga atg aga ggc aaa aaa gta          113
                                       Met Arg Gly Lys Lys Val
                                                          -105 tgg atc agt ttg ctg ttt gct tta gcg tta atc ttt acg atg gcg ttc         161
Trp Ile Ser Leu Leu Phe Ala Leu Ala Leu Ile Phe Thr Met Ala Phe
    -100             -95                 -90 ggc agc aca tcc tct gcc cag gcg gca ggg aaa tca aac ggg gaa aag         209
Gly Ser Thr Ser Ser Ala Gln Ala Ala Gly Lys Ser Asn Gly Glu Lys
-85             -80                 -75                 -70 aaa tat att gtc ggg ttt aaa cag aca atg agc acg atg agc gcc gct         257
Lys Tyr Ile Val Gly Phe Lys Gln Thr Met Ser Thr Met Ser Ala Ala
            -65                 -60                 -55 aag aag aaa gat gtc att tct gaa aaa ggc ggg aaa gtg caa aag caa         305
Lys Lys Lys Asp Val Ile Ser Glu Lys Gly Gly Lys Val Gln Lys Gln
        -50                 -45                 -40 ttc aaa tat gta gac gca gct tca gct aca tta aac gaa aaa gct gta         353
Phe Lys Tyr Val Asp Ala Ala Ser Ala Thr Leu Asn Glu Lys Ala Val
    -35                 -30                 -25 aaa gaa ttg aaa aaa gac ccg agc gtc gct tac gtt gaa gaa gat cac         401
Lys Glu Leu Lys Lys Asp Pro Ser Val Ala Tyr Val Glu Glu Asp His
-20                 -15                 -10 gta gca cat gcg tac gcg cag tcc gtg cct tac ggc gta tca caa att         449
Val Ala His Ala Tyr Ala Gln Ser Val Pro Tyr Gly Val Ser Gln Ile
-5              -1   1               5                   10 aaa gcc cct gct ctg cac tct caa ggc tac act gga tca aat gtt aaa         497
Lys Ala Pro Ala Leu His Ser Gln Gly Tyr Thr Gly Ser Asn Val Lys
            15                  20                  25 gta gcg gtt atc gac agc ggt atc gat tct tct cat cct gat tta aag         545
Val Ala Val Ile Asp Ser Gly Ile Asp Ser Ser His Pro Asp Leu Lys
        30                  35                  40 gta gca ggc gga gcc agc atg gtt cct tct gaa aca nnn nnn ttc caa         593
Val Ala Gly Gly Ala Ser Met Val Pro Ser Glu Thr Xaa Xaa Phe Gln
    45                  50                  55 gac nnn aac tct cac gga act cac gtt gcc ggc aca gtt gcg gct ctt         641
Asp Xaa Asn Ser His Gly Thr His Val Ala Gly Thr Val Ala Ala Leu
60                  65                  70                  75 aat aac tca atc ggt gta tta ggc gtt gcg cca agc nnn nnn ctt tac         689
Asn Asn Ser Ile Gly Val Leu Gly Val Ala Pro Ser Xaa Xaa Leu Tyr
            80                  85                  90 gct gta aaa gtt ctc ggt nnn nnn ggt tcc ggc caa tac agc tgg atc         737
Ala Val Lys Val Leu Gly Xaa Xaa Gly Ser Gly Gln Tyr Ser Trp Ile
        95                  100                 105 att aac gga atc gag tgg gcg atc gca aac aat atg gac gtt att aac         785
Ile Asn Gly Ile Glu Trp Ala Ile Ala Asn Asn Met Asp Val Ile Asn
    110                 115                 120 atg agc ctc ggc gga cct tct ggt tct gct gct tta aaa gcg gca gtt         833
Met Ser Leu Gly Gly Pro Ser Gly Ser Ala Ala Leu Lys Ala Ala Val
125                 130                 135 gat aaa gcc gtt gca tcc ggc gtc gta gtc gtt gcg gca gcc ggt aac         881
Asp Lys Ala Val Ala Ser Gly Val Val Val Ala Ala Ala Gly Asn
140                 145                 150                 155 gaa ggc nnn nnn ggc agc tca agc aca gtg ggc tac cct ggt aaa tac         929
Glu Gly Xaa Xaa Gly Ser Ser Ser Thr Val Gly Tyr Pro Gly Lys Tyr
            160                 165                 170
```

```
cct tct gtc att gca gta ggc gct gtt gac agc agc aac caa aga gca      977
Pro Ser Val Ile Ala Val Gly Ala Val Asp Ser Ser Asn Gln Arg Ala
            175                 180                 185 tct ttc tca agc gta gga cct gag ctt gat gtc atg gca cct ggc gta     1025
Ser Phe Ser Ser Val Gly Pro Glu Leu Asp Val Met Ala Pro Gly Val
                190                 195                 200 tct atc caa agc acg ctt cct gga aac aaa tac ggg gcg tac aac ggt     1073
Ser Ile Gln Ser Thr Leu Pro Gly Asn Lys Tyr Gly Ala Tyr Asn Gly
            205                 210                 215 acg tca atg gca tct ccg cac gtt gcc gga gcg gct gct ttg att ctt     1121
Thr Ser Met Ala Ser Pro His Val Ala Gly Ala Ala Ala Leu Ile Leu
220                 225                 230                 235 tct aag cac ccg aac tgg aca aac act caa gtc cgc agc agt tta nnn     1169
Ser Lys His Pro Asn Trp Thr Asn Thr Gln Val Arg Ser Ser Leu Xaa
                240                 245                 250 aac acc act aca aaa ctt ggt gat tct ttc tac tat gga aaa ggg ctg     1217
Asn Thr Thr Thr Lys Leu Gly Asp Ser Phe Tyr Tyr Gly Lys Gly Leu
            255                 260                 265 atc aac gta cag gcg gca gct cag taa aacataaaaa accggccttg            1264
Ile Asn Val Gln Ala Ala Ala Gln
                270                 275 gccccgccgg ttttttttatt tttcttcctc cgcatgttca atccgctcca taatcgacgg   1324
atggctccct ctgaaaattt taacgagaaa cggcggggttg acccggctca gtcccgtaac   1384
ggccaagtcc tgaaacgtct caatcgccgc ttcccggttt ccggtcagct caatgccgta   1444
acggtcggcg cgttttcct gataccggga gacggcattc gtaatcggat c             1495

<210> SEQ ID NO 2
<211> LENGTH: 382
<212> TYPE: PRT
<213> ORGANISM: Bacillus amyloliquefaciens
<220> FEATURE:
<221> NAME/KEY: VARIANT
<222> LOCATION: (163)...(163)
<223> OTHER INFORMATION: Xaa = Asn or Pro
<221> NAME/KEY: VARIANT
<222> LOCATION: (164)...(164)
<223> OTHER INFORMATION: Xaa = Pro or Asn
<221> NAME/KEY: VARIANT
<222> LOCATION: (168)...(168)
<223> OTHER INFORMATION: Xaa = Asn or Asp
<221> NAME/KEY: VARIANT
<222> LOCATION: (195)...(195)
<223> OTHER INFORMATION: Xaa = Ala or Ser
<221> NAME/KEY: VARIANT
<222> LOCATION: (196)...(196)
<223> OTHER INFORMATION: Xaa = Ser or Ala
<221> NAME/KEY: VARIANT
<222> LOCATION: (205)...(205)
<223> OTHER INFORMATION: Xaa = Ala or Asp
<221> NAME/KEY: VARIANT
<222> LOCATION: (206)...(206)
<223> OTHER INFORMATION: Xaa = Asp or Ala
<221> NAME/KEY: VARIANT
<222> LOCATION: (265)...(265)
<223> OTHER INFORMATION: Xaa = Thr or Ser
<221> NAME/KEY: VARIANT
<222> LOCATION: (266)...(266)
<223> OTHER INFORMATION: Xaa = Ser or Thr
<221> NAME/KEY: VARIANT
<222> LOCATION: (358)...(358)
<223> OTHER INFORMATION: Xaa = Gln or Glu

<400> SEQUENCE: 2

Met Arg Gly Lys Lys Val Trp Ile Ser Leu Leu Phe Ala Leu Ala Leu
 1               5                  10                  15

Ile Phe Thr Met Ala Phe Gly Ser Thr Ser Ser Ala Gln Ala Ala Gly
```

-continued

```
                  20                  25                  30
Lys Ser Asn Gly Glu Lys Tyr Ile Val Gly Phe Lys Gln Thr Met
            35                  40                  45

Ser Thr Met Ser Ala Ala Lys Lys Asp Val Ile Ser Glu Lys Gly
 50                  55                  60

Gly Lys Val Gln Lys Gln Phe Lys Tyr Val Asp Ala Ala Ser Ala Thr
 65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
                100                 105                 110

Tyr Gly Val Ser Gln Ile Lys Ala Pro Ala Leu His Ser Gln Gly Tyr
            115                 120                 125

Thr Gly Ser Asn Val Lys Val Ala Val Ile Asp Ser Gly Ile Asp Ser
 130                 135                 140

Ser His Pro Asp Leu Lys Val Ala Gly Gly Ala Ser Met Val Pro Ser
145                 150                 155                 160

Glu Thr Xaa Xaa Phe Gln Asp Xaa Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Xaa Xaa Leu Tyr Ala Val Lys Val Leu Gly Xaa Xaa Gly Ser
            195                 200                 205

Gly Gln Tyr Ser Trp Ile Ile Asn Gly Ile Glu Trp Ala Ile Ala Asn
 210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Xaa Xaa Gly Ser Ser Ser Thr Val
            260                 265                 270

Gly Tyr Pro Gly Lys Tyr Pro Ser Val Ile Ala Val Gly Ala Val Asp
 275                 280                 285

Ser Ser Asn Gln Arg Ala Ser Phe Ser Ser Val Gly Pro Glu Leu Asp
290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Xaa Asn Thr Thr Thr Lys Leu Gly Asp Ser Phe
 355                 360                 365

Tyr Tyr Gly Lys Gly Leu Ile Asn Val Gln Ala Ala Gln
 370                 375                 380
```

```
<210> SEQ ID NO 3
<211> LENGTH: 275
<212> TYPE: PRT
<213> ORGANISM: Bacillus amyloliquefaciens

<400> SEQUENCE: 3
```

```
Ala Gln Ser Val Pro Tyr Gly Val Ser Gln Ile Lys Ala Pro Ala Leu
 1                   5                  10                  15
```

-continued

```
His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
            165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
            245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 4
<211> LENGTH: 275
<212> TYPE: PRT
<213> ORGANISM: Bacillus subtilis

<400> SEQUENCE: 4

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110
```

```
Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
        130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275

<210> SEQ ID NO 5
<211> LENGTH: 274
<212> TYPE: PRT
<213> ORGANISM: Bacillus licheniformis

<400> SEQUENCE: 5

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
```

```
                195                 200                 205
Pro Thr Asn Thr Tyr Ala Thr Leu Asn Gly Thr Ser Met Ala Ser Pro
            210                 215                 220

His Val Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 7
<211> LENGTH: 15
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 7

Ile Lys Asp Phe His Val Tyr Phe Arg Glu Ser Arg Asp Ala Gly
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 8

Leu Glu Gln Ala Val Asn Ser Ala Thr Ser Arg Gly Val Leu Val
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 9

Ala Gln Ser Val Pro Trp Gly Ile Ser Arg Val Gln Ala Pro Ala
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 10

Val Pro Trp Gly Ile Ser Arg Val Gln Ala Pro Ala Ala His Asn
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 11

Gly Ile Ser Arg Val Gln Ala Pro Ala Ala His Asn Arg Gly Leu
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 12

Arg Val Gln Ala Pro Ala Ala His Asn Arg Gly Leu Thr Gly Ser
 1               5                  10                  15

<210> SEQ ID NO 13
<211> LENGTH: 15
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 13

Ala Pro Ala Ala His Asn Arg Gly Leu Thr Gly Ser Gly Val Lys
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 14

Ala His Asn Arg Gly Leu Thr Gly Ser Gly Val Lys Val Ala Val
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 15

Arg Gly Leu Thr Gly Ser Gly Val Lys Val Ala Val Leu Asp Thr
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 16

Thr Gly Ser Gly Val Lys Val Ala Val Leu Asp Thr Gly Ile Ser
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 17

Gly Val Lys Val Ala Val Leu Asp Thr Gly Ile Ser Thr His Pro
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 18

Val Ala Val Leu Asp Thr Gly Ile Ser Thr His Pro Asp Leu Asn
 1               5                  10                  15

<210> SEQ ID NO 19
<211> LENGTH: 15
<212> TYPE: PRT
<213> ORGANISM: Artificial Sequence
<220> FEATURE:
```

-continued

<223> OTHER INFORMATION: Description of Artificial Sequence: Synthetic

<400> SEQUENCE: 19

Leu Asp Thr Gly Ile Ser Thr His Pro Asp Leu Asn Ile Arg Gly
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 20

Gly Ile Ser Thr His Pro Asp Leu Asn Ile Arg Gly Gly Ala Ser
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 21

Thr His Pro Asp Leu Asn Ile Arg Gly Gly Ala Ser Phe Val Pro
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 22

Asp Leu Asn Ile Arg Gly Gly Ala Ser Phe Val Pro Gly Glu Pro
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 23

Ile Arg Gly Gly Ala Ser Phe Val Pro Gly Glu Pro Ser Thr Gln
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 24

Gly Ala Ser Phe Val Pro Gly Glu Pro Ser Thr Gln Asp Gly Asn
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic

```
<400> SEQUENCE: 25

Phe Val Pro Gly Glu Pro Ser Thr Gln Asp Gly Asn Gly His Gly
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 26

Gly Glu Pro Ser Thr Gln Asp Gly Asn Gly His Gly Thr His Val
 1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 27

Ser Thr Gln Asp Gly Asn Gly His Gly Thr His Val Ala Gly Thr
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 28

Asp Gly Asn Gly His Gly Thr His Val Ala Gly Thr Ile Ala Ala
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 29

Gly His Gly Thr His Val Ala Gly Thr Ile Ala Ala Leu Asn Asn
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 30

Thr His Val Ala Gly Thr Ile Ala Ala Leu Asn Asn Ser Ile Gly
 1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

```
<400> SEQUENCE: 31

Ala Gly Thr Ile Ala Ala Leu Asn Asn Ser Ile Gly Val Leu Gly
 1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 32

Ile Ala Ala Leu Asn Asn Ser Ile Gly Val Leu Gly Val Ala Pro
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 33

Leu Asn Asn Ser Ile Gly Val Leu Gly Val Ala Pro Ser Ala Glu
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 34

Ser Ile Gly Val Leu Gly Val Ala Pro Ser Ala Glu Leu Tyr Ala
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 35

Val Leu Gly Val Ala Pro Ser Ala Glu Leu Tyr Ala Val Lys Val
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 36

Val Ala Pro Ser Ala Glu Leu Tyr Ala Val Lys Val Leu Gly Ala
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 37
```

Ser Ala Glu Leu Tyr Ala Val Lys Val Leu Gly Ala Ser Gly Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 38

Leu Tyr Ala Val Lys Val Leu Gly Ala Ser Gly Ser Gly Ser Val
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 39

Val Lys Val Leu Gly Ala Ser Gly Ser Gly Ser Val Ser Ser Ile
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 40

Leu Gly Ala Ser Gly Ser Gly Ser Val Ser Ser Ile Ala Gln Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 41

Ser Gly Ser Gly Ser Val Ser Ser Ile Ala Gln Gly Leu Glu Trp
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 42

Gly Ser Val Ser Ser Ile Ala Gln Gly Leu Glu Trp Ala Gly Asn
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 43

```
Ser Ser Ile Ala Gln Gly Leu Glu Trp Ala Gly Asn Asn Gly Met
 1               5                  10                  15
```

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 44

```
Ala Gln Gly Leu Glu Trp Ala Gly Asn Asn Gly Met His Val Ala
 1               5                  10                  15
```

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 45

```
Leu Glu Trp Ala Gly Asn Asn Gly Met His Val Ala Asn Leu Ser
 1               5                  10                  15
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 46

```
Ala Gly Asn Asn Gly Met His Val Ala Asn Leu Ser Leu Gly Ser
 1               5                  10                  15
```

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 47

```
Asn Gly Met His Val Ala Asn Leu Ser Leu Gly Ser Pro Ser Pro
 1               5                  10                  15
```

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 48

```
His Val Ala Asn Leu Ser Leu Gly Ser Pro Ser Pro Ser Ala Thr
 1               5                  10                  15
```

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 49

Asn Leu Ser Leu Gly Ser Pro Ser Pro Ser Ala Thr Leu Glu Gln

```
<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 50

Leu Gly Ser Pro Ser Pro Ser Ala Thr Leu Glu Gln Ala Val Asn
 1               5                  10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 51

Pro Ser Pro Ser Ala Thr Leu Glu Gln Ala Val Asn Ser Ala Thr
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 52

Ser Ala Thr Leu Glu Gln Ala Val Asn Ser Ala Thr Ser Arg Gly
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 53

Leu Glu Gln Ala Val Asn Ser Ala Thr Ser Arg Gly Val Leu Val
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 54

Ala Val Asn Ser Ala Thr Ser Arg Gly Val Leu Val Val Ala Ala
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 55

Ser Ala Thr Ser Arg Gly Val Leu Val Val Ala Ala Ser Gly Asn
 1               5                  10                  15
```

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 56

Ser Arg Gly Val Leu Val Val Ala Ala Ser Gly Asn Ser Gly Ala
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 57

Val Leu Val Val Ala Ala Ser Gly Asn Ser Gly Ala Gly Ser Ile
 1               5                  10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 58

Val Ala Ala Ser Gly Asn Ser Gly Ala Gly Ser Ile Ser Tyr Pro
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 59

Ser Gly Asn Ser Gly Ala Gly Ser Ile Ser Tyr Pro Ala Arg Tyr
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 60

Ser Gly Ala Gly Ser Ile Ser Tyr Pro Ala Arg Tyr Ala Asn Ala
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 61

Gly Ser Ile Ser Tyr Pro Ala Arg Tyr Ala Asn Ala Met Ala Val
 1               5                  10                  15

```
<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 62

Ser Tyr Pro Ala Arg Tyr Ala Asn Ala Met Ala Val Gly Ala Thr
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 63

Ala Arg Tyr Ala Asn Ala Met Ala Val Gly Ala Thr Asp Gln Asn
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 64

Ala Asn Ala Met Ala Val Gly Ala Thr Asp Gln Asn Asn Asn Arg
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 65

Met Ala Val Gly Ala Thr Asp Gln Asn Asn Asn Arg Ala Ser Phe
 1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 66

Gly Ala Thr Asp Gln Asn Asn Asn Arg Ala Ser Phe Ser Gln Tyr
 1               5                  10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 67

Asp Gln Asn Asn Asn Arg Ala Ser Phe Ser Gln Tyr Gly Ala Gly
 1               5                  10                  15
```

```
<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 68

Asn Asn Arg Ala Ser Phe Ser Gln Tyr Gly Ala Gly Leu Asp Ile
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 69

Ala Ser Phe Ser Gln Tyr Gly Ala Gly Leu Asp Ile Val Ala Pro
 1               5                  10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 70

Ser Gln Tyr Gly Ala Gly Leu Asp Ile Val Ala Pro Gly Val Asn
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 71

Gly Ala Gly Leu Asp Ile Val Ala Pro Gly Val Asn Val Gln Ser
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 72

Leu Asp Ile Val Ala Pro Gly Val Asn Val Gln Ser Thr Tyr Pro
 1               5                  10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 73

Val Ala Pro Gly Val Asn Val Gln Ser Thr Tyr Pro Gly Ser Thr
 1               5                  10                  15

<210> SEQ ID NO 74
```

```
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 74

Gly Val Asn Val Gln Ser Thr Tyr Pro Gly Ser Thr Tyr Ala Ser
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 75

Val Gln Ser Thr Tyr Pro Gly Ser Thr Tyr Ala Ser Leu Asn Gly
 1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 76

Thr Tyr Pro Gly Ser Thr Tyr Ala Ser Leu Asn Gly Thr Ser Met
 1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 77

Gly Ser Thr Tyr Ala Ser Leu Asn Gly Thr Ser Met Ala Thr Pro
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 78

Tyr Ala Ser Leu Asn Gly Thr Ser Met Ala Thr Pro His Val Ala
 1               5                  10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 79

Leu Asn Gly Thr Ser Met Ala Thr Pro His Val Ala Gly Ala Ala
 1               5                  10                  15

<210> SEQ ID NO 80
<211> LENGTH: 15
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 80

Thr Ser Met Ala Thr Pro His Val Ala Gly Ala Ala Ala Leu Val
 1               5                  10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 81

Ala Thr Pro His Val Ala Gly Ala Ala Ala Leu Val Lys Gln Lys
 1               5                  10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 82

Gly Val Ala Gly Ala Ala Ala Leu Val Lys Gln Lys Asn Pro Ser
 1               5                  10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 83

Gly Ala Ala Ala Leu Val Lys Gln Lys Asn Pro Ser Trp Ser Asn
 1               5                  10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 84

Ala Leu Val Lys Gln Lys Asn Pro Ser Trp Ser Asn Val Gln Ile
 1               5                  10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 85

Lys Gln Lys Asn Pro Ser Trp Ser Val Asn Gln Ile Arg Asn His
 1               5                  10                  15

<210> SEQ ID NO 86
<211> LENGTH: 15
<212> TYPE: PRT
```

<213> ORGANISM: Artificial Sequence
<220> FEATURE:
<223> OTHER INFORMATION: Description of Artificial Sequence: Synthetic

<400> SEQUENCE: 86

Asn Pro Ser Trp Ser Asn Val Gln Ile Arg Asn His Leu Lys Asn
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 87

Trp Ser Asn Val Gln Ile Arg Asn His Leu Lys Asn Thr Ala Thr
 1               5                  10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 88

Val Gln Ile Arg Asn His Leu Lys Asn Thr Ala Thr Ser Leu Gly
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 89

Arg Asn His Leu Lys Asn Thr Ala Thr Ser Leu Gly Ser Thr Asn
 1               5                  10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 90

Leu Lys Asn Thr Ala Thr Ser Leu Gly Ser Thr Asn Leu Tyr Gly
 1               5                  10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 91

Thr Ala Thr Ser Leu Gly Ser Thr Asn Leu Tyr Gly Ser Gly Leu
 1               5                  10                  15

<210> SEQ ID NO 92
<211> LENGTH: 15
<212> TYPE: PRT
<213> ORGANISM: Artificial Sequence

```
<220> FEATURE:
<223> OTHER INFORMATION: Description of Artificial Sequence: Synthetic

<400> SEQUENCE: 92

Ser Leu Gly Ser Thr Asn Leu Tyr Gly Ser Gly Leu Val Asn Ala
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 93

Ser Thr Asn Leu Tyr Gly Ser Gly Leu Val Asn Ala Glu Ala Ala
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 94

Asn Leu Tyr Gly Ser Gly Leu Val Asn Ala Glu Ala Ala Thr Arg
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 95

Asp Ala Glu Leu His Ile Phe Arg Val Phe Thr Asn Asn Gln Val
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 96

Pro Leu Arg Arg Ala Ser Leu Ser Leu Gly Ser Gly Phe Trp His
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 97

Arg Ala Ser Leu Ser Leu Gly Ser Gly Phe Trp His Ala Thr Gly
1               5                   10                  15

<210> SEQ ID NO 98
<211> LENGTH: 15
<212> TYPE: PRT
<213> ORGANISM: Artificial Sequence
<220> FEATURE:
```

<223> OTHER INFORMATION: Description of Artificial Sequence: Synthetic

<400> SEQUENCE: 98

Leu Ser Leu Gly Ser Gly Phe Trp His Ala Thr Gly Arg His Ser
 1               5                  10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 99

Gly Ser Gly Phe Trp His Ala Thr Gly Arg His Ser Ser Arg Arg
 1               5                  10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 100

Phe Trp His Ala Thr Gly Arg His Ser Ser Arg Arg Leu Leu Arg
 1               5                  10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 101

Ala Thr Gly Arg His Ser Ser Arg Arg Leu Leu Arg Ala Ile Pro
 1               5                  10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 102

Arg His Ser Ser Arg Arg Leu Leu Arg Ala Ile Pro Arg Gln Val
 1               5                  10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 103

Ser Arg Arg Leu Leu Arg Ala Ile Pro Arg Gln Val Ala Gln Thr
 1               5                  10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 104

Leu Leu Arg Ala Ile Pro Arg Gln Val Ala Gln Thr Leu Gln Ala
 1               5                  10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 105

Ala Ile Pro Arg Gln Val Ala Gln Thr Leu Gln Ala Asp Val Leu
 1               5                  10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 106

Arg Gln Val Ala Gln Thr Leu Gln Ala Asp Val Leu Trp Gln Met
 1               5                  10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 107

Ala Gln Thr Leu Gln Ala Asp Val Leu Trp Gln Met Gly Tyr Thr
 1               5                  10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 108

Leu Gln Ala Asp Val Leu Trp Gln Met Gly Tyr Thr Gly Ala Asn
 1               5                  10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 109

Asp Val Leu Trp Gln Met Gly Tyr Thr Gly Ala Asn Val Arg Val
 1               5                  10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 110

Trp Gln Met Gly Tyr Thr Gly Ala Asn Val Arg Val Ala Val Phe
 1               5                  10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 111

Gly Tyr Thr Gly Ala Asn Val Arg Val Ala Val Phe Asp Thr Gly
 1               5                  10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 112

Gly Ala Asn Val Arg Val Ala Val Phe Asp Thr Gly Leu Ser Glu
 1               5                  10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 113

Val Arg Val Ala Val Phe Asp Thr Gly Leu Ser Glu Lys His Pro
 1               5                  10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 114

Ala Val Phe Asp Thr Gly Leu Ser Glu Lys His Pro His Phe Lys
 1               5                  10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 115

Asp Thr Gly Leu Ser Glu Lys His Pro His Phe Lys Asn Val Lys
 1               5                  10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 116
```

Leu Ser Glu Lys His Pro His Phe Lys Asn Val Lys Glu Arg Thr
 1               5                  10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 117

Lys His Pro His Phe Lys Asn Val Lys Glu Arg Thr Asn Trp Thr
 1               5                  10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 118

His Phe Lys Asn Val Lys Glu Arg Thr Asn Trp Thr Asn Glu Arg
 1               5                  10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 119

Asn Val Lys Glu Arg Thr Asn Trp Thr Asn Glu Arg Thr Leu Asp
 1               5                  10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 120

Glu Arg Thr Asn Trp Thr Asn Glu Arg Thr Leu Asp Asp Gly Leu
 1               5                  10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 121

Asn Trp Thr Asn Glu Arg Thr Leu Asp Asp Gly Leu Gly His Gly
 1               5                  10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 122

-continued

```
Asn Glu Arg Thr Leu Asp Asp Gly Leu Gly His Gly Thr Phe Val
 1               5                  10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 123

Thr Leu Asp Asp Gly Leu Gly His Gly Thr Phe Val Ala Gly Val
 1               5                  10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 124

Asp Gly Leu Gly His Gly Thr Phe Val Ala Gly Val Ile Ala Ser
 1               5                  10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 125

Gly His Gly Thr Phe Val Ala Gly Val Ile Ala Ser Met Arg Glu
 1               5                  10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 126

Thr Phe Val Ala Gly Val Ile Ala Ser Met Arg Glu Cys Gln Gly
 1               5                  10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 127

Ala Gly Val Ile Ala Ser Met Arg Glu Cys Gln Gly Phe Ala Pro
 1               5                  10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 128

Ile Ala Ser Met Arg Glu Cys Gln Gly Phe Ala Pro Asp Ala Glu
```

-continued

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 129

Met Arg Glu Cys Gln Gly Phe Ala Pro Asp Ala Glu Leu His Ile
 1               5                  10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 130

Cys Gln Gly Phe Ala Pro Asp Ala Glu Leu His Ile Phe Arg Val
 1               5                  10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 131

Phe Ala Pro Asp Ala Glu Leu His Ile Phe Arg Val Phe Thr Asn
 1               5                  10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 132

Asp Ala Glu Leu His Ile Phe Arg Val Phe Thr Asn Asn Gln Val
 1               5                  10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 133

Leu His Ile Phe Arg Val Phe Thr Asn Asn Gln Val Ser Tyr Thr
 1               5                  10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 134

Phe Arg Val Phe Thr Asn Asn Gln Val Ser Tyr Thr Ser Trp Phe
 1               5                  10                  15

```
<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 135

Phe Thr Asn Asn Gln Val Ser Tyr Thr Ser Trp Phe Leu Asp Ala
 1               5                  10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 136

Asn Gln Val Ser Tyr Thr Ser Trp Phe Leu Asp Ala Phe Asn Tyr
 1               5                  10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 137

Ser Tyr Thr Ser Trp Phe Leu Asp Ala Phe Asn Tyr Ala Ile Leu
 1               5                  10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 138

Ser Trp Phe Leu Asp Ala Phe Asn Tyr Ala Ile Leu Lys Lys Ile
 1               5                  10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 139

Leu Asp Ala Phe Asn Tyr Ala Ile Leu Lys Lys Ile Asp Val Leu
 1               5                  10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 140

Phe Asn Tyr Ala Ile Leu Lys Lys Ile Asp Val Leu Asn Leu Ser
 1               5                  10                  15
```

```
<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 141

Ala Ile Leu Lys Lys Ile Asp Val Leu Asn Leu Ser Ile Gly Gly
 1               5                  10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 142

Lys Lys Ile Asp Val Leu Asn Leu Ser Ile Gly Gly Pro Asp Phe
 1               5                  10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 143

Asp Val Leu Asn Leu Ser Ile Gly Gly Pro Asp Phe Met Asp His
 1               5                  10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 144

Asn Leu Ser Ile Gly Gly Pro Asp Phe Met Asp His Pro Phe Val
 1               5                  10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 145

Ile Gly Gly Pro Asp Phe Met Asp His Pro Phe Val Asp Lys Val
 1               5                  10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 146

Pro Asp Phe Met Asp His Pro Phe Val Asp Lys Val Trp Glu Leu
 1               5                  10                  15
```

-continued

```
<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 147

Met Asp His Pro Phe Val Asp Lys Val Trp Glu Leu Thr Ala Asn
 1               5                  10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 148

Pro Phe Val Asp Lys Val Trp Glu Leu Thr Ala Asn Asn Val Ile
 1               5                  10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 149

Asp Lys Val Trp Glu Leu Thr Ala Asn Asn Val Ile Met Val Ser
 1               5                  10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 150

Trp Glu Leu Thr Ala Asn Asn Val Ile Met Val Ser Ala Ile Gly
 1               5                  10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 151

Thr Ala Asn Asn Val Ile Met Val Ser Ala Ile Gly Asn Asp Gly
 1               5                  10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 152

Asn Val Ile Met Val Ser Ala Ile Gly Asn Asp Gly Pro Leu Tyr
 1               5                  10                  15

<210> SEQ ID NO 153
```

```
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 153

Met Val Ser Ala Ile Gly Asn Asp Gly Pro Leu Tyr Gly Thr Ile
 1               5                  10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 154

Ala Ile Gly Asn Asp Gly Pro Leu Tyr Gly Thr Leu Asn Asn Pro
 1               5                  10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 155

Asn Asp Gly Pro Leu Tyr Gly Thr Leu Asn Asn Pro Ala Asp Gln
 1               5                  10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 156

Pro Leu Tyr Gly Thr Leu Asn Asn Pro Ala Asp Gln Met Asp Val
 1               5                  10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 157

Gly Thr Leu Asn Asn Pro Ala Asp Gln Met Asp Val Ile Gly Val
 1               5                  10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 158

Asn Asn Pro Ala Asp Gln Met Asp Val Ile Gly Val Gly Gly Ile
 1               5                  10                  15

<210> SEQ ID NO 159
<211> LENGTH: 15
```

```
<212> TYPE: PRT
<213> ORGANISM: Artificial Sequence
<220> FEATURE:
<223> OTHER INFORMATION: Description of Artificial Sequence: Synthetic

<400> SEQUENCE: 159

Ala Asp Gln Met Asp Val Ile Gly Val Gly Gly Ile Asp Phe Glu
 1               5                  10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 160

Met Asp Val Ile Gly Val Gly Gly Ile Asp Phe Glu Asp Asn Ile
 1               5                  10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 161

Ile Gly Val Gly Gly Ile Asp Phe Glu Asp Asn Ile Ala Arg Phe
 1               5                  10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 162

Gly Gly Ile Asp Phe Glu Asp Asn Ile Ala Arg Phe Ser Ser Arg
 1               5                  10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 163

Asp Phe Glu Asp Asn Ile Ala Arg Phe Ser Ser Arg Gly Met Thr
 1               5                  10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 164

Asp Asn Ile Ala Arg Phe Ser Ser Arg Gly Met Thr Thr Trp Glu
 1               5                  10                  15

<210> SEQ ID NO 165
<211> LENGTH: 15
<212> TYPE: PRT
```

<213> ORGANISM: Artificial Sequence
<220> FEATURE:
<223> OTHER INFORMATION: Description of Artificial Sequence: Synthetic

<400> SEQUENCE: 165

Ala Arg Phe Ser Ser Arg Gly Met Thr Thr Trp Glu Leu Pro Gly
 1               5                  10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 166

Ser Ser Arg Gly Met Thr Thr Trp Glu Leu Pro Gly Gly Tyr Gly
 1               5                  10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 167

Gly Met Thr Thr Trp Glu Leu Pro Gly Gly Tyr Gly Arg Met Lys
 1               5                  10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 168

Thr Trp Glu Leu Pro Gly Gly Tyr Gly Arg Met Lys Pro Asp Ile
 1               5                  10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 169

Leu Pro Gly Gly Tyr Gly Arg Met Lys Pro Asp Ile Val Thr Tyr
 1               5                  10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 170

Gly Tyr Gly Arg Met Lys Pro Asp Ile Val Thr Tyr Gly Ala Gly
 1               5                  10                  15

<210> SEQ ID NO 171
<211> LENGTH: 15
<212> TYPE: PRT
<213> ORGANISM: Artificial Sequence

```
<220> FEATURE:
<223> OTHER INFORMATION: Description of Artificial Sequence: Synthetic

<400> SEQUENCE: 171

Arg Met Lys Pro Asp Ile Val Thr Tyr Gly Ala Gly Val Arg Gly
 1               5                  10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 172

Pro Asp Ile Val Thr Tyr Gly Ala Gly Val Arg Gly Ser Gly Val
 1               5                  10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 173

Val Thr Tyr Gly Ala Gly Val Arg Gly Ser Gly Val Lys Gly Gly
 1               5                  10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 174

Gly Ala Gly Val Arg Gly Ser Gly Val Lys Gly Gly Cys Arg Ala
 1               5                  10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 175

Val Arg Gly Ser Gly Val Lys Gly Gly Cys Arg Ala Leu Ser Gly
 1               5                  10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 176

Ser Gly Val Lys Gly Gly Cys Arg Ala Leu Ser Gly Thr Ser Val
 1               5                  10                  15

<210> SEQ ID NO 177
<211> LENGTH: 15
<212> TYPE: PRT
<213> ORGANISM: Artificial Sequence
<220> FEATURE:
```

-continued

```
<223> OTHER INFORMATION: Description of Artificial Sequence: Synthetic

<400> SEQUENCE: 177

Lys Gly Gly Cys Arg Ala Leu Ser Gly Thr Ser Val Ala Ser Pro
 1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 178

Cys Arg Ala Leu Ser Gly Thr Ser Val Ala Ser Pro Val Val Ala
 1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 179

Leu Ser Gly Thr Ser Val Ala Ser Pro Val Val Ala Gly Ala Val
 1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 180

Thr Ser Val Ala Ser Pro Val Val Ala Gly Ala Val Thr Leu Leu
 1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 181

Ala Ser Pro Val Val Ala Gly Ala Val Thr Leu Leu Val Ser Thr
 1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 182

Val Val Ala Gly Ala Val Thr Leu Leu Val Ser Thr Val Gln Lys
 1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

<400> SEQUENCE: 183

Gly Ala Val Thr Leu Leu Val Ser Thr Val Gln Lys Arg Glu Leu
 1               5                  10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 184

Thr Leu Leu Val Ser Thr Val Gln Lys Arg Glu Leu Val Asn Pro
 1               5                  10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 185

Val Ser Thr Val Gln Lys Arg Glu Leu Val Asn Pro Ala Ser Met
 1               5                  10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 186

Val Gln Lys Arg Glu Leu Val Asn Pro Ala Ser Met Lys Gln Ala
 1               5                  10                  15

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 187

Arg Glu Leu Val Asn Pro Ala Ser Met Lys Gln Ala Leu Ile Ala
 1               5                  10                  15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 188

Val Asn Pro Ala Ser Met Lys Gln Ala Leu Ile Ala Ser Ala Arg
 1               5                  10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic

```
<400> SEQUENCE: 189

Ala Ser Met Lys Gln Ala Leu Ile Ala Ser Ala Arg Arg Leu Pro
 1               5                  10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 190

Lys Gln Ala Leu Ile Ala Ser Ala Arg Arg Leu Pro Gly Val Asn
 1               5                  10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 191

Leu Ile Ala Ser Ala Arg Arg Leu Pro Gly Val Asn Met Phe Glu
 1               5                  10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 192

Ser Ala Arg Arg Leu Pro Gly Val Asn Met Phe Glu Gln Gly His
 1               5                  10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 193

Arg Leu Pro Gly Val Asn Met Phe Glu Gln Gly His Gly Lys Leu
 1               5                  10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 194

Gly Val Asn Met Phe Glu Gln Gly His Gly Lys Leu Asp Leu Leu
 1               5                  10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 195
```

```
Met Phe Glu Gln Gly His Gly Lys Leu Asp Leu Leu Arg Ala Tyr
 1               5                  10                  15
```

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 196

```
Gln Gly His Gly Lys Leu Asp Leu Leu Arg Ala Tyr Gln Ile Leu
 1               5                  10                  15
```

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 197

```
Gly Lys Leu Asp Leu Leu Arg Ala Tyr Gln Ile Leu Asn Ser Tyr
 1               5                  10                  15
```

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 198

```
Asp Leu Leu Arg Ala Tyr Gln Ile Leu Asn Ser Tyr Lys Pro Gln
 1               5                  10                  15
```

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 199

```
Arg Ala Tyr Gln Ile Leu Asn Ser Tyr Lys Pro Gln Ala Ser Leu
 1               5                  10                  15
```

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 200

```
Gln Ile Leu Asn Ser Tyr Lys Pro Gln Ala Ser Leu Ser Pro Ser
 1               5                  10                  15
```

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 201

```
Asn Ser Tyr Lys Pro Gln Ala Ser Leu Ser Pro Ser Tyr Ile Asp
  1               5                  10                  15
```

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 202

```
Lys Pro Gln Ala Ser Leu Ser Pro Ser Tyr Ile Asp Leu Thr Glu
  1               5                  10                  15
```

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 203

```
Ala Ser Leu Ser Pro Ser Tyr Ile Asp Leu Thr Glu Cys Pro Tyr
  1               5                  10                  15
```

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 204

```
Ser Pro Ser Tyr Ile Asp Leu Thr Glu Cys Pro Tyr Met Trp Pro
  1               5                  10                  15
```

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 205

```
Tyr Ile Asp Leu Thr Glu Cys Pro Tyr Met Trp Pro Tyr Cys Ser
  1               5                  10                  15
```

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 206

```
Leu Thr Glu Cys Pro Tyr Met Trp Pro Tyr Cys Ser Gln Pro Ile
  1               5                  10                  15
```

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 207

```
Cys Pro Tyr Met Trp Pro Tyr Cys Ser Gln Pro Ile Tyr Tyr Gly
```

-continued

<210> SEQ ID NO 208
<211> LENGTH: 1052
<212> TYPE: PRT
<213> ORGANISM: Homo sapiens

<400> SEQUENCE: 208

```
Met Lys Leu Val Asn Ile Trp Leu Leu Leu Val Leu Leu Cys
 1               5                  10                  15

Gly Lys Lys His Leu Gly Asp Arg Leu Glu Lys Lys Ser Phe Glu Lys
                20                  25                  30

Ala Pro Cys Pro Gly Cys Ser His Leu Thr Leu Lys Val Glu Phe Ser
            35                  40                  45

Ser Thr Val Val Glu Tyr Glu Tyr Ile Val Ala Phe Asn Gly Tyr Phe
        50                  55                  60

Thr Ala Lys Ala Arg Asn Ser Phe Ile Ser Ser Ala Leu Lys Ser Ser
 65                  70                  75                  80

Glu Val Asp Asn Trp Arg Ile Ile Pro Arg Asn Asn Pro Ser Ser Asp
                 85                  90                  95

Tyr Pro Ser Asp Phe Glu Val Ile Gln Ile Lys Glu Lys Gln Lys Ala
            100                 105                 110

Gly Leu Leu Thr Leu Glu Asp His Pro Asn Ile Lys Arg Val Thr Pro
        115                 120                 125

Gln Arg Lys Val Phe Arg Ser Leu Lys Tyr Ala Glu Ser Asp Pro Thr
    130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
            180                 185                 190

Val Ala Gln Thr Leu Gln Ala Asp Val Leu Trp Gln Met Gly Tyr Thr
        195                 200                 205

Gly Ala Asn Val Arg Val Ala Val Phe Asp Thr Gly Leu Ser Glu Lys
    210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
                245                 250                 255

Ile Ala Ser Met Arg Glu Cys Gln Gly Phe Ala Pro Asp Ala Glu Leu
            260                 265                 270

His Ile Phe Arg Val Phe Thr Asn Asn Gln Val Ser Tyr Thr Ser Trp
        275                 280                 285

Phe Leu Asp Ala Phe Asn Tyr Ala Ile Leu Lys Lys Ile Asp Val Leu
    290                 295                 300

Asn Leu Ser Ile Gly Gly Pro Asp Phe Met Asp His Pro Phe Val Asp
305                 310                 315                 320

Lys Val Trp Glu Leu Thr Ala Asn Asn Val Ile Met Val Ser Ala Ile
                325                 330                 335

Gly Asn Asp Gly Pro Leu Tyr Gly Thr Leu Asn Asn Pro Ala Asp Gln
            340                 345                 350

Met Asp Val Ile Gly Val Gly Gly Ile Asp Phe Glu Asp Asn Ile Ala
        355                 360                 365
```

```
Arg Phe Ser Ser Arg Gly Met Thr Thr Trp Glu Leu Pro Gly Gly Tyr
    370                 375                 380
Gly Arg Met Lys Pro Asp Ile Val Thr Tyr Gly Ala Gly Val Arg Gly
385                 390                 395                 400
Ser Gly Val Lys Gly Gly Cys Arg Ala Leu Ser Gly Thr Ser Val Ala
                405                 410                 415
Ser Pro Val Val Ala Gly Ala Val Thr Leu Leu Val Ser Thr Val Gln
            420                 425                 430
Lys Arg Glu Leu Val Asn Pro Ala Ser Met Lys Gln Ala Leu Ile Ala
        435                 440                 445
Ser Ala Arg Arg Leu Pro Gly Val Asn Met Phe Glu Gln Gly His Gly
    450                 455                 460
Lys Leu Asp Leu Leu Arg Ala Tyr Gln Ile Leu Asn Ser Tyr Lys Pro
465                 470                 475                 480
Gln Ala Ser Leu Ser Pro Ser Tyr Ile Asp Leu Thr Glu Cys Pro Tyr
                485                 490                 495
Met Trp Pro Tyr Cys Ser Gln Pro Ile Tyr Tyr Gly Gly Met Pro Thr
            500                 505                 510
Val Val Asn Val Thr Ile Leu Asn Gly Met Gly Val Thr Gly Arg Ile
        515                 520                 525
Val Asp Lys Pro Asp Trp Gln Pro Tyr Leu Pro Gln Asn Gly Asp Asn
530                 535                 540
Ile Glu Val Ala Phe Ser Tyr Ser Ser Val Leu Trp Pro Trp Ser Gly
545                 550                 555                 560
Tyr Leu Ala Ile Ser Ile Ser Val Thr Lys Lys Ala Ala Ser Trp Glu
                565                 570                 575
Gly Ile Ala Gln Gly His Val Met Ile Thr Val Ala Ser Pro Ala Glu
            580                 585                 590
Thr Glu Ser Lys Asn Gly Ala Glu Gln Thr Ser Thr Val Lys Leu Pro
        595                 600                 605
Ile Lys Val Lys Ile Ile Pro Thr Pro Arg Ser Lys Arg Val Leu
    610                 615                 620
Trp Asp Gln Tyr His Asn Leu Arg Tyr Pro Pro Gly Tyr Phe Pro Arg
625                 630                 635                 640
Asp Asn Leu Arg Met Lys Asn Asp Pro Leu Asp Trp Asn Gly Asp His
                645                 650                 655
Ile His Thr Asn Phe Arg Asp Met Tyr Gln His Leu Arg Ser Met Gly
            660                 665                 670
Tyr Phe Val Glu Val Leu Gly Ala Pro Phe Thr Cys Phe Asp Ala Ser
        675                 680                 685
Gln Tyr Gly Thr Leu Leu Met Val Asp Ser Glu Glu Tyr Phe Pro
    690                 695                 700
Glu Glu Ile Ala Lys Leu Arg Arg Asp Val Asp Asn Gly Leu Ser Leu
705                 710                 715                 720
Val Ile Phe Ser Asp Trp Tyr Asn Thr Ser Val Met Arg Lys Val Lys
                725                 730                 735
Phe Tyr Asp Glu Asn Thr Arg Gln Trp Trp Met Pro Asp Thr Gly Gly
            740                 745                 750
Ala Asn Ile Pro Ala Leu Asn Glu Leu Leu Ser Val Trp Asn Met Gly
        755                 760                 765
Phe Ser Asp Gly Leu Tyr Glu Gly Glu Phe Thr Leu Ala Asn His Asp
    770                 775                 780
Met Tyr Tyr Ala Ser Gly Cys Ser Ile Ala Lys Phe Pro Glu Asp Gly
```

```
                785                 790                 795                 800
Val Val Ile Thr Gln Thr Phe Lys Asp Gln Gly Leu Glu Val Leu Lys
                    805                 810                 815
Gln Glu Thr Ala Val Val Glu Asn Val Pro Ile Leu Gly Leu Tyr Gln
                820                 825                 830
Ile Pro Ala Glu Gly Gly Arg Ile Val Leu Tyr Gly Asp Ser Asn
                835                 840                 845
Cys Leu Asp Asp Ser His Arg Gln Lys Asp Cys Phe Trp Leu Leu Asp
        850                 855                 860
Ala Leu Leu Gln Tyr Thr Ser Tyr Gly Val Thr Pro Pro Ser Leu Ser
865                 870                 875                 880
His Ser Gly Asn Arg Gln Arg Pro Ser Gly Ala Gly Ser Val Thr
                    885                 890                 895
Pro Glu Arg Met Glu Gly Asn His Leu His Arg Tyr Ser Lys Val Leu
                900                 905                 910
Glu Ala His Leu Gly Asp Pro Lys Pro Arg Pro Leu Pro Ala Cys Pro
            915                 920                 925
Arg Leu Ser Trp Ala Lys Pro Gln Pro Leu Asn Glu Thr Ala Pro Ser
            930                 935                 940
Asn Leu Trp Lys His Gln Lys Leu Leu Ser Ile Asp Leu Asp Lys Val
945                 950                 955                 960
Val Leu Pro Asn Phe Arg Ser Asn Arg Pro Gln Val Arg Pro Leu Ser
                965                 970                 975
Pro Gly Glu Ser Gly Ala Trp Asp Ile Pro Gly Gly Ile Met Pro Gly
            980                 985                 990
Arg Tyr Asn Gln Glu Val Gly Gln Thr Ile Pro Val Phe Ala Phe Leu
            995                 1000                1005
Gly Ala Met Val Val Leu Ala Phe Phe Val Val Gln Ile Asn Lys Ala
        1010                1015                1020
Lys Ser Arg Pro Lys Arg Arg Lys Pro Arg Val Lys Arg Pro Gln Leu
1025                1030                1035                1040
Met Gln Gln Val His Pro Pro Lys Thr Pro Ser Val
                1045                1050

<210> SEQ ID NO 209
<211> LENGTH: 280
<212> TYPE: PRT
<213> ORGANISM: Homo sapiens

<400> SEQUENCE: 209

Arg Ala Ile Pro Arg Gln Val Ala Gln Thr Leu Gln Ala Asp Val Leu
1               5                   10                  15
Trp Gln Met Gly Tyr Thr Gly Ala Asn Val Arg Val Ala Val Phe Asp
                20                  25                  30
Thr Gly Leu Ser Glu Lys His Pro His Phe Lys Asn Val Lys Glu Arg
            35                  40                  45
Thr Asn Trp Thr Asn Glu Arg Thr Leu Asp Asp Gly Leu Gly His Gly
        50                  55                  60
Thr Phe Val Ala Gly Val Ile Ala Ser Met Arg Glu Cys Gln Gly Phe
65                  70                  75                  80
Ala Pro Asp Ala Glu Leu His Ile Phe Arg Val Phe Thr Asn Asn Gln
                85                  90                  95
Val Ser Tyr Thr Ser Trp Phe Leu Asp Ala Phe Asn Tyr Ala Ile Leu
                100                 105                 110
```

```
Lys Lys Ile Asp Val Leu Asn Leu Ser Ile Gly Gly Pro Asp Phe Met
        115                 120                 125

Asp His Pro Phe Val Asp Lys Val Trp Glu Leu Thr Ala Asn Asn Val
        130                 135                 140

Ile Met Val Ser Ala Ile Gly Asn Asp Gly Pro Leu Tyr Gly Thr Leu
145                 150                 155                 160

Asn Asn Pro Ala Asp Gln Met Asp Val Ile Gly Val Gly Ile Asp
                165                 170                 175

Phe Glu Asp Asn Ile Ala Arg Phe Ser Ser Arg Gly Met Thr Thr Trp
            180                 185                 190

Glu Leu Pro Gly Gly Tyr Gly Arg Met Lys Pro Asp Ile Val Thr Tyr
        195                 200                 205

Gly Ala Gly Val Arg Gly Ser Gly Val Lys Gly Gly Cys Arg Ala Leu
    210                 215                 220

Ser Gly Thr Ser Val Ala Ser Pro Val Val Ala Gly Ala Val Thr Leu
225                 230                 235                 240

Leu Val Ser Thr Val Gln Lys Arg Glu Leu Val Asn Pro Ala Ser Met
                245                 250                 255

Lys Gln Ala Leu Ile Ala Ser Ala Arg Arg Leu Pro Gly Val Asn Met
                260                 265                 270

Phe Glu Gln Gly His Gly Lys Leu
        275                 280

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 210

Gly Ser Ile Ser Tyr Pro Ala Arg Tyr Ala Asn Ala Met Ala Val
  1               5                  10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 211

Ala Ser Ile Ser Tyr Pro Ala Arg Tyr Ala Asn Ala Met Ala Val
  1               5                  10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 212

Gly Ala Ile Ser Tyr Pro Ala Arg Tyr Ala Asn Ala Met Ala Val
  1               5                  10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
```

<400> SEQUENCE: 213

Gly Ser Ala Ser Tyr Pro Ala Arg Tyr Ala Asn Ala Met Ala Val
 1               5                  10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 214

Gly Ser Ile Ala Tyr Pro Ala Arg Tyr Ala Asn Ala Met Ala Val
 1               5                  10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 215

Gly Ser Ile Ser Ala Pro Ala Arg Tyr Ala Asn Ala Met Ala Val
 1               5                  10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 216

Gly Ser Ile Ser Tyr Ala Ala Arg Tyr Ala Asn Ala Met Ala Val
 1               5                  10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 217

Gly Ser Ile Ser Tyr Pro Ala Ala Tyr Ala Asn Ala Met Ala Val
 1               5                  10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 218

Gly Ser Ile Ser Tyr Pro Ala Arg Ala Ala Asn Ala Met Ala Val
 1               5                  10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic

```
-continued

<400> SEQUENCE: 219

Gly Ser Ile Ser Tyr Pro Ala Arg Tyr Ala Ala Ala Met Ala Val
 1               5                  10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 220

Gly Ser Ile Ser Tyr Pro Ala Arg Tyr Ala Asn Ala Ala Ala Val
 1               5                  10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 221

Gly Ser Ile Ser Tyr Pro Ala Arg Tyr Ala Asn Ala Met Ala Ala
 1               5                  10                  15

<210> SEQ ID NO 222
<211> LENGTH: 15
<212> TYPE: PRT
<213> ORGANISM: Humicola insolens

<400> SEQUENCE: 222

Pro Gly Gly Val Ala Tyr Ser Cys Ala Asp Gln Thr Pro Trp Ala
 1               5                  10                  15

<210> SEQ ID NO 223
<211> LENGTH: 15
<212> TYPE: PRT
<213> ORGANISM: Humicola insolens

<400> SEQUENCE: 223

Cys Gly Trp Ala Lys Lys Ala Pro Val Asn Gln Pro Val Phe Ser
 1               5                  10                  15

<210> SEQ ID NO 224
<211> LENGTH: 276
<212> TYPE: PRT
<213> ORGANISM: Humicola insolens

<400> SEQUENCE: 224

Met Arg Ser Ser Pro Leu Leu Pro Ser Ala Val Val Ala Ala Leu Pro
 1               5                  10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95
```

```
Ser Ile Ala Gly Ser Asn Glu Ala Gly Trp Cys Cys Ala Cys Tyr Glu
                100                 105                 110

Leu Thr Phe Thr Ser Gly Pro Val Ala Gly Lys Lys Met Val Val Gln
            115                 120                 125

Ser Thr Ser Thr Gly Gly Asp Leu Gly Ser Asn His Phe Asp Leu Asn
        130                 135                 140

Ile Pro Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln
        275

<210> SEQ ID NO 225
<211> LENGTH: 18
<212> TYPE: PRT
<213> ORGANISM: Thermomyces lanuginosus

<400> SEQUENCE: 225

Gly Asp Val Thr Gly Phe Leu Ala Leu Asp Asn Thr Asn Lys Leu Ile
1               5                   10                  15

Val Leu

<210> SEQ ID NO 226
<211> LENGTH: 15
<212> TYPE: PRT
<213> ORGANISM: Thermomyces lanuginosus

<400> SEQUENCE: 226

Ser Ile Glu Asn Trp Ile Gly Asn Leu Asn Phe Asp Leu Lys Glu
1               5                   10                  15

<210> SEQ ID NO 227
<211> LENGTH: 291
<212> TYPE: PRT
<213> ORGANISM: Thermomyces lanuginosus

<400> SEQUENCE: 227

Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60
```

-continued

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
130                 135                 140

Thr Leu Arg Gln Lys Val Glu Asp Ala Val Arg Glu His Pro Asp Tyr
145                 150                 155                 160

Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
        275                 280                 285

Thr Cys Leu
    290

<210> SEQ ID NO 228
<211> LENGTH: 15
<212> TYPE: PRT
<213> ORGANISM: Streptomyces plicatus

<400> SEQUENCE: 228

Ile Lys Val Leu Leu Ser Val Leu Gly Asn His Gln Gly Ala Gly
1               5                   10                  15

<210> SEQ ID NO 229
<211> LENGTH: 313
<212> TYPE: PRT
<213> ORGANISM: Streptomyces plicatus

<400> SEQUENCE: 229

Met Phe Thr Pro Val Arg Arg Val Arg Thr Ala Ala Leu Ala Leu
1               5                   10                  15

Ser Ala Ala Ala Leu Val Leu Gly Ser Thr Ala Ala Ser Gly Ala
            20                  25                  30

Ser Ala Thr Pro Ser Pro Ala Pro Ala Pro Ala Pro Val Lys
        35                  40                  45

Gln Gly Pro Thr Ser Val Ala Tyr Val Glu Val Asn Asn Asn Ser Met
    50                  55                  60

Leu Asn Val Gly Lys Tyr Thr Leu Ala Asp Gly Gly Asn Ala Phe
65                  70                  75                  80

-continued

```
Asp Val Ala Val Ile Phe Ala Ala Asn Ile Asn Tyr Asp Thr Gly Thr
                 85                  90                  95

Lys Thr Ala Tyr Leu His Phe Asn Glu Asn Val Gln Arg Val Leu Asp
            100                 105                 110

Asn Ala Val Thr Gln Ile Arg Pro Leu Gln Gln Gln Gly Ile Lys Val
        115                 120                 125

Leu Leu Ser Val Leu Gly Asn His Gln Gly Ala Gly Phe Ala Asn Phe
    130                 135                 140

Pro Ser Gln Gln Ala Ala Ser Ala Phe Ala Lys Gln Leu Ser Asp Ala
145                 150                 155                 160

Val Ala Lys Tyr Gly Leu Asp Gly Val Asp Phe Asp Asp Glu Tyr Ala
                165                 170                 175

Glu Tyr Gly Asn Asn Gly Thr Ala Gln Pro Asn Asp Ser Ser Phe Val
                180                 185                 190

His Leu Val Thr Ala Leu Arg Ala Asn Met Pro Asp Lys Ile Ile Ser
            195                 200                 205

Leu Tyr Asn Ile Gly Pro Ala Ala Ser Arg Leu Ser Tyr Gly Gly Val
    210                 215                 220

Asp Val Ser Asp Lys Phe Asp Tyr Ala Trp Asn Pro Tyr Tyr Gly Thr
225                 230                 235                 240

Trp Gln Val Pro Gly Ile Ala Leu Pro Lys Ala Gln Leu Ser Pro Ala
                245                 250                 255

Ala Val Glu Ile Gly Arg Thr Ser Arg Ser Thr Val Ala Asp Leu Ala
            260                 265                 270

Arg Arg Thr Val Asp Glu Gly Tyr Gly Val Tyr Leu Thr Tyr Asn Leu
        275                 280                 285

Asp Gly Gly Asp Arg Thr Ala Asp Val Ser Ala Phe Thr Arg Glu Leu
    290                 295                 300

Tyr Gly Ser Glu Ala Val Arg Thr Pro
305                 310

<210> SEQ ID NO 230
<211> LENGTH: 15
<212> TYPE: PRT
<213> ORGANISM: Bacillus amyloliquefaciens

<400> SEQUENCE: 230

Gly Thr Val Ala Ala Leu Asn Asn Ser Ile Gly Val Leu Gly Val
1               5                   10                  15

<210> SEQ ID NO 231
<211> LENGTH: 15
<212> TYPE: PRT
<213> ORGANISM: Bacillus amyloliquefaciens

<400> SEQUENCE: 231

Asn Gly Ile Glu Trp Ala Ile Ala Asn Asn Met Asp Val Ile Asn
1               5                   10                  15

<210> SEQ ID NO 232
<211> LENGTH: 15
<212> TYPE: PRT
<213> ORGANISM: Bacillus lentus

<400> SEQUENCE: 232

Thr Gly Ser Gly Val Lys Val Ala Val Leu Asp Thr Gly Ile Ser
1               5                   10                  15
```

<210> SEQ ID NO 233
<211> LENGTH: 15
<212> TYPE: PRT
<213> ORGANISM: Bacillus lentus

<400> SEQUENCE: 233

Ser Ala Glu Leu Tyr Ala Val Lys Val Leu Gly Ala Ser Gly Ser
1 5 10 15

<210> SEQ ID NO 234
<211> LENGTH: 17
<212> TYPE: PRT
<213> ORGANISM: Bacillus lentus

<400> SEQUENCE: 234

Gly Ser Ile Ser Tyr Pro Ala Arg Tyr Ala Asn Ala Met Ala Val Gly
1 5 10 15

Ala

<210> SEQ ID NO 235
<211> LENGTH: 15
<212> TYPE: PRT
<213> ORGANISM: Bacillus lentus

<400> SEQUENCE: 235

Gly Ala Gly Leu Asp Ile Val Ala Pro Gly Val Asn Val Gln Ser
1 5 10 15

<210> SEQ ID NO 236
<211> LENGTH: 272
<212> TYPE: PRT
<213> ORGANISM: Artificial Sequence
<220> FEATURE:
<223> OTHER INFORMATION: Description of Artificial Sequence: Hybrid of Bacillus lentus and Bacillus amyloliquefaciens

<400> SEQUENCE: 236

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Asn Asn Gly Met His Val Ile Asn Met Ser Leu Gly Gly Ser Gly
115 120 125

Ser Ala Ala Leu Lys Ala Ala Val Asp Lys Ala Val Ala Ser Gly Val
130 135 140

Val Val Val Ala Ala Ala Gly Asn Glu Gly Thr Ser Gly Ser Ser Ser
145 150 155 160

Thr Val Gly Tyr Pro Gly Lys Tyr Pro Ser Val Ile Ala Val Gly Ala
165 170 175

-continued

```
Val Asp Ser Ser Asn Gln Arg Ala Ser Phe Ser Ser Val Gly Pro Glu
            180                 185                 190

Leu Asp Val Met Ala Pro Gly Val Ser Ile Gln Ser Thr Leu Pro Gly
            195                 200                 205

Asn Lys Tyr Gly Ala Tyr Asn Gly Thr Ser Met Ala Ser Pro His Val
        210                 215                 220

Ala Gly Ala Ala Ala Leu Ile Leu Ser Lys His Pro Asn Trp Thr Asn
225                 230                 235                 240

Thr Gln Val Arg Ser Ser Leu Glu Asn Thr Thr Thr Lys Leu Gly Asp
                245                 250                 255

Ser Phe Tyr Tyr Gly Lys Gly Leu Ile Asn Val Gln Ala Ala Ala Gln
            260                 265                 270

<210> SEQ ID NO 237
<211> LENGTH: 15
<212> TYPE: PRT
<213> ORGANISM: Bacillus lentis subtilisin

<400> SEQUENCE: 237

Ile Ala Ala Leu Asn Asn Ser Ile Gly Val Leu Gly Val Ala Pro
1               5                   10                  15

<210> SEQ ID NO 238
<211> LENGTH: 18
<212> TYPE: PRT
<213> ORGANISM: Bacillus lentis subtilisin

<400> SEQUENCE: 238

Leu Glu Trp Ala Gly Asn Asn Gly Met His Val Ala Asn Leu Ser Leu
1               5                   10                  15

Gly Ser

<210> SEQ ID NO 239
<211> LENGTH: 15
<212> TYPE: PRT
<213> ORGANISM: Bacillus amyloliquefaciens subtilisin

<400> SEQUENCE: 239

Val Ala Ala Leu Asn Asn Ser Ile Gly Val Leu Gly Val Ala Pro
1               5                   10                  15

<210> SEQ ID NO 240
<211> LENGTH: 17
<212> TYPE: PRT
<213> ORGANISM: Bacillus amyloliquefaciens subtilisin

<400> SEQUENCE: 240

Ile Glu Trp Ala Ile Ala Asn Asn Met Asp Val Ile Asn Met Ser Leu
1               5                   10                  15

Gly
```

PROTEINS PRODUCING AN ALTERED IMMUNOGENIC RESPONSE AND METHODS OF MAKING AND USING THE SAME

CROSS-REFERENCE TO RELATED APPLICATIONS

The present application is a Continuation-in-Part of U.S. patent application Ser. No. 09/500,135, filed Feb. 8, 2000 (now U.S. Pat. No. 6,838,269), which is a Continuation-in-Part of U.S. patent application Ser. No. 09/060,872, filed Apr. 15, 1998 (now U.S. Pat. No. 6,835,550). The present application is also related to U.S. patent application Ser. No. 09/255,502 (now U.S. Pat. No. 6,218,165), Ser. No. 09/255,505 (now abandoned), and Ser. No. 09/255,501 (now U.S. Pat. No. 6,596,525), all of which were filed Feb. 23, 1999, and are Divisionals of U.S. patent application Ser. No. 09/060,872, filed Apr. 15, 1998.

BACKGROUND OF THE INVENTION

Proteins used in industrial, pharmaceutical and commercial applications are of increasing prevalence. As a result, the increased exposure due to this prevalence has been responsible for some safety hazards caused by the sensitization of certain persons to those peptides, whereupon subsequent exposure causes extreme allergic reactions which can be injurious and even fatal. For example, proteases are known to cause dangerous hypersensitivity in some individuals. As a result, despite the usefulness of proteases in industry, e.g., in laundry detergents, cosmetics, textile treatment etc., and the extensive research performed in the field to provide improved proteases which have, for example, more effective stain removal under detergency conditions; the use of proteases in industry has been problematic due to their ability to produce a hypersensitive allergenic response in some humans.

Much work has been done to alleviate these problems. Among the strategies explored to reduce immunogenic potential of protease use have been improved production processes which reduce potential contact by controlling and minimizing workplace concentrations of dust particles or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of protease, per se, have been relatively unsuccessful. Alternatively, efforts have been made to mask epitopes in protease which are recognized by immunoglobulin E (IgE) in hypersensitive individuals (PCT Publication No. WO 92/10755) or to enlarge or change the nature of the antigenic determinants by attaching polymers or peptides/proteins to the problematic protease.

When an adaptive immune response occurs in an exaggerated or inappropriate form, the individual experiencing the reaction is said to be hypersensitive. Hypersensitivity reactions are the result of normally beneficial immune responses acting inappropriately and sometimes cause inflammatory reactions and tissue damage. They can be provoked by many antigens; and the cause of a hypersensitivity reaction will vary from one individual to the next. Hypersensitivity does not normally manifest itself upon first contact with the antigen, but usually appears upon subsequent contact. One form of hypersensitivity occurs when an IgE response is directed against innocuous environmental antigens, such as pollen, dust-mites or animal dander. The resulting release of pharmacological mediators by IgE-sensitized mast cells produces an acute inflammatory reaction with symptoms such as asthma or rhinitis.

Nonetheless, a strategy comprising modifying the IgE sites will not generally be successful in preventing the cause of the initial sensitization reaction. Accordingly, such strategies, while perhaps neutralizing or reducing the severity of the subsequent hypersensitivity reaction, will not reduce the number or persons actually sensitized. For example, when a person is known to be hypersensitive to a certain antigen, the general, and only safe, manner of dealing with such a situation is to isolate the hypersensitive person from the antigen as completely as possible. Indeed, any other course of action would be dangerous to the health of the hypersensitive individual. Thus, while reducing the danger of a specific protein for a hypersensitive individual is important, for industrial purposes it would be far more valuable to render a protein incapable of initiating the hypersensitivity reaction in the first place.

T-lymphocytes (T-cells)-are key players in the induction and regulation of immune responses and in the execution of immunological effector functions. Specific immunity against infectious agents and tumors is known to be dependent on these cells and they are believed to contribute to the healing of injuries. On the other hand, failure to control these responses can lead to auto aggression. In general, antigen is presented to T-cells in the form of antigen presenting cells which, through a variety of cell surface mechanisms, capture and display antigen or partial antigen in a manner suitable for antigen recognition by the T-cell. Upon recognition of a specific epitope by the receptors on the surface of the T-cells (T-cell receptors), the T-cells begin a series of complex interactions, including proliferation, which result in the production of antibody by B-cells. While T-cells and B-cells are both activated by antigenic epitopes which exist on a given protein or peptide, the actual epitopes recognized by these mononuclear cells are generally not identical. In fact, the epitope which activates a T-cell to initiate the creation of immunologic diversity is quite often not the same epitope which is later recognized by B-cells in the course of the immunologic response. Thus, with respect to hypersensitivity, while the specific antigenic interaction between the T-cell and the antigen is a critical element in the initiation of the immune response to antigenic exposure, the specifics of that interaction, i.e., the epitope recognized, is often not relevant to subsequent development of a full blown allergic reaction.

PCT Publication No. WO 96/40791 discloses a process for producing polyalkylene oxide-polypeptide conjugates with reduced allergenicity using polyalkylene oxide as a starting material.

PCT Publication No. WO 97/30148 discloses a polypeptide conjugate with reduced allergenicity which comprises one polymeric carrier molecule having two or more polypeptide molecules coupled covalently thereto.

PCT Publication No. WO 96/17929 discloses a process for producing polypeptides with reduced allergenicity comprising the step of conjugating from 1 to 30 polymolecules to a parent polypeptide.

PCT Publication No. WO 92/10755 discloses a method of producing protein variants evoking a reduced immunogenic response in animals. In this application, the proteins of interest, a series of proteases and variants thereof, were used to immunize rats. The sera from the rats was then used to measure the reactivity of the polyclonal antibodies already produced and present in the immunized sera to the protein of interest and variants thereof. From these results, it was possible to determine whether the antibodies in the preparation were comparatively more or less reactive with the protein and its variants, thus permitting an analysis of which changes in the protein are likely to neutralize or reduce the ability of the Ig to bind. From these tests on rats, the conclusion was arrived at that changing any of subtilisin 309 residues corresponding to 127, 128, 129, 130, 131, 151, 136, 151, 152, 153, 154, 161, 162, 163, 167, 168, 169, 170, 171, 172, 173, 174, 175, 176, 186, 193, 194, 195, 196, 197, 247, 251, 261 will result in a change in the immunological potential.

PCT Publication No. WO 94/10191 discloses low allergenic proteins comprising oligomeric forms of the parent monomeric protein, wherein the oligomer has substantially retained its activity.

While some studies have provided methods of reducing the allergenicity of certain proteins and identification of epitopes which cause allergic reactions in some individuals, the assays used to identify these epitopes generally involve measurement of IgE and IgG antibody in blood sera previously exposed to the antigen. However, once an Ig reaction has been initiated, sensitization has already occurred. Accordingly, there is a need for a method of determining epitopes which cause sensitization in the first place, as neutralization of these epitopes will result in significantly less possibility for sensitization to occur, thus reducing the possibility of initial sensitization. There is also a need to produce proteins which produce an enhanced immunogenic response, and a need to identify naturally occurring proteins which produce a low immunogenic response. This invention meets these and other needs.

SUMMARY OF THE INVENTION

The present invention provides proteins which produce immunogenic responses as desired, methods of identifying and making such proteins, and methods of using such proteins. For example, as will be become apparent from the detailed description below, the methods and compositions provided herein are useful in forming hyper- and hypo-allergenic compositions. As used herein, hyper and hypo means the composition produces a greater or lesser immunogenic response, respectively, than the same composition without the proteins of the present invention. Such compositions may include cleaning compositions, textile treatments, contact lens cleaning solutions or products, peptide hydrolysis products, waste treatment products, cosmetic formulations including for skin, hair and oral care, pharmaceuticals such as blood clot removal products, research products such as enzymes and therapeutics including vaccines.

In one aspect of the invention, a polypeptide of interest is selected and provided herein. The polypeptide of interest is preferably one having a T-cell epitope and is then varied as described below. However, polypeptides of interest may also be selected based on naturally occuring properties and not altered. Moreover, polypeptides of interest may be selected which do not have a T-cell epitope, and altered so as to have a T-cell epitope.

In one aspect of the invention provided herein is a variant of a polypeptide of interest comprising a T-cell epitope. The variant differs from the polypeptide of interest by having an altered T-cell epitope such that said variant and said polypeptide produce different immunogenic responses in an individual. The variant can be prepared and selected to produce either a greater or lesser immunogenic response than said polypeptide of interest.

The polypeptide of interest can be any polypeptide of interest. In one aspect, the polypeptide is selected from the group consisting of enzymes, hormones, factors, vaccines and cytokines. In one embodiment, the polypeptide of interest is not recognized by said individual as endogenous to said individual, or not recognized as "self". As indicated herein, the polypeptide of interest may be an enzyme. In one embodiment, the enzyme is selected from the group consisting of lipase, cellulase, endo-glucosidase H, protease, carbohydrase, reductase, oxidase, isomerase, transferase, kinase and phosphatase. In preferred embodiments, the polypeptide of interest and the variant of said polypeptide of interest each comprise at least some of the same activity. For example, if a variant of a protease is provided, said variant will produce an altered immunogenic response, but will retain detectable, and preferably comparable, protease activity.

Wherein a variant of a polypeptide of interest is provided, the T-cell epitope may be altered in a number of ways including by amino acid substitutions, deletions, additions and combinations thereof. Preferably, the T-cell epitope is altered by having amino acid substitutions. In one embodiment herein, the amino acid substitutions are made to corresponding amino acids of a homolog of the polypeptide of interest, wherein the homolog does not comprise the same T-cell epitope in the corresponding position as the polypeptide of interest. In one aspect, the terminal portion of the polypeptide of interest comprising at least one T-cell epitope is replaced with a corresponding terminal portion of the homolog of the polypeptide of interest, wherein the replacement produces said different immunogenic response.

In another embodiment provided herein, the nucleic acids encoding the polypeptides producing the desired immunogenic response are provided herein. Moreover, the invention includes expression vectors and host cells comprising the nucleic acids provided herein. Moreover, once the polypeptides and variants thereof of the present invention are identified, substantially homologous sequences of or those sequences which hybridize to the polypeptides and variants can be identified and are provided herein. Homologous is further defined below, and can refer to similarity or identity, with identity being preferred. Preferably, the homologous sequences are amino acid sequences or nucleic acids encoding peptides having the activity of the polypeptides and variants provided herein.

In yet another aspect of the invention is a method for determining the immunogenic response produced by a protein. In one embodiment, the method comprises (a) obtaining from a single blood source a solution of dendritic cells and a solution of naive CD4+ and/or CD8+ T-cells; (b) promoting differentiation in said solution of dendritic cells; (c) combining said solution of differentiated dendritic cells and said naïve CD4+ and/or CD8+ T-cells with said protein; and (d) measuring the proliferation of T-cells in said step (c).

The methods of determining immunogenic responses produced by proteins can also be used to identify comparative immunogenic responses of proteins. Therefore, in one aspect, the method of determining immunogenic responses of proteins further comprises comparing immunogenic responses of one or more proteins. The proteins can be homologs of each other, variants of the same protein, different types of the same protein, for example, different proteases, or different peptides of the same protein.

The invention further provides a method of altering the immunogenicity of a polypeptide of interest comprising determining the immunogenicity of said polypeptide; identifying a T-cell epitope in a said polypeptide; and altering said T-cell epitope so as to alter the immunogenicity of said polypeptide. As described herein, said altering can be done by altering a single amino acid or switching a portion of a polypeptide of interest with a corresponding portion of a homolog, wherein the switch produces an altered immunogenic response.

Other aspects of the invention will be understood by the skilled artisan by the following description.

BRIEF DESCRIPTION OF THE DRAWINGS

FIGS. 1A, B1, B2 and B3 illustrate the DNA (SEQ ID NO: 1) and amino acid (SEQ ID NO: 2) sequence for *Bacillus amyloliquefaciens* subtilisin (BPN') and a partial restriction map of this gene.

FIG. 2 illustrates the conserved amino acid residues among subtilisins from *Bacillus amyloliquefaciens* and *Bacillus lentus* (wild-type).

FIGS. 3A and 3B illustrate an amino acid sequence alignment of subtilisin type proteases from *Bacillus amyloliquefaciens* (BPN') (SEQ ID NO: 3), *Bacillus subtilis* (SEQ ID NO: 4), *Bacillus licheniformis* (SEQ ID NO: 5) and *Bacillus lentus* (SEQ ID NO: 6). The symbol * denotes the absence of specific amino acid residues as compared to subtilisin BPN' (SEQ ID NO: 3).

FIGS. 6A and 6B/6C illustrate amino acid strings (SEQ ID NOS: 7 through 207) corresponding to peptides derived from the sequence of *Bacillus lentus* protease and a human subtilisin, respectively.

FIG. 7 illustrates the amino acid sequence of human subtilisin SEQ ID NO: 208.

FIG. 8 illustrates an amino acid sequence alignment of BPN' (*Bacillus amyloliquefaciens*) (SEQ ID NO: 3) protease, SAVINASE (*Bacillus lentus*) (SEQ ID NO: 6) protease and human subtilisin (S2HSBT) (SEQ ID NO: 209).

FIG. 18 is an embodiment of a hybrid protein (SEQ ID NO: 236) provided herein, where the N-terminus comprises N-terminal GG36 sequence and the C-terminus comprises C-terminal BPN' sequence, and wherein a comparison of the sequences with those shown in FIG. 8 indicates that the hybrid formed omits preferred T-cell epitopes of each protein.

DETAILED DESCRIPTION OF THE INVENTION

Figure 4:
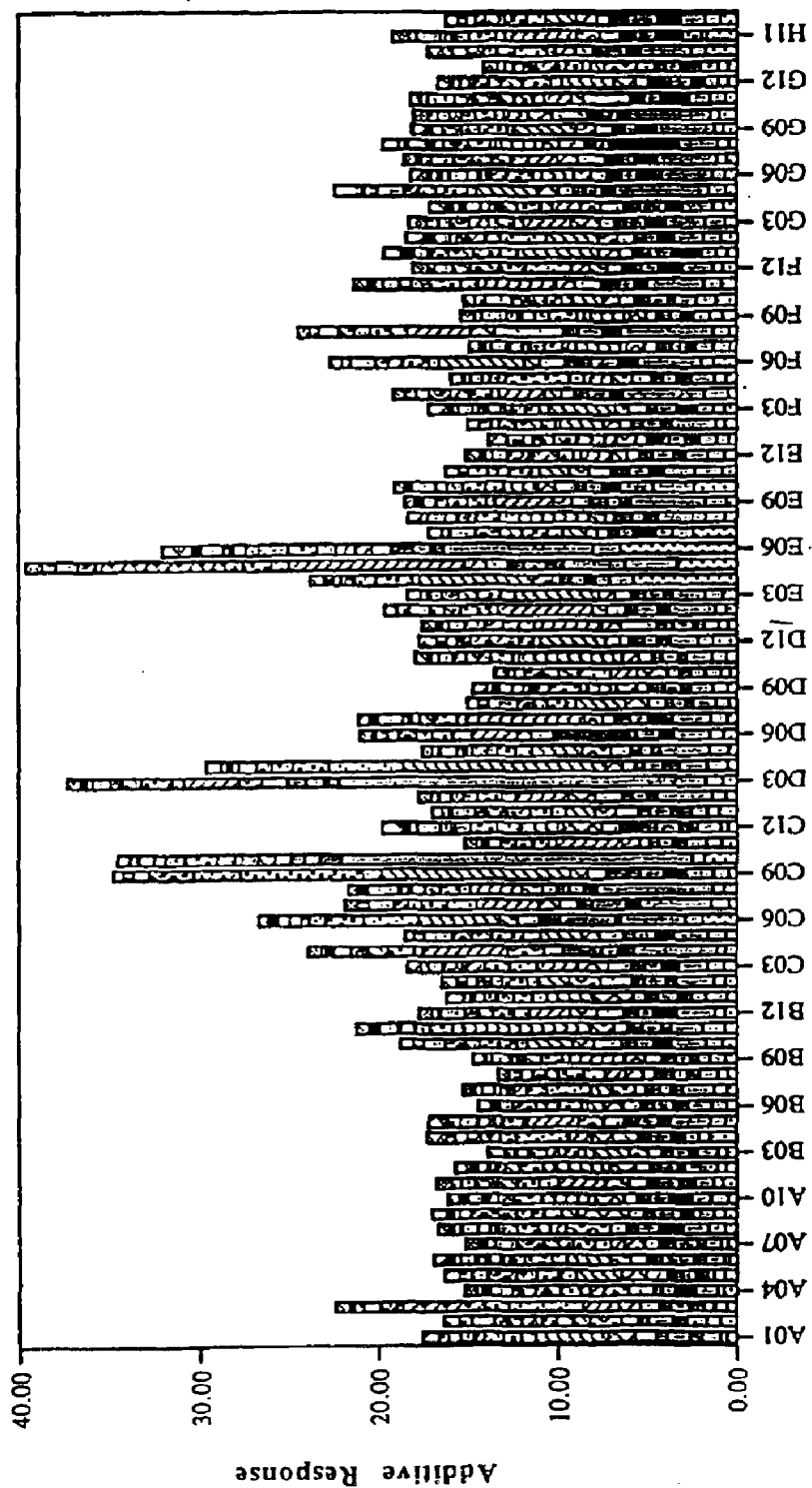
FIG. 4 illustrates the additive T-cell response of 16 peripheral mononuclear blood samples to peptides corresponding to the *Bacillus lentus* protease (GG36). Peptide E05 includes the region comprising residues corresponding to 170–173 in protease from *Bacillus amyloliquefaciens*.

According to the present invention, a method for identifying T-cell epitopes is provided. Moreover, proteins including naturally occurring proteins which have relatively impotent or potent T-cell epitopes or no T-cell epitopes may be identified in accordance with the methods of the present invention. Thus, the present invention allows the identification and production of proteins which produce immunogenic responses as desired, including naturally occurring proteins as well as proteins which have been mutated to produce the appropriate response. It is understood that the terms protein, polypeptide and peptide are sometimes used herein interchangeably. Wherein a peptide is a portion of protein, the skilled artisan can understand this by the context in which the term is used.

In one embodiment, the present invention provides an assay which identifies epitopes and non-epitopes as follows: differentiated dendritic cells are combined with naive human CD4+and/or CD8+T-cells and with a peptide of interest. More specifically, a method is provided wherein a T-cell epitope is recognized comprising the steps of: (a) obtaining from a single blood source a solution of dendritic cells and a solution of naïve CD4+ and/or CD8+ T-cells; (b) promoting differentiation in said solution of dendritic cells; (c) combining said solution of differentiated dendritic cells and said naive CD4+ and/or CD8+ T-cells with a peptide of interest; (d) measuring the proliferation of T-cells in said step (c).

In one embodiment, the peptide of interest to be analyzed is derived from a polypeptide of interest. In the practice of the invention, it is possible to identify with precision the location of an epitope which can cause sensitization in an individual or sampling of individuals. In a preferred embodiment of the invention, a series of peptide oligomers which correspond to all or part of the polypeptide of interest are prepared. For example, a peptide library is produced covering the relevant portion or all of the protein. In one embodiment, the manner of producing the peptides is to introduce overlap into the peptide library, for example, producing a first peptide corresponds to amino acid sequence 1–10 of the subject protein, a second peptide corresponds to amino acid sequence 4–14 of the subject protein, a third peptide corresponds to amino acid sequence 7–17 of the subject protein, a fourth peptide corresponds to amino acid sequence 10–20 of the subject protein etc. until representative peptides corresponding to the entire molecule are created. By analyzing each of the peptides individually in the assay provided herein, it is possible to precisely identify the location of epitopes recognized by T-cells. In the example above, the greater reaction of one specific peptide than its neighbors' will facilitate identification of the epitope anchor region to within three amino acids. After determining the location of these epitopes, it is possible to alter the amino acids within each epitope until the peptide produces a different T-cell response from that of the original protein. Alternatively, the epitope may be used in its original form to stimulate an immune response against a target, e.g. infectious agent or tumor cell. Moreover, proteins may be identified herein which have desired high or low T-cell epitope potency which may be used in their naturally occurring forms.

"Antigen presenting cell" as used herein means a cell of the immune system which present antigen on their surface which is recognizable by receptors on the surface of T-cells. Examples of antigen presenting cells are dendritic cells, interdigitating cells, activated B-cells and macrophages.

"T-cell proliferation" as used herein means the number of T-cells produced during the incubation of T-cells with the antigen presenting cells, with or without antigen.

"Baseline T-cell proliferation" as used herein means T-cell proliferation which is normally seen in an individual in response to exposure to antigen presenting cells in the absence of peptide or protein antigen. For the purposes herein, the baseline T-cell proliferation level was determined on a per sample basis for each individual as the proliferation of T-cells in response to antigen presenting cells in the absence of antigen.

"T-cell epitope" means a feature of a peptide or protein which is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II major histocompatability (MHC) molecules expressed on antigen-presenting cells (see e.g., Moeller, G. ed. "Antigenic Requirements for Activation of MHC-Restricted Responses," *Immunological Review*, Vol. 98, p. 187 (Copenhagen; Munksgaard) (1987).

"Sample" as used herein comprises mononuclear cells which are naïve, i.e., not sensitized, to the antigen in question.

"Homolog" as used herein means a protein or enzyme which has similar catalytic action, structure and/or use as the protein of interest. For purposes of this invention, a homolog and a protein of interest are not necessarily related evolutionarily, e.g., same functional protein from different species. It is desirable to find a homolog that has a tertiary and/or primary structure similar to the protein of interest as replacement of the epitope in the protein of interest with an analogous segment from the homolog will reduce the disruptiveness of the change. Thus, closely homologous enzymes will provide the most desirable source of epitope substitutions. Alternatively, if possible, it is advantageous to look to human analogs for a given protein. For example, substituting a specific epitope in a bacterial subtilisin with a sequence from a human analog to subtilisin (ie., human subtilisin) should result in less allergenicity in the bacterial protein.

An "analogous" sequence may be determined by ensuring that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids should maintain that specific structure.

The epitopes determined according to the assay provided herein are then modified to reduce or augment the immunologic potential of the protein of interest. In a preferred embodiment, the epitope to be modified produces a level of T-cell proliferation of greater than three times the baseline T-cell proliferation in a sample. When modified, the epitope produces less than three times the baseline proliferation, preferably less than two times the baseline proliferation and most preferably less than or substantially equal to the baseline proliferation in a sample.

Preferably, the epitope is modified in one of the following ways: (a) the amino acid sequence of the epitope is substituted with an analogous sequence from a human homolog to the protein of interest; (b) the amino acid sequence of the epitope is substituted with an analogous sequence from a non-human homolog to the protein of interest, which analogous sequence produces a lesser immunogenic, e.g., allergenic, response due to T-cell epitope recognition than that of the protein of interest; (c) the amino acid sequence of the epitope is substituted with a sequence which substantially mimics the major tertiary structure attributes of the epitope, but which produces a lesser immunogenic, e.g., allergenic, response due to T-cell epitope recognition than that of the protein of interest; or (d) with any sequence which produces lesser immunogenic, e.g., allergenic, response due to T-cell epitope recognition than that of the protein of interest.

However, one of skill will readily recognize that epitopes can be modified in other ways depending on the desired outcome. For example, if a T-cell vaccine is desired, it is contemplated the amino acid sequence of an epitope will be substituted with amino acids which increase the immulogic response to the peptide via enhanced MHC binding and/or T-cell recognition. In another example, if altering an autoimmune response against self-antigens is desired, it is contemplated the amino acid sequence of an epitope will be substituted with amino acids that decrease or cause a shift in an inflammatory or other immune response.

The present invention extends to all proteins against which it is desired to modulate the immunogenic response, for example; peptides to be used as T-cell vaccines, or peptides or proteins to be used as therapeutic agents against, e.g., cancer, infectious diseases and autoimmune diseases. One of skill in the art will readily recognize the proteins and peptides of this invention are not necessarily native proteins and peptides. Indeed, in one embodiment of this invention, the assay described herein is used to determine the immunologic response of proteins from shuffled genes. For descriptions of gene shuffling and expression of such genes see, Stemmer, *Proc. Nat'l Acad. Sci. USA* 91:10747 (1994); Patten, et al., *Current Opinion in Biotechnol.* 8:724 (1997); Kuchner & Arnold, *Trends Biotechnol.* 15:523 (1997); Moore, et al., *J. Mol, Biol.* 272:336 (1997); Zhao, et al., *Nature Biotechnol.* 16:258 (1998); Giver, et al., *Proc. Nat'l Acad. Sci. USA* 95:12809 (1998); Harayama, *Trends Biotechnol.* 16:76 (1998); Lin, et al., *Biotechnol., Prog.* 15:467 (1999); and Sun, *J. Comput. Biol.* 6:77 (1999). The assay is used to predict the immunologic response of proteins encoded by shuffled genes. Once determined, the protein can be altered to modulate the immunolgic response to that protein.

In addition to the above proteins and peptides, the present invention can be used to reduce the allergenicity of proteins. These proteins include, but are not limited to, glucanases, lipases, cellulases, endo-glucosidase Hs (endo-H), proteases, carbohydrates, reductases, oxidases, isomerases, transferases, kinases, phosphatases, amylases, etc. In addition to reducing the allergenicity to an animal, such as a human, of naturally occurring amino acid sequences, this invention encompasses reducing the allergenicity of a mutated human protein, e.g., a protein that has been altered to change the functional activity of the protein. In many instances, the mutation of human proteins to e.g., increase activity, results in the incorporation of new T-cell epitope in the mutated protein. The assay of this invention can be used to determine the presence of the new T-cell epitope and determine substitute amino acids that will reduce the allergenicity of the mutated protein.

Although this invention encompasses the above proteins and many others, for the sake of simplicity, the following will describe a particularly preferred embodiment of the invention, the modification of protease. Proteases are carbonyl hydrolases which generally act to cleave peptide bonds of proteins or peptides. As used herein, "protease" means a naturally-occurring protease or a recombinant protease. Naturally-occurring proteases include a-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

In one embodiment herein, hybrid polypeptides are provided. "Hybrid polypeptides" are proteins engineered from at least two different proteins, which are preferably homologs of one another. For example, a preferred hybrid polypeptide might have the N-terminus of a protein and the C-terminus of a homolog of the protein. In a preferred embodiment, the two terminal ends can be combined to correspond to the full-length active protein. In a preferred embodiment, the homologs share substantial similarity but do not have identical T-ell epitopes. Therefore, in one embodiment, for example, a polypeptide of interest having one or more T-cell epitopes in the C-terminus may have the C-terminus replaced with the C-terminus of a homolog having a less potent T-cell epitope in the C-terminus, less T-cell epitopes, or no T-cell epitope in the C-terminus. Thus, the skilled artisan understands that by being able to identify T-cell epitopes among homologs, a variety of variants producing different immunogenic responses can be formed. Moreover, it is understood that internal portions, and more than one homolog can be used to produce the variants of the present invention.

More generally, the variants provided herein can be derived from the precursor amino acid sequence by the substitution, deletion, insertion, or combination thereof of one or more amino acids of the precursor amino acid sequence. Such modification is preferably of the "precursor DNA sequence" which encodes the amino acid sequence of the precursor enzyme, but can be by the manipulation of the precursor protein. Suitable methods for such manipulation of the precursor DNA sequence include methods disclosed herein, as well as methods known to those skilled in the art (see, for example, EP 0 328299. WO89/06279 and the US patents and applications already referenced herein).

Figure 1B-2:
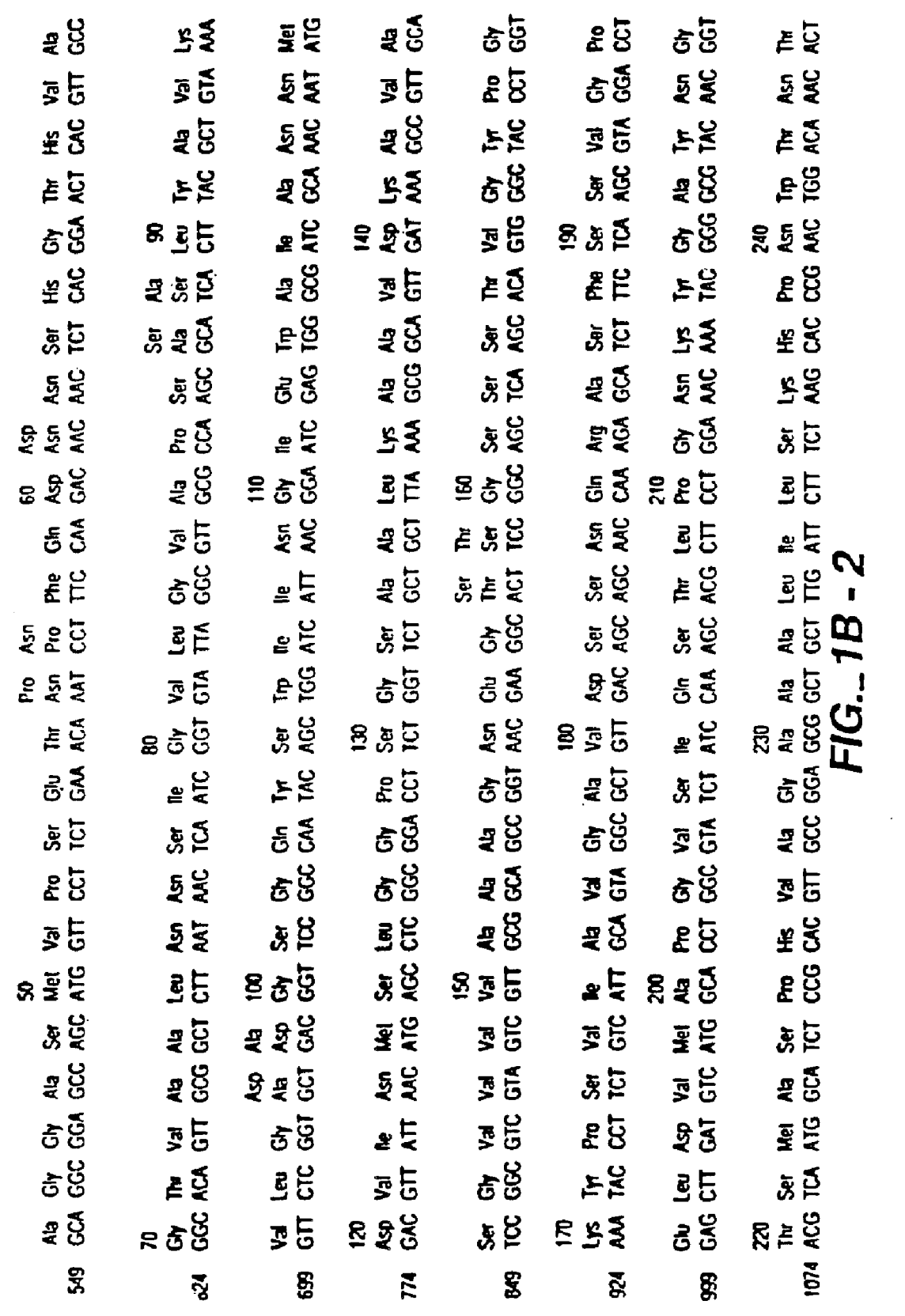

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are hot limited to the subtilisins identified in FIG. 3 herein. Generally and for purposes of the present invention, numbering of the amino acids in proteases corresponds to the numbers assigned to the mature *Bacillus amyloliquefaciens* subtilisin sequence presented in FIG. 1.

"Recombinant", "recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. No. 4,760,025 (U.S. Pat. No. RE. 34,606), U.S. Pat. No. 5,204,015 and U.S. Pat. No. 5,185, 258.

"Non-human subtilisins" and the DNA encoding them may be obtained from many procaryotic and eucaryotic organisms. Suitable examples of procaryotic organisms include gram negative organisms such as *E. coli* or *Pseudomonas* and gram positive bacteria such as *Micrococcus* or *Bacillus*. Examples of eucaryotc organisms from which subtilisin and their genes may be obtained include yeast such as *Saccharomyces cerevislae*, fungi such as *Aspergillus* sp.

"Human subtilisin" means proteins of human origin which have subtilisin type catalytic activity, e.g., the kexin family of human derived proteases. An example of such a protein is represented by the sequence in FIG. 7 (SEQ ID NO: 208). Additionally, derivatives or homologs of proteins provided herein, including those from non-human sources such as mouse or rabbit, which retain the essential activity of the peptide, such as the ability to hydrolyze peptide bonds, etc., have at least 50%, preferably at least 65% and most preferably at least 80%, more preferably at least 90%, and sometimes as much as 95 or 98% homology to the polypeptide of interest. In one embodiment, the polypeptide of interest is shown in the Figures.

The amino acid position numbers used herein refer to those assigned to the mature *Bacillus amyloliquefaciens* subtilisin sequence presented in FIG. 1. The invention, however, is not limited to the mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is *Bacillus lentus* subtilisin and the substitutions, deletions or insertions are made at the equivalent amino acid residue in *B. lentus* corresponding to those listed above.

A residue (amino acid) of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically). "Corresponding" as used herein generally refers to an analogous position along the peptide.

In order to establish homology to primary structure, the amino acid sequence of a precursor protease is directly compared to the *Bacillus amyloliquefaciens* subtilisin primary sequence and particularly to a set of residues known to be invariant in subtilisins for which the sequence is known. For example, FIG. 2 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, the amino acid sequence of subtilisin from *Bacillus amyloliquefaciens, Bacillus subtilis, Bacillus licheniformis* (*carfsbergensis*) and *Bacillus lentus* can be aligned to provide the maximum amount of homology between amino acid sequences. A comparison of these sequences shows that there are a number of conserved residues contained in each sequence. The conserved residues as between BPN' and *B. lentus* are identified in FIG. 2.

These conserved residues, thus, may be used to define the corresponding equivalent amino acid residues of *Bacillus amyloliquefaciens* subtilisin in other subtilisins such as subtilisin from *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B (SEQ ID NOS: 3–6) with the sequence of *Bacillus amyloliquefaciens* (SEQ ID NO: 3) subtilisin to produce the maximum homology of conserved residues. As can be seen, there are a number of deletions in the sequence of *Bacillus lentus* (SEQ ID NO: 6) as compared to *Bacillus amyloliquefaciens* (SEQ ID NO: 3) subtilisin. Thus, for example, the equivalent amino acid for Val165 in *Bacillus amyloliquefaciens* (SEQ ID NO: 3) subtilisin in the other subtilisins is isoleucine for *B. lentus* (SEQ ID NO: 6) and *B. licheniformis* (SEQ ID NO: 5).

Thus, for example, the amino acid at position +170 is lysine (K) in both *B. amyloliquefaciens* (SEQ ID NO: 3) and *B. licheniformis* (SEQ ID NO: 5) subtilisins and arginine (R) in Savinase (SEQ ID NO: 6). in one embodiment of the protease variants of the invention, however, the amino acid equivalent to +170 in *Bacillus amyloliquefaciens* subtilisin is substituted with aspartic acid (D). The abbreviations and one letter codes for all amino acids in the present invention conform to the Patentin User Manual (GenBank, Mountain View, Calif.) 1990, p. 101.

Homologous sequences can also be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970). by the search for similarity method of Pearson & Lipman, *Proc. Nat'l Acad. Sci. USA* 85:2444 (1988), by computerized implementations of these algorithms (GAP. BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology information (http://www.ncbi.nim.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin &

Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protein such as a protease if the smallest sum probability in a comparison of the test amino acid sequence to a protein such as a protease amino acid sequence is less than about 0.1, more preferably less than about 0.01, and most preferably less than about 0.001.

"Equivalent residues" may also be defined by determining homology at the level of tertiary structure for a precursor protein whose tertiary structure has been determined by x-ray crystallography. Equivalent residues are defined as those for which the atomic coordinates of two or more of the main chain atoms of a particular amino acid residue of the precursor protein such as the protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protein such as the protease in question to the *Bacillus amyloliquefaciens* subtilisin. The best model is the crystallographic model giving the lowest R factor for experimental diffraction data at the highest resolution $$R\ factor = \frac{\sum_{h} |Fo(h)| - |Fc(h)|}{\sum_{h} |Fo(h)|}$$

available.

Equivalent residues which are functionally analogous to a specific residue of *Bacillus amyloliquefaciens* subtilisin are defined as those amino acids of the precursor protein such as a protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protein, for example, protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The variants of the present invention include the mature forms of protein variants, as well as the pro- and prepro-forms of such protein variants. The prepro-forms are the preferred construction since this facilitates the expression, secretion and maturation of the protein variants.

"Prosequence" refers to a sequence of amino acids bound to the N-terminal portion of the mature form of a protein which when removed results in the appearance of the "mature" form of the protein. Many proteolytic enzymes are found in nature as translational proenzyme products and, in the absence of post-translational processing, are expressed in this fashion. A preferred prosequence for producing protein variants such as protease variants is the putative prosequence of *Bacillus amyloliquefaciens* subtilisin, although other prosequences may be used.

A "signal sequence" or "presequence" refers to any sequence of amino acids bound to the N-terminal portion of a protein or to the N-terminal portion of a proprotein which may participate in the secretion of the mature or pro forms of the protein. This definition of signal sequence is a functional one, meant to include all those amino acid sequences encoded by the N-terminal portion of the protein gene which participate in the effectuation of the secretion of protein under native conditions. The present invention utilizes such sequences to effect the secretion of the protein variants as defined herein. One possible signal sequence comprises the first seven amino acid residues of the signal sequence from *Bacillus subtilis* subtilisin fused to the remainder of the signal sequence of the subtilisin from *Bacillus lentus* (ATCC 21536).

A "prepro" form of a protein variant consists of the mature form of the protein having a prosequence operably linked to the amino terminus of the protein and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function Independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (U.S. Pat. No. RE. 34,606) to render them incapable of secreting enzymatically active endoprotease. A preferred host cell for expressing protein is the *Bacillus* strain BG2036 which is deficient in enzymatically active neutral protein and alkaline protease (subtilisin). The construction of strain BG2036 is described in detail in U.S. Pat. No. 5,264,366. Other host cells for expressing protein include *Bacillus subtilis* 1168 (also described in U.S. Pat. No. 4,760,025 (U.S. Pat. No. RE. 34,606) and U.S. Pat. No. 5,264,366, the disclosure of which are incorporated herein by reference), as well as any suitable *Bacillus strain* such as *B. licheniformis, B. lentus,* etc.

Host cells are transformed or transfected with vectors constructed using recombinant DNA techniques. These techniques can be found in any molecular biology practice guide, for example, Sambrook et al. Molecular Cloning—A Laboratory Manual (2nd ed.) Vol. 1–3, Cold Springs Harbor Publishing (1989) ("Sambrook"); and Current Protocols in Molecular Biology, Ausubel et al.(eds.), Current Protocols, a joint venture between Greene Publishing Associates, Inc. and John Wiley & Sons, Inc., (1997 Supplement) ("Ausubel"). Such transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

"Operably linked", when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occuring precursor protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

"Hybridization" is used to analyze whether a given DNA fragment or gene corresponds to a DNA sequence described herein and thus falls within the scope of the present invention. Samples to be hybridized are electrophoresed through an agarose gel (for example, 0.8% agarose) so that separation of DNA fragments can be visualized by size. DNA fragments are typically visualized by ethidium bromide staining. The gel may be briefly rinsed in distilled H2O and subsequently depurinated in an appropriate solution (such as, for example, 0.25M HCl) with gentle shaking followed by denaturation for 30 minutes (in, for example, 0.4 M NaOH) with gentle shaking. A renaturation step may be induded, in which the gel is placed in 1.5 M NaCl, 1MTris, pH 7.0 with gentle shaking for 30 minutes.

The DNA should then be transferred onto an appropriate positively charged membrane, for example, Maximum Strength Nytran Plus membrane (Schleicher & Schuell, Keene, N.H.), using a transfer solution (such as, for example, 6×SSC (900 mM NaCl, 90 mM trisodium citrate). Once the transfer is complete, generally after about 2 hours, the membrane is rinsed in e.g., 2×SSC (2×SSC=300 mM NaCl, 30 mM trisodium citrate) and air dried at room temperature. The membrane should then be prehybridized (for approximately 2 hours or more) in a suitable prehybridization solution (such as, for example, an aqueous solution containing per 100 mL: 20–50 mL formamide, 25 mL of 20×SSPE (1×SSPE=0.18 M NaCe, 1 mM EDTA, 10 mM NaH2PO4, pH 7.7), 2.5 mL of 20% SDS, and 1 mL of 10 mg/mL sheared herring or salmon sperm DNA). As would be known to one of skill in the art, the amount of formamide in the prehybridization solution may be varied depending on the nature of the reaction obtained according to routine methods. Thus, a lower amount of formamide may result in more complete hybridization in terms of identifying hybridizing molecules than the same procedure using a larger amount of formamide. On the other hand, a strong hybridization band may be more easily visually identified by using more formamide.

A DNA probe that is complementary or is nearly complementary to the DNA sequence of interest and is generally between 100 and 1000 bases in length is labeled (using, for example, the Megaprime labeling system according to the instructions of the manufacturer) to incorporate 32P in the DNA. The labeled probe is denatured by heating to 95° C. for 5 minutes and immediately added to the membrane and prehybridization solution. The hybridization reaction should proceed for an appropriate time and under appropriate conditions, for example, for 18 hours at 37° C. with gentle shaking or rotating. The membrane is rinsed (for example, in 2×SSC/0.3% SDS) and then washed in an appropriate wash solution with gentle agitation. The stringency desired will be a reflection of the conditions under which the membrane (filter) is washed.

Specifically, the stringency of a given reaction (i.e., the degree of homology necessary for successful hybridization) will depend on the washing conditions to which the filter is subjected after hybridization. "Low-stringency" conditions as defined herein will comprise washing a filter with a solution of 0.2×SSC/0.1% SDS at 20° C. for 15 minutes. "High-stringency" conditions comprise a further washing step comprising washing the filter a second time with a solution of 0.2×SSC/0.1% SDS at 37° C. for 30 minutes.

After washing, the membrane is dried and the bound probe detected. If 32P or another radioisotope is used as the labeling agent, the bound probe can be detected by autoradiography. Other techniques for the visualization of other probes are well-known to those of skill. The detection of a bound probe indicates a nucleic acid sequence has the desired homology and is encompassed within this invention.

The cloned protein is then used to transform a host cell in order to express the protein. The protein gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the protein gene in certain eucaryotic host cells) which is exogenous or is supplied by the endogenous terminator region of the protein gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the protein gene into host genome. This is facilitated by procaryotic and eucaryotic organisms which are particularly susceptible to homologous recombination.

In one embodiment, the gene can be a natural gene such as that from *B lentus* or *B. amytoliquefaciens*. Alternatively, a synthetic gene encoding a naturally-occuring or mutant precursor protein may be produced. In such an approach, the DNA and/or amino acid sequence of the precursor protein is determined. Multiple, overlapping synthetic single-stranded DNA fragments are thereafter synthesized, which upon hybridization and ligation produce a synthetic DNA encoding the precursor protein. An example of synthetic gene construction is set forth in Example 3 of U.S. Pat. No. 5,204,015, the disclosure of which is incorporated herein by reference.

Once the naturally-occurring or synthetic precursor protein gene has been cloned, a number of modifications are undertaken to enhance the use of the gene beyond synthesis of the naturally-occurring precursor protein. Such modifications include the production of recombinant proteins as disclosed in U.S. Pat. No. 4,760,025 (U.S. Pat. No. RE. 34,606) and EPO Publication No. 0 251 446 and the production of protein variants described herein.

The following cassette mutagenesis method may be used to facilitate the construction of the protein variants of the present invention, although other methods may be used. First, the naturally-occurring gene encoding the protein is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the protein gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

In one aspect of the invention, the objective is to secure a variant protein having altered allergenic potential as compared to the precursor protein, since decreasing such potential enables safer use of the enzyme. While the instant invention is useful to lower allergenic potential, the mutations specified herein may be utilized in combination with mutations known in the art to result altered thermal stability and/or altered substrate specificity, modified activity or altered alkaline stability as compared to the precursor.

Accordingly, the present invention is directed to altering the capability of the T-cell epitope which includes residue positions 170–173 in Bacillus lentus to induce T-cell proliferation. One particularly preferred embodiment of the invention comprises making modification to either one or all of R170D, Y171Q and/or N173D. Similarly, as discussed in detail above, it is believed that the modification of the corresponding residues in any protein will result in a the neutralization of a key T-cell epitope in that protein. Thus, in combination with the presently disclosed mutations in the region corresponding to amino acid residues 170–173, substitutions at positions corresponding to N76D/S103A/V104I/G159D optionally in combination with one or more substitutions selected from the group consisting of positions corresponding to V68A, T213R, A232V, Q236H, Q245R, and T260A of *Bacillus amyloliquefaciens* subtilisin may be used, in addition to decreasing the allergenic potential of the variant protein of the invention, to modulate overall stability and/or proteolytic activity of the enzyme. Similarly, the substitutions provided herein may be combined with mutation at the Asparagine (N) in *Bacillus lentus* subtilisin at equivalent position +76 to Aspartate (D) in combination with the mutations S103A/V104I/G159D and optionally in combination with one or more substitutions selected from the group consisting of positions corresponding to V68A, T213R, A232V, Q236H, Q245R, and T260A of *Bacillus amyloliquefaciens* subtilisin, to produce enhanced stability and/or enhanced activity of the resulting mutant enzyme.

The most preferred embodiments of the invention include the following specific combinations of substituted residues corresponding to positions:

N76D/S103A/V104I/G159D/K170D/Y171Q/S173D;
V68A/N76D/S103A/V104I/G159D/K170D/Y171Q/ S173D/Q236H;
V68A/N76D/S103A/V104I/G159D/K170D/Y171Q/ S173D/Q236H/Q245R;
V68A/N76D/S103A/V104I/G159D/K170D/Y171Q/ S173D/A232V/Q236H/Q245R; and
V68A/N76D/S103A/V104I/G159D/K170D/Y171Q/ S173D/T213R/A232V/Q236H/Q245R/T260A of *Bacillus amyloliquefaciens* subtilisin. These substitutions are preferably made in *Bacillus lentus* (recombinant or native-type) subtilisin, although the substitutions may be made in any *Bacillus* protein.

Based on the screening results obtained with the variant proteins, the noted mutations noted above in *Bacillus amyloliquefaciens* subtilisin are important to the proteolytic activity, performance and/or stability of these enzymes and the cleaning or wash performance of such variant enzymes.

Many of the protein variants of the invention are useful in formulating various detergent compositions. A number of known compounds are suitable surfactants useful in compositions comprising the protein mutants of the invention. These include nonionic, anionic, cationic anionic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protein variants of the present invention may be used for any purpose that native or wild-type proteins are used. Thus, these variants can be used, for example, in bar or liquid soap applications, dishcare formulations, contact lens cleaning solutions or products, peptide hydrolysis, waste treatment, textile applications, as fusion-cleavage enzymes in protein production, etc. The variants of the present invention may comprise, in addition to decreased allergenicity, enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteins, particularly proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteins, particularly proteases of the invention to conventional cleaning compositions does not create any special use limitation. In other words, any temperature and pH suitable for the detergent is also suitable for the present compositions as long as the pH is within the above range, and the temperature is below the described protein's denaturing temperature. In addition, proteins of the invention can be used in a cleaning composition without detergents, again either alone or in combination with builders and stabilizers.

The variant proteins of the present invention can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes variant proteins of the present invention. The composition can be used to treat for example silk or wool as described in publications such as RD 216,034; EP 134,267; U.S. Pat. No. 4,533,359; and EP 344,259.

The variants can be screened for proteolytic activity according to methods well known in the art. Preferred protease variants include multiple substitutions at positions corresponding to: N76D/S103A/V104I/G159D/K170D/Y171Q/S173D;
V68A/N76D/S103A/V104I/G159D/K170D/Y171Q/S173D/Q236H;
V68A/N76D/S103A/V104I/G159D/K170D/Y171Q/S173D/Q236H/Q245R;
V68A/N76D/S103A/V104I/G159D/K170D/Y171Q/Q245R;
V68A/N76D/S103A/V104I/G159D/K170D/Y171Q/S173D/A232V/Q236H/Q245R; and
V68A/N76D/S103A/V104I/GI59D/K170D/Y171Q/S173D/T213R/A232V/Q236H/Q245R/T260A
of *Bacillus amyloliquefaciens* subtilisin.

The proteins of this invention exhibit modified immunogenicity when compared to their precursor proteins. In preferred embodiments, the proteins exhibit reduced allergenicity. In other embodiments, the proteins exhibit increased immunogenicity. The increase in immunogenicity is manifested by an increase in B-cell or humoral immunological response, by an increase in T-cell or cellular immunological response, or by an increase in both B any T cell immunological responses. One of skill will readily recognize that the uses of the proteins of this invention will be determined, in large part, on the immunological properties of the proteins. For example, enzymes that exhibit reduced allergenicity can be used in cleaning compositions. "Cleaning compositions" are compositions that can be used to remove undesired compounds from substrates, such as fabric, dishes, contact lenses, other solid substrates, hair (shampoos), skin (soaps and creams), etc.

Proteins, in particular, cellulases, proteases, and amylases, with reduced allergenicity can also be used in the treatment of textiles. "Textile treatment" comprises a process wherein textiles, individual yarns or fibers that can be woven, felted or knitted into textiles or garments are treated to effect a desired characteristic. Examples of such desired characteristics are "stone-washing", depilling, dehairing, desizing, softening, and other textile treatments well known to those of skill in the art.

Therapeutic proteins against which individuals mount an immune response are also included in the invention. In particular, individuals who lack endogenous production of the protein are susceptible to forming neutralizing antibodies and become refractile to treatment. Likewise, modifications of a protein may introduce new epitopes that are potentially immunogeneic. Methods of the invention can be used to identify and modify epitopes in, e.g., human Factor VIII, to prevent neutralizing responses.

The pharmaceutical compositions can be prepared in various forms, such as granules, tablets, pills, suppositories, capsules, suspensions, salves, lotions and the like. Pharmaceutical grade organic or, inorganic carriers and/or diluents suitable for oral and topical use can be used to make up compositions containing the therapeutically active compounds. Diluents known to the art include aqueous media; vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

All publications and patents referenced herein are hereby incorporated by reference in their entirety. The following is presented by way of example and is not to be construed as a limitation to the scope of the claims.

EXAMPLES

Example 1

Assay for the Identification of Peptide T-Cell Epitopes Using Naïve Human T-Cells Fresh human peripheral blood cells were collected from "naïve" humans, i.e., persons not known to be exposed to or sensitized to *Bacillus lentus* protease, for determination of antigenic epitopes in protease from *Bacillus lentus* and human subtilisin. Naïve humans is intended to mean that the individual is not known to have been exposed to or developed a reaction to protease in the past. Peripheral mononuclear blood cells (stored at room temperature, no older than 24 hours) were prepared for use as follows: Approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature lymphoprep density separation media (Nycomed density 1.077 g/ml). The tubes were centrifuged for thirty minutes at 600G. The interface of the two phases was collected, pooled and washed in DPBS. The cell density of the resultant solution was measured by hemocytometer. Viability was measured by trypan blue exclusion.

From the resulting solution, a differentiated dendritic cell culture was prepared from the peripheral blood mononuclear cell sample having a density of 108 cells per 75 ml culture flask in a solution as follows:

(1) 50 ml of serum free AIM V media (Gibco) was supplemented with a 1:100 dilution beta-mercaptoethanol (Gibco). The flasks were laid flat for two hours to at 37° C. in 5% CO2 to allow adherence of monocytes to the flask wall.

(2) Differentiation of the monocyte cells to dendritic cells was as follows: nonadherent cells were removed and the resultant adherent cells (monocytes) combined with 30 ml of AIM V. 800 units/ml of GM-CSF (Endogen) and 500 units/ml of IL-4 (Endogen); the resulting mixture was cultured for 5 days under conditions at 37° C. in 5% CO2. After five days, the cytokine TNFa (Endogen) was added to 0.2 units/ml, and the cytokine IL-1a (Endogen) was added to a final concentration of 50 units/ml and the mixture incubated at 37° C. in 5% CO2 for two more days.

(3) On the seventh day, Mitomycin C was added to a concentration of 50 microgram/ml was added to stop growth of the now differentiated dendritic cell culture. The solution was incubated for 60 minutes at 37° C. in 5% CO2. Dendritic cells were collected by gently scraping the adherent cells off the bottom of the flask with a cell scraper. Adherent and non-adherent cells were then centrifuged at 600G for 5 minutes, washed in DPBS and counted.

(4) The prepared dendritic cells were placed into a 96 well round bottom array at 2×104/well in 100 microliter total volume of AIM V media.

CD4+ T cells were prepared from frozen aliquots of the peripheral blood cell samples used to prepare the dendritic cells using the human CD4+ Cellect Kit (Biotex) as per the manufacturers instructions with the following modifications: the aliquots were thawed and washed such that approximately 108 cells will be applied per Cellect column; the cells were resuspended in 4 ml DPBS and 1 ml of the Cell reagent from the Cellect Kit, the solution maintained at room temperature for 20 minutes. The resultant solution was centrifuged for five minutes at 600G at room temperature and the pellet resuspended in 2 ml of DPBS and applied to the Cellect columns. The effluent from the columns was collected in 2% human serum in DPBS. The resultant CD4+ cell solution was centrifuged, resuspended in AIMV media and the density counted.

The CD4+ T-cell suspension was resuspended to a count of 2×106/ml in AIM V media to facilitate efficient manipulation of the 96 well plate.

Peptide antigen is prepared from a 1 M stock solution in DMSO by dilution in AIM V media at a 1:10 ratio. 10 microliters of the stock solution is placed in each well of the 96 well plate containing the differentiated dendritic cells. 100 microliter of the diluted CD4+ T-cell solution as prepared above is further added to each well. Useful controls include diluted DMSO blanks, and tetanus toxoid positive controls.

The final concentrations in each well, at 210 microliter total volume are as follows:
2×104 CD4+
2×105 dendtritic cells (R:S of 10:1)
5 mM peptide Example 2

Identification of T-Cell Epitopes in Protease from Bacillus lentus and Human Subtilisin Peptides for use in the assay described in Example 1 were prepared based on the Bacillus lentus and human subtilisin amino acid sequence. Peptide antigens were designed as follows. From the full length amino acid sequence of either human subtilisin or Bacillus lentus protease provided in FIG. 1, 15 mers were synthetically prepared, each 15 mer overlapping with the previous and the subsequent 15 mer except for three residues.

Peptides used correspond to amino acid residue strings in Bacillus lentus as provided in FIG. 8 (SEQ ID NO: 6), and peptides correspond to amino acid residues in human subtilisin as provided in FIG. 7 (SEQ ID NO: 208). The peptides used corresponding to the proteases is provided in FIG. 6 (SEQ ID NOS: 7–207). All tests were performed at least in duplicate. All tests reported displayed robust positive control responses to the antigen tetanus toxoid. Responses were averaged within each experiment, then normalized to the baseline response. A positive event was recorded if the response was at least 3 times the baseline response.

Figure 5:
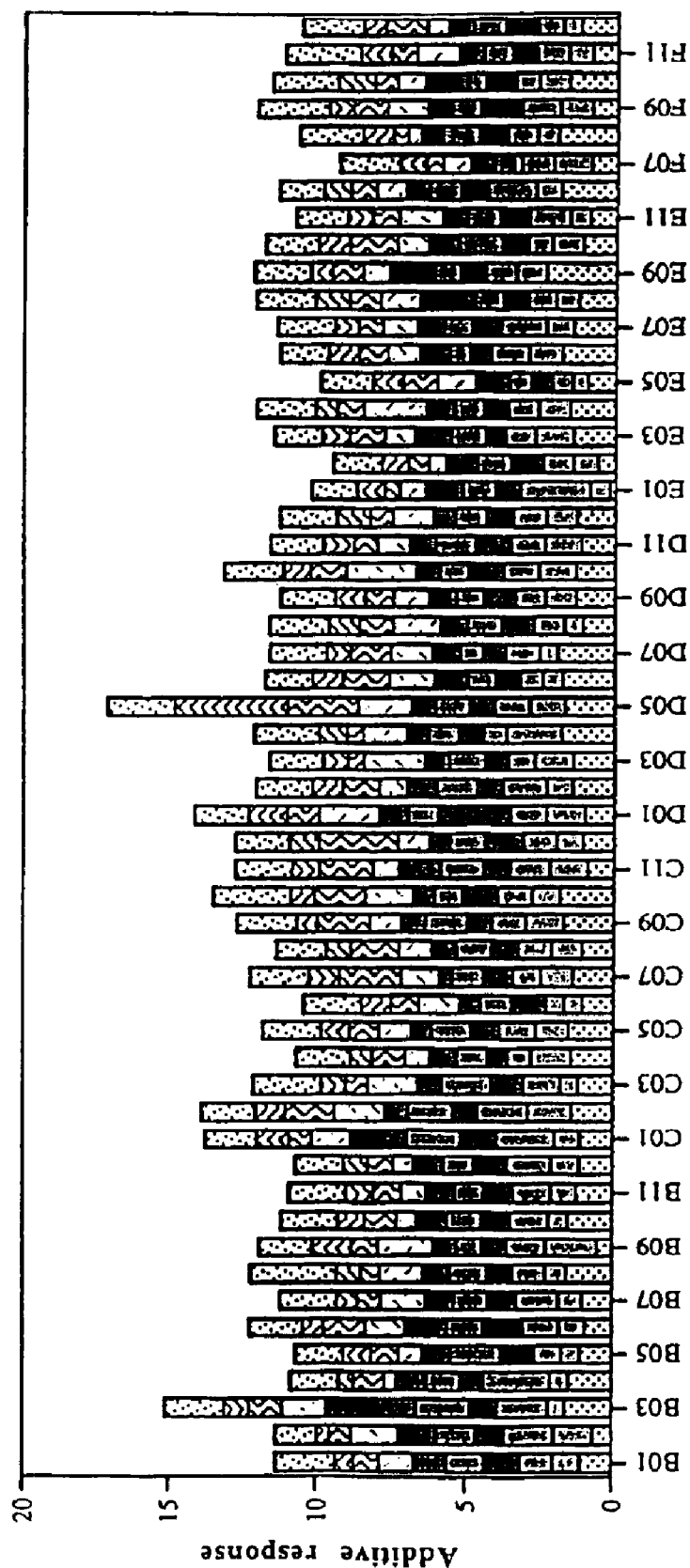
FIG. 5 illustrates the additive T-cell response of 10 peripheral mononuclear blood samples to peptides corresponding to the human subtilisin molecule. Peptides F10, F9, F8 and F7 all contain the amino acid sequence DQMD corresponding to the region comprising residues corresponding to 170–173 in protease from *Bacillus amyloliquefaciens* (SEQ ID NO: 3) in the sequence alignment of FIG. 3.

The immunogenic response (i.e., T-cell proliferation) to the prepared peptides from human subtilisin and Bacillus lentus was tallied and is provided in FIGS. 4 and 5, respectively. T-cell proliferation was measured by the incorporated tritium method. The results shown in FIGS. 4 and 5 as a comparison of the immunogenic additive response in 10 individuals (FIG. 4) and 16 individuals (FIG. 5) to the various peptides. Response is indicated as the added response wherein 1.0 equals a baseline response for each sample. Thus, in FIG. 4, a reading of 10.0 or less is the baseline response and in FIG. 5 a reading of 16.0 or less the baseline response. The greater the response, the more potent the T-cell epitope is considered.

As indicated in FIGS. 4 and 5, the immunogenic response of the naïve blood samples from unsensitized Individuals showed a marked allergenic response at the peptide fragment from Bacillus lentus corresponding to residues 170–173 of Bacillus amyloliquefaciens protease. As expected, the corresponding fragment in human subtilisin evokes merely baseline response.

Figure 9:
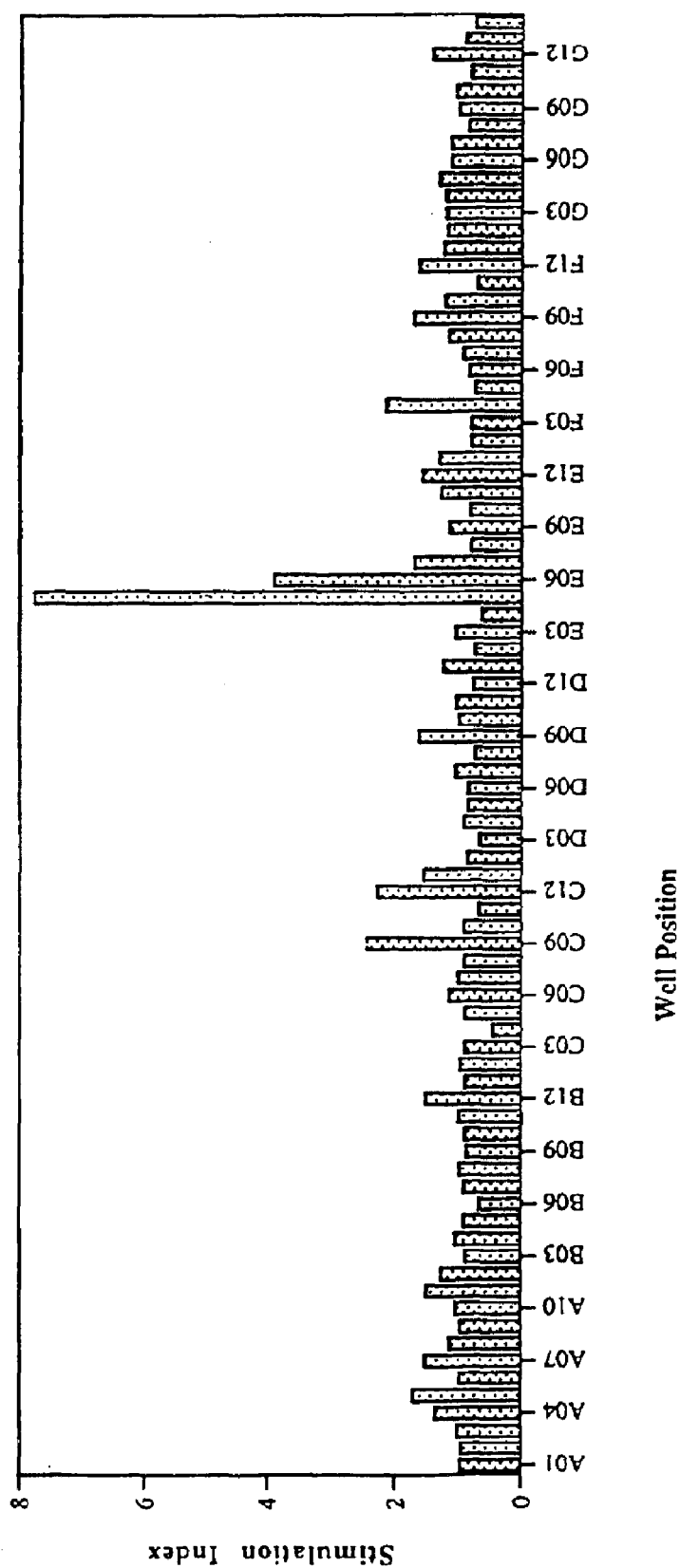
FIG. 9 illustrates the T-cell response to peptides derived from *Bacillus lentus* protease in a sample taken from an individual known to be hypersensitive to *Bacillus lentus* protease. Peptide E05 represents the region corresponding to 170–173 in protease from *Bacillus amyloliquefaciens*.

FIG. 9 shows the T-cell response to peptides derived from Bacillus lentus protease in a sample taken from an individual known to be hypersensitive to Bacillus lentus protease. Peptide E05 represents the region corresponding to 170–173 in protease from Bacillus amyloliquefaciens. As shown in FIG. 9, the hypersensitive individual was highly responsive to the T-cell epitope represented by the peptide E05. This result confirms that, by practicing the assay according to the invention, it is possible to predict the major epitopes identified by the T-cells of a hypersensitive individual.

Figure 10:
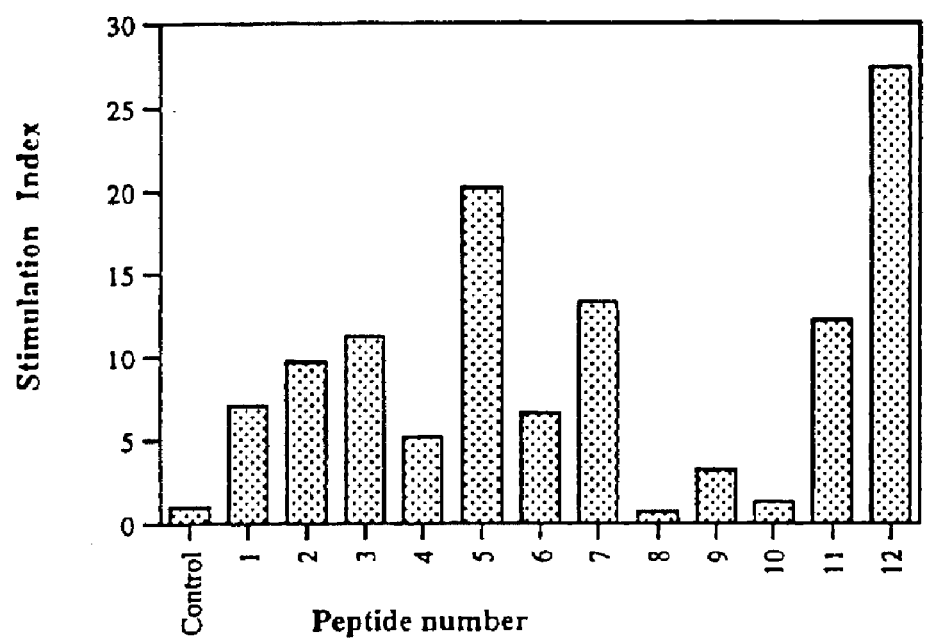
FIG. 10 illustrates the T-cell response to various alanine substitutions in the E05 *Bacillus lentus* protease peptide set in a sample taken from an individual known to be hypersensitive to *Bacillus lentus* protease.
Figure 11:
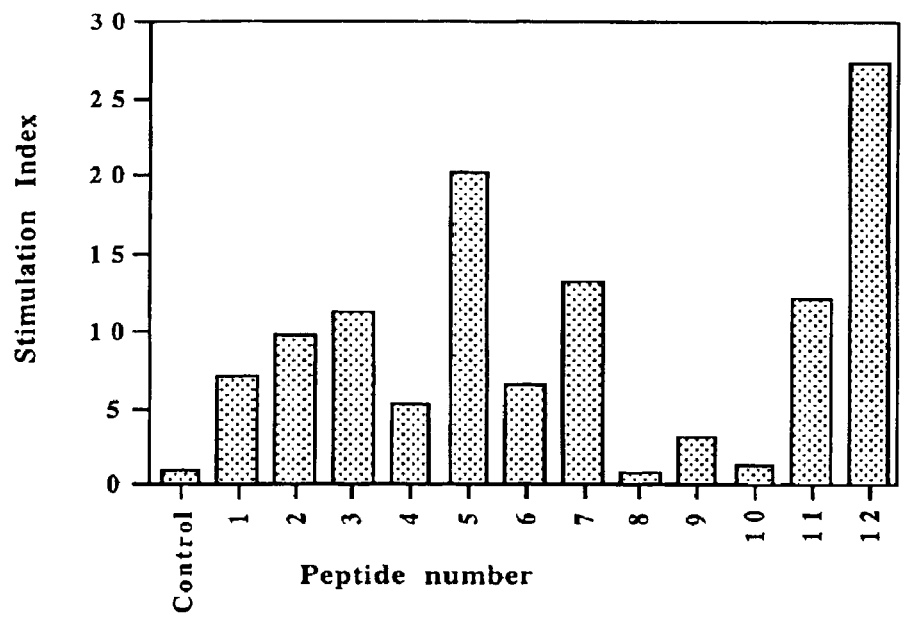
FIG. 11 illustrates the T-cell response to various alanine substitutions in the E05 protease peptide (an embodiment of the T-cell epitope designated unmodified sequence) set in a sample taken from an individual known to be hypersensitive to the protease; the sequences for each peptide (SEQ ID NOS: 210 through 221) are also shown.
Figure 12:
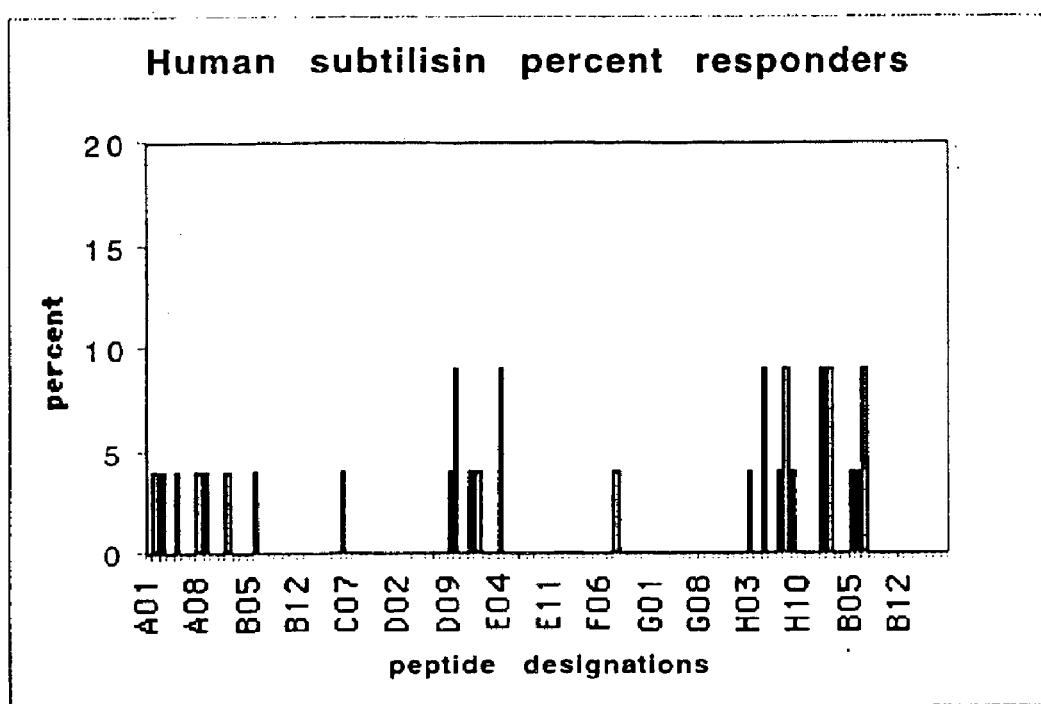
FIG. 12 illustrates the percent responders to the human subtilisin molecule.

FIG. 10 shows the T-cell response to various alanine substitutions in the E05 peptide derived from Bacillus lentus protease in a sample taken from an individual known to be hypersensitive to Bacillus lentus protease. Alanine substitutions were used as substitutions for the purpose of determining the role of any specific residue within the epitope. The legend of FIG. 10 refers to the position of the peptide in which an alanine was substituted, i.e., in peptide E06 (sequence GSISYPARYANAMAV (SEQ ID NO: 210) ), G to A=2, S to A=3, I to A=4, S to A=5, Y to A=6, P to A=7, R to A=8, Y to A=9, N to A=10, M to A=11 and V to A=12. As indicated in FIG. 10, substitution of either of the residues R170A, Y171A and/or N173A in protease from Bacillus lentus results in dramatically reduced response in the hypersensitive individual's blood sample.

From these results, it is apparent that the residues 170, 171 and 173 are largely responsible for the initiation of allergic reaction within the protease from Bacillus lentus.

Example 3

Identification of T-Cell Epitopes in Cellulase from Humicola insolens (Carezyme®)

Figure 13A:
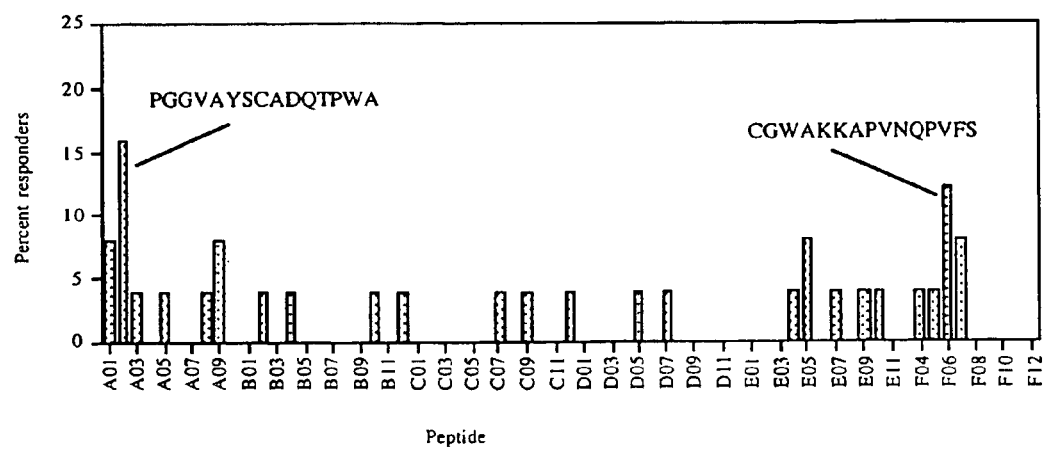
FIG. 13A illustrates the T-cell response of peptides derived from *Humicola insolens* endogluconase (Accession number A23635). Peptides A02 (SEQ ID NO: 222) and F06 (SEQ ID NO: 223) represent the region corresponding to residues 70–84 and 37–51, respectively, embodiments of the T-cell epitope, of *Humicola insolens* endogluconase (SEQ ID NO: 224), wherein the full length sequence is shown in FIG. 13B and A02 (SEQ ID NO: 222) and F06 (SEQ ID NO: 223) are shown underlined and in bold.

The procedure described above was performed on peptides derived from a cellulase from Humicola insolens (Carezyme® from Novo Nordisk). As can be seen from FIG. 13, 2 T-cell epitopes were discovered, A01 and F06.

Example 4

Identification of T-Cell Epitopes in Lipase from *Thermomyces Lanuqinosa* (Lipolase®)

Figure 14A:
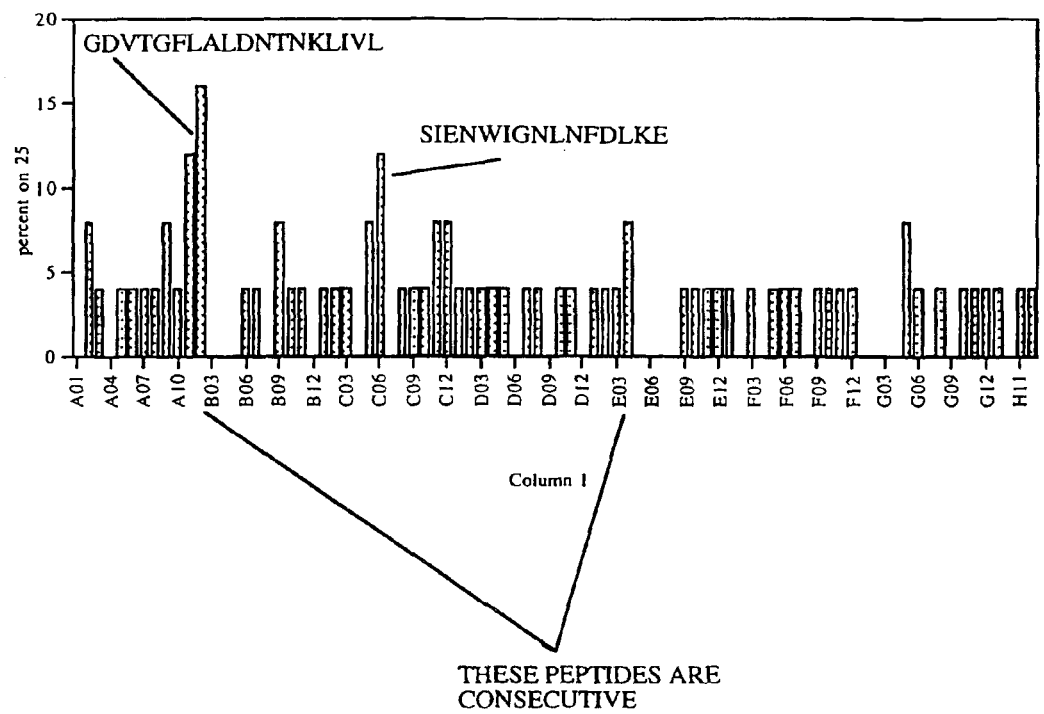
FIG. 14A illustrates the T-cell response to peptides derived from *Thermomyces lanuginosa* lipase (Accession number AAC08588 and PID number g2997733). Peptides B02 (SEQ ID NO: 225) and C06 (SEQ ID NO: 226) represent the regions corresponding to residues 83–100 and 108–121, respectively, embodiments of the T-cell epitope, of *Thermomyces lanuginosa* lipase (SEQ ID NO: 227), wherein the full length sequence is shown in FIG. 14B and B02 (SEQ ID NO: 225) and C06 (SEQ ID NO: 226) are shown underlined and in bold.

The procedure described in Example 2 was performed on peptides derived from a lipase from *Thermomyces lanuginosa* (Lipolase® from Novo Nordisk). As can be seen from FIG. 14, two T-cell epitopes were discovered, A12 and C06. Peptide E03 effected slightly increased T-cell proliferation in the naïve donors, however, this peptide is consecutive to A12 and they represent one epitope, in this regard, the skilled artisan understands that the length of the epitopes can be varied, and the precise potency of the epitope, naturally occuring or mutated can be determined by the methods herein.

Example 5

Identification of T-Cell Epitopes in Endoglucanase H from *Streptomyces plicatus*

Figure 15A:
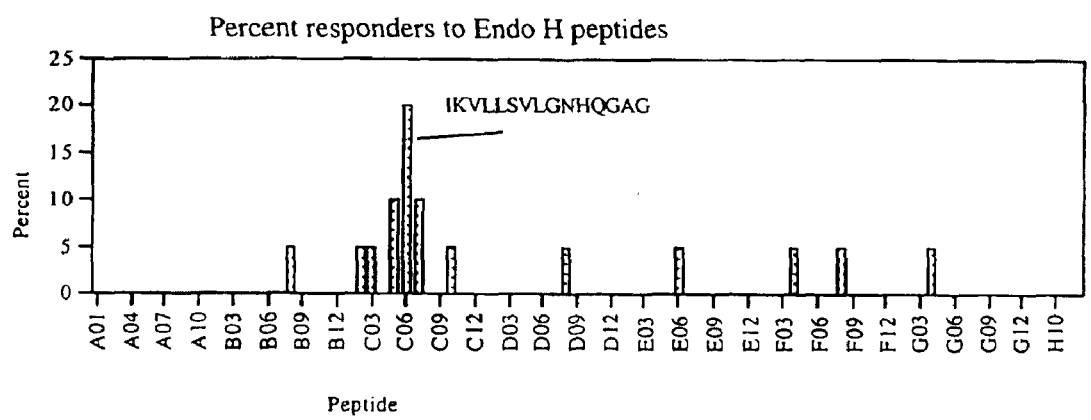
FIG. 15A illustrates the T-cell response to peptides derived from *Streptomyces plicatus* endo-beta-N-acetylglucosaminidase. (Accession number P04067). Peptide C06 (SEQ ID NO: 228) represents the region corresponding to residues 126–140, an embodiment of the T-cell epitope, of *Streptomyces plicatus* endo-beta-N-acetylglucosaminidase (SEQ ID NO: 229), wherein the full length sequence is shown in FIG. 15B and C06 (SEQ ID NO: 228) is shown underlined and in bold.

The procedure described in Example 2 was performed on peptides derived from endoglucanase H from *Streptomyces plicatus*. As can be seen from FIG. 15, a single T-cell epitope was discovered, C06.

Example 6

Identification of T-Cell Epitopes in a Protease Hybrid (GG36-BPN') (SEQ ID NO: 236)

After determining the location of a T-cell epitope, a protease hybrid was constructed using established protein engineering techniques. The hybrid was constructed so that a highly allergenic amino acid sequence of the protein was replaced with a corresponding sequence from a less allergenic homolog, in this instance, the first 122 amino acids of the protease were derived from GG36, and the remaining amino acid sequence was derived from BPN'.

The hybrid was first tested from a 100 ppm sample in North American condition in 24 well assay at 0.5 ppm, superfixed swatches, liquid (Tide KT) at 0.5 in 24 well assay with 3K swatches, and in the N'N'-dimethyl Casein Assay, 5 g/l DMC in NA detergent, TNBS dectection method.

Figure 16:
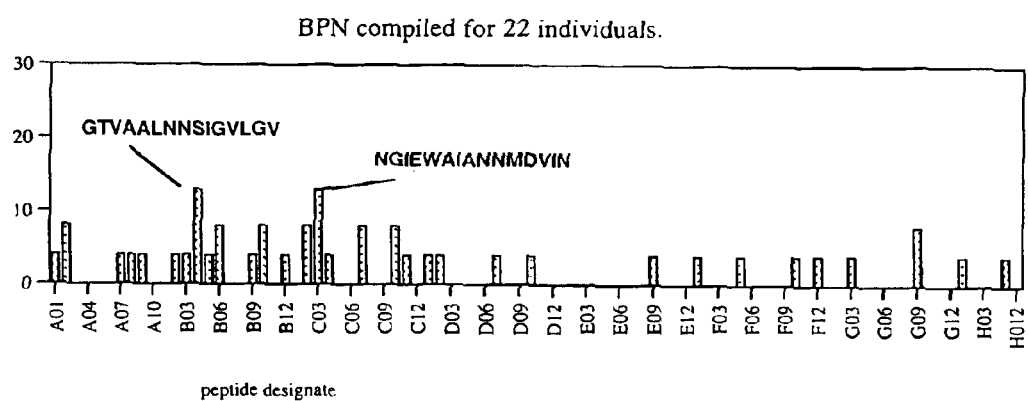
FIG. 16 illustrates the T-cell response to peptides derived from BPN' compiled for 22 individuals, wherein the sequences of preferred T-cell epitopes (SEQ ID NO: 230 through 231) are indicated.
Figure 17:
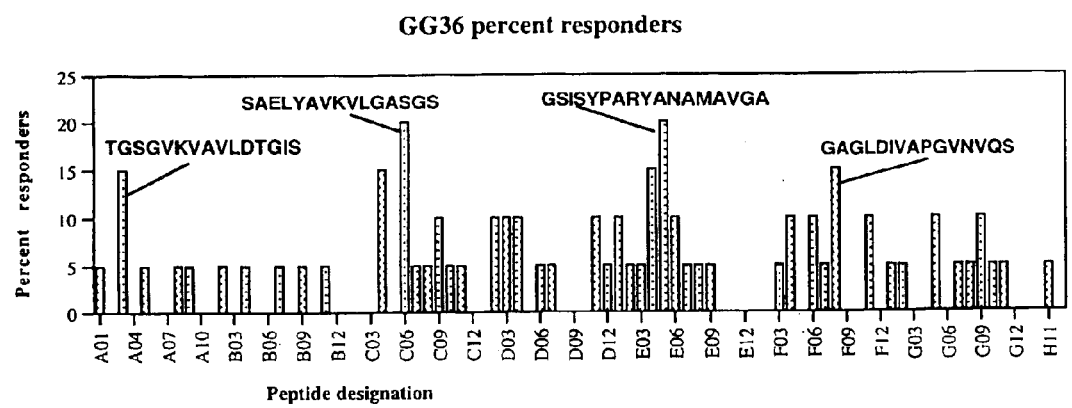
FIG. 17 illustrates the T-cell response to peptides derived from GG36 compiled for 22 individuals, wherein the sequences of embodiments of T-cell epitopes (SEQ ID NO: 232 through 235) are indicated, GSISYPARYANAMAVGA (SEQ ID NO: 234) and GAGLDIVAPGVNVQS (SEQ ID NO: 235) being preferred.
Figure 19A:
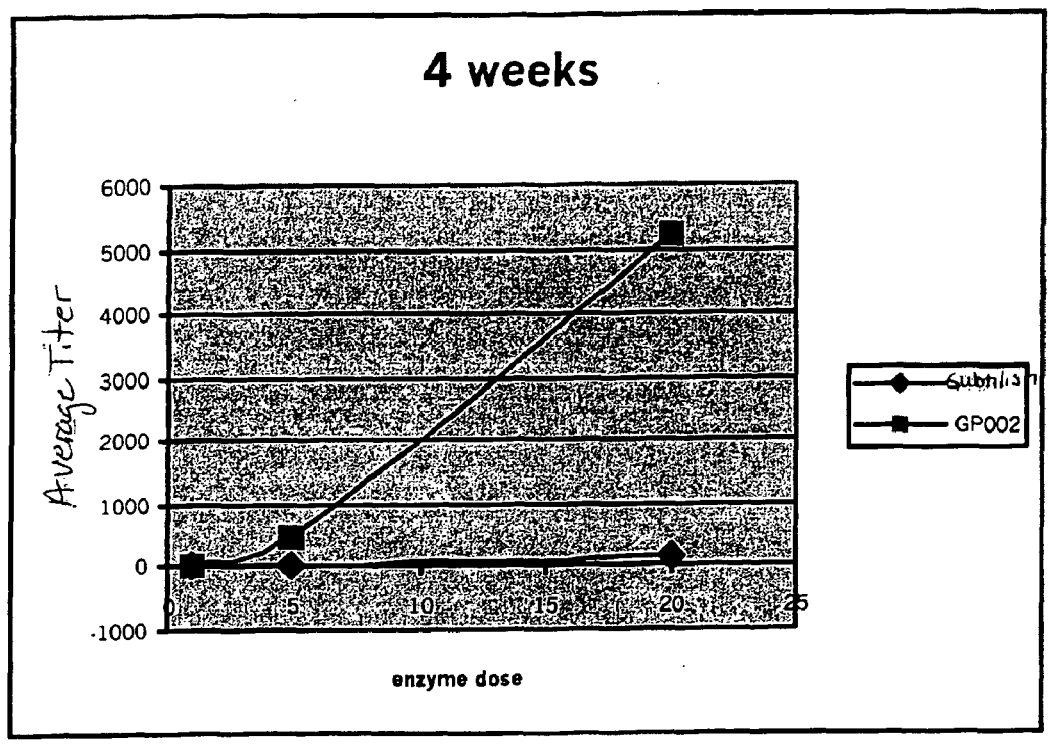
FIG. 19a represents the titer at 4 weeks.
Figure 19B:
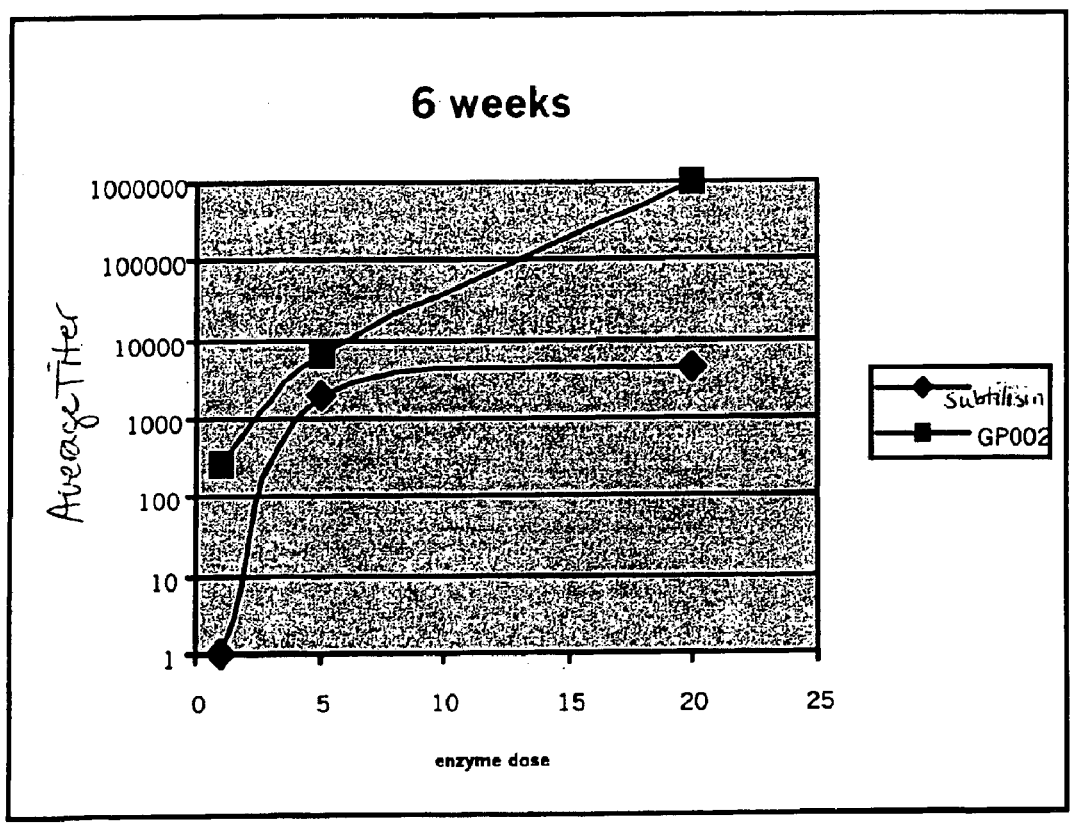
FIG. 19b at 6 weeks, FIG. 19c at 8 weeks and FIG. 19d at 10 weeks.
Figure 19C:
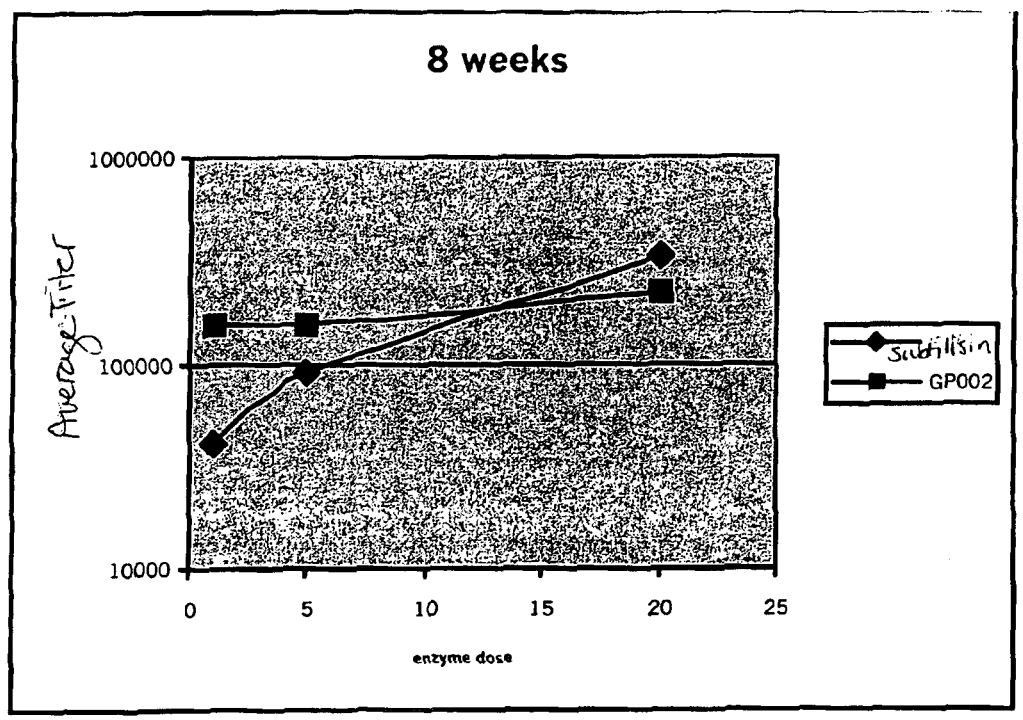
FIG. 19 is a comparison of ELISA titers for *B. amyloliquefaciens* subtilisin and the same subtilisin but engineered to contain a T-cell epitope from *B. lentus* subtilisin.
Figure 19D:
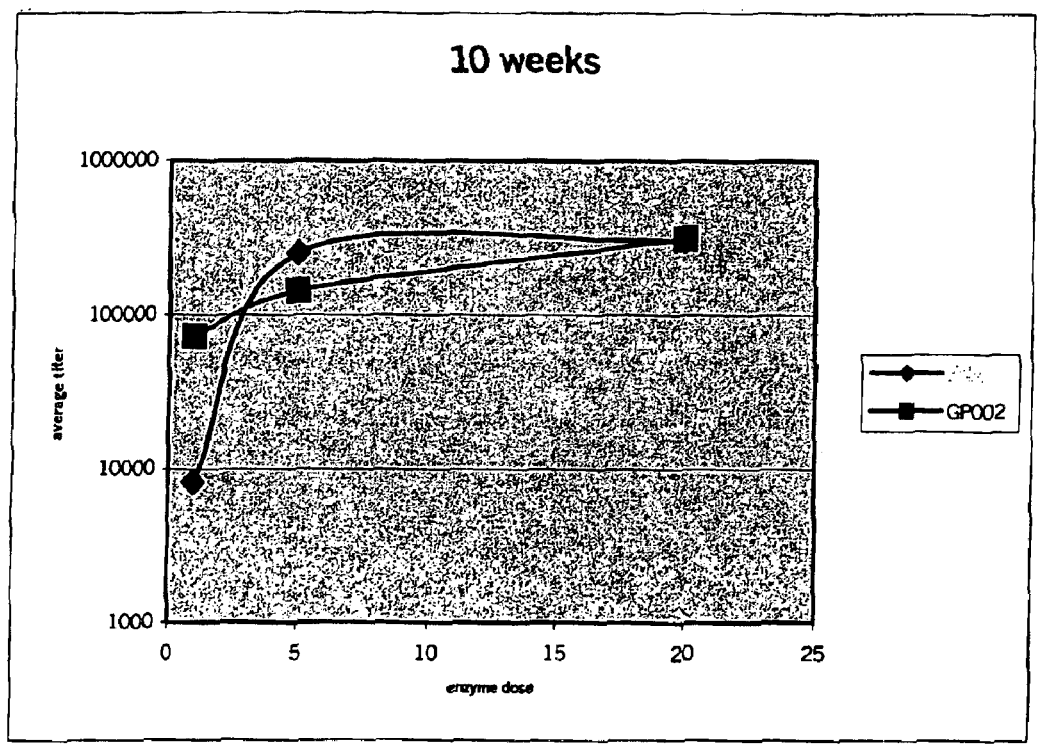

The results are shown in FIGS. 16 (SEQ ID NOS: 230 and 231), 17 (SEQ ID NOS: 232 through 235) and 18 (SEQ ID NO: 236).

Example 7

Identification of a Naturally Occuring Low Immunogenic Protein

Using the methods herein, proteinase K was identified as producing a lower immunogenic response than other commercially available proteases. Proteinase K as Identified herein is from Tritirachium Album limber. For a general description of proteases and methodologies, see, Mathew, C. G. P. Isolation of high molecular weight eukaryotic DNA, in Methods in Molecular Biology, vol. 2:. Nucleic Acids (Walker, J. M.,ed.), Humana, Clifton, N.J., (1984) pp. 31–34.

Example 8

T-cell Epitope Introduced into a Non-allergenic Protein

It has been found that *Bacillus amyloliquefaciens* subtilisin is comparatively non-immunogenic when tested in Hartley strain guinea pigs. A related protein from *Bacillus lentis* is highly immunogenic. We had previously defined functional T cell epitopes in the *B. lentis* molecule which were not found in the *B. amyloliquefaciens* molecule, even though the sequences of interest were highly homologous, in order to test the principle that the presence of a functional T cell epitope can control the relative levels of antibody production, we created a *B. lentis*-like T cell epitope in the *B. amyloliquefaclens* molecule. This change was accomplished by the substitution of a single amino acid in the *B. amyloliquefaciens* sequence. *B. amyloliquefaciens* subtilisin and the T cell epitope modified variant of *B. amyloliquefaciens* subtilisin were tested in a guinea pig model of immunogenicity.

*B. lentis* and *B. amyloliquefaciens* subtilisin T cell epitope mapping: Guinea pigs were immunized with 20 µg/immunization of subtilisin from either *B. lentis* or *B. amyloliquefaciens*. Animals were immunized subcutaneously in adjuvant every two weeks for 10 to 12 weeks. A single cell suspension of guinea pig splenocytes was created from each animal's spleen. Cells were plated at $5 \times 10^5$ splenocytes per well in round bottom 96 well plates. 15-mer peptides off-set by 3 amino acids were synthesized by Mimotopes. Peptides were resuspended to 1 mM in DMSO. Peptides were added to the cells at a final concentration of 5 µM. Cultures were incubated for 5 days at 37°, 5% $CO_2$. Wells were pulsed with 0.5 µCi tritiated thymidine, and allowed to incubate for an additional 18 hours. Wells were harvested, and thymidine incorporation assessed.

Two T cell epitopes were found in *B. lentis* subtilisin, and none were found in *B. amyloliquefaciens* subtilisin (>10 animals tested for these epitopes). The *B. lentis* T cell epitopes were found to comprise the following sequences: IAALNNSIGVLGVAP (SEQ ID NO:237) and LEWAGNNGMHVANLSLGS (SEQ ID NO:238)

For SEQ ID NO:237, the similar sequence in *B. amyloliquefaciens* subtilisin is VAALNNSIGVLGVAP (SEQ ID NO:239). The similar region in *B. amylotiquefaciens* subtilisin for SEQ ID NO:238 was the much less homologous: IEWAIANNMDVINMSLG (SEQ ID NO:240).

SEQ ID NO:237 and the homologous region in the *B. amyloliquefaciens* subtilisin molecule (SEQ ID NO: 239) differ by one amino acid: in *B. lentis* subtilisin the first amino acid is an 1, while it is a V in *B. amytoliquefaciens*. Therefore, we reasoned that if we changed the V in the *B. amyloliquefaciens* sequence to an I, we would create the *B. lentis* T cell epitope in the *B. amyloliquefaciens* backbone.

This molecule was created by standard molecular biological techniques, and was called *B. amyloliquefaciens* V72I. It was also known as GP002.

Guinea pig immunizations: Adult female Hartley guinea pigs were immunized with various doses of *B. amyloliquefaciens* subtilisin and GP002. The doses were 1, 5, 10, and 20 µg/dose. There were four animals for each dose. Animals were immunized subcutaneously with enzyme in Complete Freund's Adjuvant for the first immunization. All subsequent immunizations were performed in Incomplete Freund's adjuvant. Animals were immunized, and a serum sample taken, every two weeks.

ELISA: A direct ELISA was performed. Costart EIA plates were coated with 10 µg/ml of the immunizing enzyme in PBS overnight at 4° C. Plates were washed and blocked with 1% BSA in PBS. Serum samples were diluted in 1% BSA/PBS, and incubated on the enzymes coated plates for 1 hour. Serum samples were washed out, and biotinylated anti-guinea pig IgG was added at a 1:10,000 dilution in 1% BSA/PBS. The secondary reagent was incubated for 1 hour.

The wells were washed, and avidin conjugated horse radish peroxidase was added to the wells at a 1:1000 dilution in 1% BSA/PBS. After 30 minutes, the substrate (ABTS) was added and the $OD_{405}$ was read after 30 minutes.

Calculation of titers: Background was subtracted from the OD readings, and the results plotted for each individual guinea pig. A linear regression analysis was performed on the linear portion of the curve. The titer value was calculated from the linear regression equation for an OD=0.5. These individual titers were then averaged.

Two guinea pigs in the 10 μg dose of GP001 died at 2 weeks into the study. The data for the 10 μg dose was therefore thrown out.

Two results are immediately apparent: first, the GP002 variant increased the titers of antigen-specific antibody over the entire time course for the lower doses of enzymes; and the GP002 variant increased titers of antigen-specific antibody for all doses of enzymes in the earliest time points.

Figure 20A:
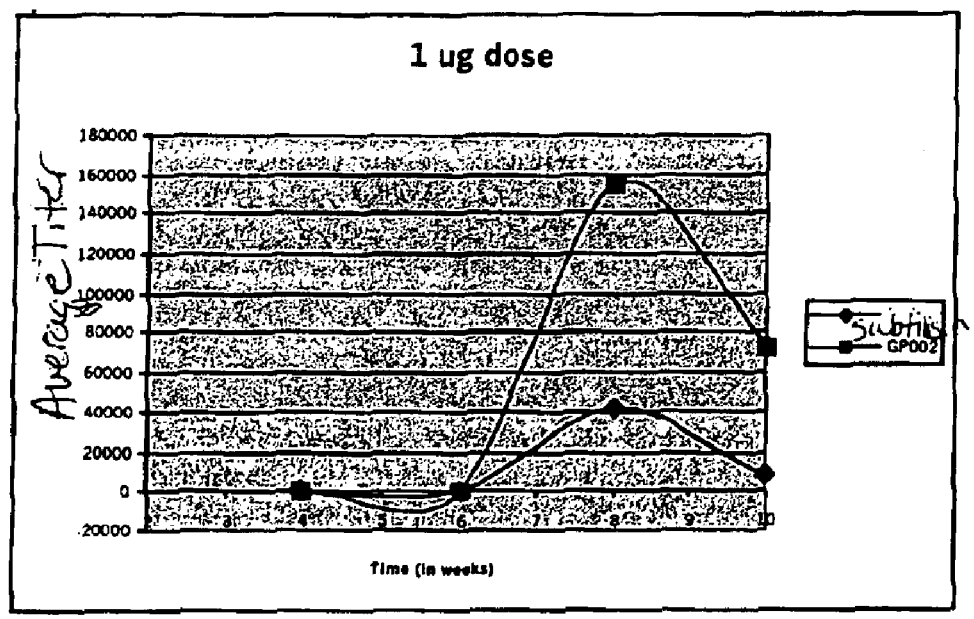
FIG. 20a represents the titer for a 1 μg dose of enzyme, FIG. 20b a 5 μg dose and FIG. 20c a 20 μg dose.
Figure 20B:
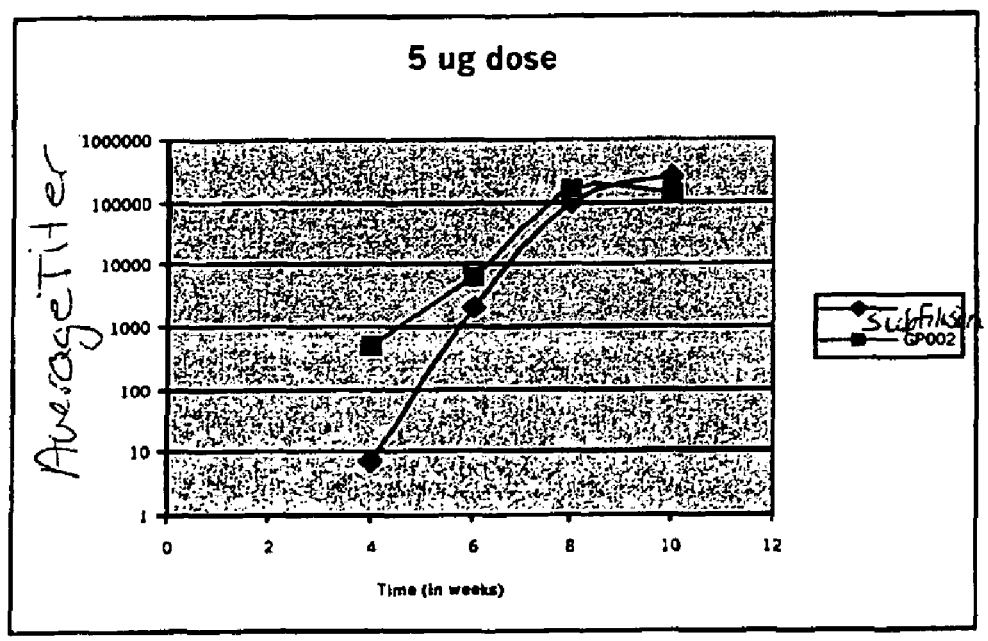
FIG. 20 is a time course study of ELISA titers for *B. amyloliquefaciens* subtilisin and the same subtilisin but engineered to contain a T-cell epitope from *B. lentus* subtilisin.
Figure 20C:
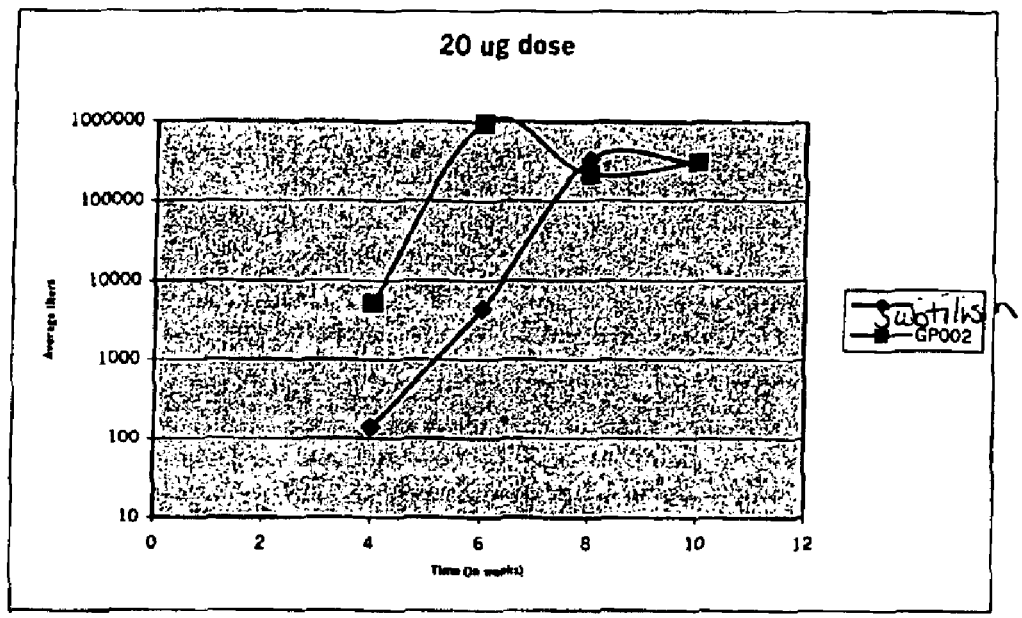

At the extended time points and for the higher doses, the difference between B. amyloliquefaciens subtilisin and its variant were no longer apparent. See FIGS. 19 and 20.

From the Figures it is apparent that a single change in the amino acid sequence of B. amyloliquefacions subtilisin significantly altered its immunogenicity.

We claim:

1. A variant of a polypeptide of interest comprising a T-cell epitope, wherein said variant differs from said polypeptide of interest by having an altered T-cell epitope such that said variant produces an immunogenic response in an individual which is greater than the immunogenic response produced by said polypeptide of interest, wherein said T-cell epitope of said polypeptide of interest is altered to produce said variant, and wherein said T-cell epitope is altered by having a terminal portion of said polypeptide of interest comprising said T-cell epitope replaced with a corresponding terminal portion of a homolog of said polypeptide of interest wherein said homolog does not comprise a T-cell epitope identical to said replaced T-cell epitope.

2. The variant of claim 1, wherein said polypeptide of interest is not recognized by said individual as endogenous to said individual.

3. The variant of claim 1, wherein said T-cell epitope is altered with amino acid substitutions.

4. A variant of a polypeptide of interest comprising at least one T-cell epitope, wherein said variant differs from said polypeptide of interest by having at least one altered T-cell epitope, such that said variant produces an immunogenic response in an individual which is greater than the immunogenic response produced by said polypeptide of interest, wherein said at least one T-cell epitope of said polypeptide of interest is altered to produce said variant, and wherein said T-cell epitope is altered by having a terminal portion of said polypeptide of interest comprising said T-cell epitope replaced with a corresponding terminal portion of a homolog of said polypeptide of interest wherein said homolog does not comprise a T-cell epitope identical to said replaced T-cell epitope.

5. The variant of claim 4, wherein said polypeptide of interest is not recognized by said individual as endogenous to said individual.

6. The variant of claim 4, wherein said T-cell epitope is altered with amino acid substitutions.

* * * * *